(12) United States Patent
Brown et al.

(10) Patent No.: US 11,773,090 B2
(45) Date of Patent: *Oct. 3, 2023

(54) PHARMACEUTICAL COMPOUNDS

(71) Applicant: Heptares Therapeutics Limited, Cambridge (GB)

(72) Inventors: Giles Albert Brown, Cambridge (GB); Barry John Teobald, Cambridge (GB); Benjamin Gerald Tehan, Cambridge (GB)

(73) Assignee: Heptares Therapeutics Limited, Cambridgeshire (GB)

( * ) Notice: Subject to any disclaimer, the term of this patent is extended or adjusted under 35 U.S.C. 154(b) by 115 days.

This patent is subject to a terminal disclaimer.

(21) Appl. No.: 17/024,085

(22) Filed: Sep. 17, 2020

(65) Prior Publication Data

US 2021/0002271 A1 Jan. 7, 2021

Related U.S. Application Data

(63) Continuation of application No. 16/450,261, filed on Jun. 24, 2019, now Pat. No. 10,787,447.

(30) Foreign Application Priority Data

Jun. 22, 2018 (GB) ..................................... 1810239

(51) Int. Cl.
    *C07D 451/14* (2006.01)
    *A61P 25/28* (2006.01)

(52) U.S. Cl.
    CPC ............ *C07D 451/14* (2013.01); *A61P 25/28* (2018.01)

(58) Field of Classification Search
    None
    See application file for complete search history.

(56) References Cited

U.S. PATENT DOCUMENTS

| | | | |
|---|---|---|---|
| 5,446,051 A | 8/1995 | Ornstein | |
| 5,852,029 A | 12/1998 | Fisher et al. | |
| 5,854,245 A | 12/1998 | Duggan et al. | |
| 6,335,341 B1 | 1/2002 | Johnson et al. | |
| 6,387,930 B1 | 5/2002 | Baroudy et al. | |
| 6,699,880 B1 | 3/2004 | Yamakawa et al. | |
| 7,067,507 B2 | 6/2006 | Pulley et al. | |
| 7,163,938 B2 | 1/2007 | Herron et al. | |
| 7,524,852 B2 | 4/2009 | Arai et al. | |
| 7,531,537 B2 | 5/2009 | Kawaguchi et al. | |
| 8,119,661 B2 | 2/2012 | Cheng et al. | |
| 8,476,289 B2 | 7/2013 | Freyne et al. | |
| 9,067,951 B2 | 6/2015 | Ebel et al. | |
| 9,187,451 B2 | 11/2015 | Congreve et al. | |
| 9,266,857 B2 | 2/2016 | Brown et al. | |
| 9,573,929 B2 | 2/2017 | Congreve et al. | |
| 9,593,106 B2 | 3/2017 | Livermore et al. | |
| 9,669,013 B2 | 6/2017 | Brown et al. | |
| 9,670,183 B2 | 6/2017 | Brown et al. | |
| 9,758,506 B2 | 9/2017 | Brown et al. | |
| 9,907,805 B2 | 3/2018 | Congreve et al. | |
| 9,926,297 B2 | 3/2018 | Brown et al. | |
| 9,957,257 B2 | 5/2018 | Nirogi et al. | |
| 9,975,890 B2 | 5/2018 | Brown et al. | |
| 10,030,012 B2 | 7/2018 | Livermore et al. | |
| 10,030,035 B2 | 7/2018 | Congreve et al. | |
| 10,167,272 B2 | 1/2019 | Brown et al. | |
| 10,167,284 B2 | 1/2019 | Congreve et al. | |
| 10,196,380 B2 | 2/2019 | Brown et al. | |
| 10,259,787 B2 | 4/2019 | Brown et al. | |
| 10,259,802 B2 | 4/2019 | Brown et al. | |
| 10,329,278 B2 | 6/2019 | Brown et al. | |
| 10,351,545 B2 | 6/2019 | Brown et al. | |
| 10,385,039 B2 | 8/2019 | Brown et al. | |
| 10,413,553 B2 | 9/2019 | Congreve et al. | |
| 10,428,088 B2 | 10/2019 | Congreve et al. | |
| 10,501,483 B2 | 12/2019 | Dinh et al. | |
| 10,548,884 B2 | 2/2020 | Brown et al. | |
| 10,689,368 B2 | 6/2020 | Brown et al. | |

(Continued)

FOREIGN PATENT DOCUMENTS

| | | |
|---|---|---|
| EA | 002393 | 5/2016 |
| EP | 0034415 | 8/1981 |

(Continued)

OTHER PUBLICATIONS

Great Britain Office Action for Application No. GB1810239.2, dated Jan. 30, 2019, 4 pages.
International Search Report and Written Opinion for Application No. PCT/GB2019/051780, dated Aug. 6, 2019, 16 pages.
U.S. Appl. No. 16/450,261, filed Jun. 24, 2019, U.S. Pat. No. 10,787,447, Issued.
Bakker et al., "First-in-man study to investigate safety, pharmacokinetics and exploratory pharmacodynamics of HTL0018318, a novel M1-receptor partial agonist for the treatment of dementias," British Journal of Clinical Pharmacology, 2021, 87(7):2945-2955.
Bradley et al., "AC-260584, an orally bioavailable M1 muscarinic receptor allosteric agonist, improves cognitive performance in an animal model," Neuropharmacology, 2010, 58(2):365-373.
Broadley et al., "Muscarinic Receptor Agonists and Antagonists," Molecules, 2001, 6:142-193.

(Continued)

*Primary Examiner* — Zinna Northington Davis
(74) *Attorney, Agent, or Firm* — Fish & Richardson P.C.

(57) ABSTRACT

This invention relates to compounds that are agonists of the muscarinic $M_1$ and/or $M_4$ receptor and which are useful in the treatment of diseases mediated by the muscarinic $M_1$ and $M_4$ receptors. Also provided are pharmaceutical compositions containing the compounds and the therapeutic uses of the compounds. Compounds provided are of formula

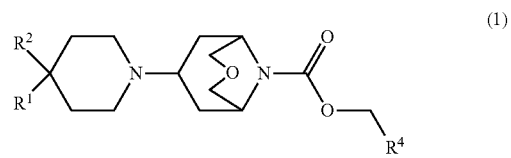

(1)

where Y, $R^1$, $R^2$ and $R^4$ are as defined herein.

10 Claims, No Drawings

(56) References Cited

U.S. PATENT DOCUMENTS

| | | |
|---|---|---|
| 10,738,029 B2 | 8/2020 | Brown et al. |
| 10,752,610 B2 | 8/2020 | Brown et al. |
| 10,759,751 B2 | 9/2020 | Brown et al. |
| 10,787,447 B2 | 9/2020 | Brown et al. |
| 10,858,352 B2 | 12/2020 | Brown et al. |
| 10,961,225 B2 | 3/2021 | Brown et al. |
| 10,973,832 B2 | 4/2021 | Congreve et al. |
| 11,014,880 B2 | 5/2021 | Brown et al. |
| 11,034,704 B2 | 6/2021 | Congreve et al. |
| 11,091,456 B2 | 8/2021 | Brown et al. |
| 11,208,396 B2 | 12/2021 | Brown et al. |
| 11,254,656 B2 | 2/2022 | Brown et al. |
| 11,319,312 B2 | 5/2022 | Brown et al. |
| 11,324,738 B2 | 5/2022 | Brown et al. |
| 11,352,342 B2 | 6/2022 | Brown et al. |
| 2002/0156081 A1 | 10/2002 | Hirst et al. |
| 2003/0225271 A1 | 12/2003 | Emmanuel et al. |
| 2004/0171614 A1 | 9/2004 | Pissarnitski et al. |
| 2005/0085505 A1 | 4/2005 | Best et al. |
| 2005/0085506 A1 | 4/2005 | Pissarnitski et al. |
| 2005/0176703 A1 | 8/2005 | Gabriel et al. |
| 2006/0194844 A1 | 8/2006 | Sugawawa et al. |
| 2006/0276506 A1 | 12/2006 | Yu et al. |
| 2007/0043023 A1 | 2/2007 | Makings et al. |
| 2007/0054911 A1 | 3/2007 | Drutu et al. |
| 2007/0219218 A1 | 9/2007 | Yu et al. |
| 2008/0015179 A1 | 1/2008 | Makings et al. |
| 2009/0076078 A1 | 3/2009 | Cheng et al. |
| 2013/0012485 A1 | 1/2013 | Baeschlin et al. |
| 2014/0329803 A1 | 11/2014 | Congreve et al. |
| 2015/0232443 A1 | 8/2015 | Brown et al. |
| 2015/0376179 A1 | 12/2015 | Livermore et al. |
| 2016/0068508 A1 | 3/2016 | Congreve et al. |
| 2016/0128996 A1 | 5/2016 | Brown et al. |
| 2017/0015650 A1 | 1/2017 | Brown et al. |
| 2017/0037025 A1 | 2/2017 | Brown et al. |
| 2017/0096437 A1 | 4/2017 | Congreve et al. |
| 2017/0157139 A1 | 6/2017 | Congreve et al. |
| 2017/0183338 A1 | 6/2017 | Livermore et al. |
| 2017/0240530 A1 | 8/2017 | Brown et al. |
| 2017/0247369 A1 | 8/2017 | Brown et al. |
| 2018/0022726 A1 | 1/2018 | Brown et al. |
| 2018/0072727 A1 | 3/2018 | Congreve et al. |
| 2018/0105491 A1 | 4/2018 | Brown et al. |
| 2018/0153900 A1 | 6/2018 | Congreve et al. |
| 2018/0155315 A1 | 6/2018 | Brown et al. |
| 2018/0179184 A1 | 6/2018 | Brown et al. |
| 2018/0222885 A1 | 8/2018 | Brown et al. |
| 2018/0228791 A1 | 8/2018 | Brown et al. |
| 2018/0258085 A1 | 9/2018 | Brown et al. |
| 2018/0327426 A1 | 11/2018 | Congreve et al. |
| 2018/0362507 A1 | 12/2018 | Brown et al. |
| 2019/0112294 A1 | 4/2019 | Brown et al. |
| 2019/0202783 A1 | 7/2019 | Brown et al. |
| 2019/0270718 A1 | 9/2019 | Brown et al. |
| 2019/0276437 A1 | 9/2019 | Brown et al. |
| 2019/0337925 A1 | 11/2019 | Brown et al. |
| 2019/0389849 A1 | 12/2019 | Brown et al. |
| 2020/0002328 A1 | 1/2020 | Brown et al. |
| 2020/0017530 A1 | 1/2020 | Congreve et al. |
| 2020/0129496 A1 | 4/2020 | Brown et al. |
| 2020/0165220 A1 | 5/2020 | Brown et al. |
| 2020/0253982 A1 | 8/2020 | Congreve et al. |
| 2020/0290963 A1 | 9/2020 | Brown et al. |
| 2020/0325118 A1 | 10/2020 | Brown et al. |
| 2020/0354339 A1 | 11/2020 | Brown et al. |
| 2021/0040067 A1 | 2/2021 | Brown et al. |
| 2021/0101893 A1 | 4/2021 | Brown et al. |
| 2021/0353637 A1 | 11/2021 | Congreve et al. |
| 2021/0387969 A1 | 12/2021 | Brown et al. |
| 2022/0017504 A1 | 1/2022 | Brown et al. |
| 2022/0048928 A1 | 2/2022 | Congreve et al. |
| 2022/0213034 A1 | 7/2022 | Brown et al. |
| 2022/0298133 A1 | 9/2022 | Brown et al. |
| 2022/0380379 A1 | 12/2022 | Fieldhouse et al. |
| 2023/0002354 A1 | 1/2023 | Brown et al. |

FOREIGN PATENT DOCUMENTS

| | | |
|---|---|---|
| EP | 1221443 | 7/2002 |
| EP | 1647553 | 4/2006 |
| EP | 1679069 | 7/2006 |
| EP | 1900732 | 3/2008 |
| JP | S56110674 | 9/1981 |
| JP | H 11-501014 | 1/1999 |
| JP | 2000-501117 | 2/2000 |
| JP | 2000-502360 | 2/2000 |
| JP | 2003-529546 | 10/2003 |
| JP | 2006-509764 | 3/2006 |
| JP | 2006-516145 | 6/2006 |
| JP | 2006-219480 | 8/2006 |
| JP | 2008-521821 | 6/2008 |
| JP | 2009-527569 | 7/2009 |
| JP | 2013-010719 | 1/2013 |
| JP | 2017-505323 | 2/2017 |
| JP | 2018-508562 | 3/2018 |
| RU | 2323218 | 4/2008 |
| RU | 2008130094 | 1/2010 |
| WO | WO 1994/15928 | 7/1994 |
| WO | WO 1996/13262 | 5/1996 |
| WO | WO 1997/16187 | 5/1997 |
| WO | WO 1998/57641 | 12/1998 |
| WO | WO 1999/32479 | 7/1999 |
| WO | WO 1999/32481 | 7/1999 |
| WO | WO 1999/32486 | 7/1999 |
| WO | WO 1999/32489 | 7/1999 |
| WO | WO 2000/066141 | 11/2000 |
| WO | WO 2000/066559 | 11/2000 |
| WO | WO 2001/027104 | 4/2001 |
| WO | WO 2002/085890 | 10/2002 |
| WO | WO 2003/057672 | 7/2003 |
| WO | WO 2004/014853 | 2/2004 |
| WO | WO 2004/069828 | 8/2004 |
| WO | WO 2004/089942 | 10/2004 |
| WO | WO 2005/037269 | 4/2005 |
| WO | WO 2005/077369 | 8/2005 |
| WO | WO 2006/058294 | 6/2006 |
| WO | WO 2006/068904 | 6/2006 |
| WO | WO 2006/105035 | 10/2006 |
| WO | WO 2007/076070 | 7/2007 |
| WO | WO 2007/079164 | 7/2007 |
| WO | WO 2007/100664 | 9/2007 |
| WO | WO 2007/100670 | 9/2007 |
| WO | WO 2008/021375 | 2/2008 |
| WO | WO 2008/077597 | 7/2008 |
| WO | 2008/117229 A1 | 10/2008 |
| WO | WO 2009/034380 | 3/2009 |
| WO | WO 2010/049146 | 5/2010 |
| WO | WO 2010/070032 | 6/2010 |
| WO | WO 2010/121046 | 10/2010 |
| WO | WO 2010/130945 | 11/2010 |
| WO | WO 2011/112825 | 9/2011 |
| WO | WO 2011/133750 | 10/2011 |
| WO | WO 2011/137012 | 11/2011 |
| WO | WO 2011/143057 | 11/2011 |
| WO | WO 2011/150183 | 12/2011 |
| WO | WO 2012/037393 | 3/2012 |
| WO | WO 2012/125661 | 9/2012 |
| WO | WO 2013/072705 | 5/2013 |
| WO | 2014/045031 A1 | 3/2014 |
| WO | WO 2014/122474 | 8/2014 |
| WO | WO 2015/118342 | 8/2015 |
| WO | 2015/140559 A1 | 9/2015 |
| WO | WO 2016/128990 | 8/2016 |
| WO | 2016/147011 A1 | 9/2016 |
| WO | 2017/021728 A1 | 2/2017 |
| WO | 2017/021729 A1 | 2/2017 |
| WO | 2017/021730 A1 | 2/2017 |
| WO | 2017/077292 A1 | 5/2017 |
| WO | 2018/069732 A1 | 4/2018 |
| WO | WO 2018/229511 | 12/2018 |
| WO | WO 2019/243850 | 12/2019 |

(56) References Cited

FOREIGN PATENT DOCUMENTS

| WO | WO 2020/115505 | 6/2020 |
|----|----------------|--------|
| WO | WO 2020/115506 | 6/2020 |
| WO | WO 2022/129951 | 6/2022 |
| WO | WO 2022/189366 | 9/2022 |

OTHER PUBLICATIONS

Cao et al., "Synthesis and Biological and Characterization of 1-methyl-1,2,5,6-tetrahydropyridy-1,2,5-thiadiazole Derivatives as Muscarinic agonists for treatment of Neurological Disorders," J Med Chem., 2003, 46(20):4273-4286.

Chapman et al., "The muscarinic M4 receptor is the functionally predominant subtype in rat and mouse striatum as demonstrated using [35S] GTPgammaS binding," European Journal of Pharmacology, 2011, 652:1-6.

Chung, "Aberrant phosphorylation in the pathogenesis of Alzheimer's disease," BMB reports, 2009, 42(8):467-474.

cnn.com [Online], "FDA panel backs late-stage Alzheimer's drug," available on or before Oct. 2, 2003 via Internet Archive: Wayback Machine URL<http://web.archive.org/web/20031002091517/http://www.cnn.com:80/2003/HEALTH/conditions/09/24/alzheimers.drug.ap/index.html>, retrieved on Oct. 21, 22, URL<http://www.cnn.com/2003/HEALTH/conditions/09/24/alzheimers.drug.ap/index.html>, 3 pages.

Conn et al., "Subtype-selective allosteric modulators of muscarinic receptors for the treatment of CNS disorders," Trends in Pharmacological Sciences, 2009, 30(3):148-155.

Fisher, "Cholinergic modulation of amyloid precursor protein processing with emphasis on M 1 muscarinic receptor: perspectives and challenges in treatment of Alzheimer's disease," J Neurochem., 2012, 120(Suppl. 1):22-33.

Foley et al., "The 5-HT(6) receptor antagonist SB-271046 reverses scopolamine-disrupted consolidation of a passive avoidance task and ameliorates spatial task deficits in aged rats," Neuropsychopharmacology, 2004, 29(1):93-100.

Foster et al., "Activation of M1 and M4 muscarinic receptors as potential treatments for Alzheimer's disease and schizophrenia," Neuropsychiatric Disease and Treatment, 2014, 10:183-191.

Gilles et al., "Pharmacological models in Alzheimer's disease research," Dialogues in Clinical Neuroscience, 2000, 2(3):247-255.

Hackam et al., "Translation of research evidence from animals to humans," JAMA, 2006, 296(14):1731-1732.

Hasselmo et al., "Modes and Models of Forebrain Cholinergic Neuromodulation of Cognition," Neuropsychopharmacology Reviews, 2011, 36:52-73.

Jordan, "Tamoxifen: a most unlikely pioneering medicine," Nat Rev Drug Discov., 2003, 2(3):205-213.

Jorden, "World Alzheimer Day: French Doctor Denounces Routine Alzheimer Medications," ZCommunications, retrieved on Dec. 20, 2015, retrieved from URL <https://zcomm.org/znetarticle/world-alzheimer-day-french-doctor-denounces-routine-alzheimer-medications/>, 4 pages.

Katz et al., "Transition from acute to chronic postsurgical pain: risk factors and protective factors," Expert Rev Neurother., May 2009, 9(5):723-744.

Kuduk et al., "Novel M1 allosteric ligands: a patent review," Expert Opin Ther Patents., 2012, 22(12):1385-1398.

Lankin et al., "Protonated 3-fluoropiperidines: an unusual fluoro directing effect and a test for quantitative theories of solvation," J. Am. Chem. Soc., 1993, 115(8):3356-3357.

Lee et al., "Amyloid-beta in Alzheimer disease: the null versus the alternate hypotheses," J Pharmacol Exp Ther., Jun. 2007, 321(3):823-829.

Levey, "Muscarine acetylchloline receptor expression in memory circuits:implications for the treatment of Alzheimer disease," PNAS, 1996, 93(24):13541-13546.

Lima et al., "Bioisosterism: A Useful Strategy for Molecular Modification and Drug Design," Curr Med Chem., 2005, 12:23-49.

Martino et al., "The M1/M4 preferring agonist xanomeline is analgesic in rodent models of chronic inflammatory and neuropathic pain via central site of action," Pain, 2011, 152:2852-2860.

Meanwell, "Synopsis of Some Recent Tactical Application of Bioisosteres in Drug Design," J Med Chem., 2011, 54(8):2529-2591.

Melancon et al., "Continued optimization of the MLPCN probe ML071 into highly potent agonists of the hM1 muscarinic acetylcholine receptor," Bioorg Med Chem Lett., May 15, 2012, 22(10):3467-3472.

Nirogi et al., "Synthesis and SAR of Imidazo[1,5-a]pyridine derivatives as 5-HT4 receptor partial agonists for the treatment of cognitive disorders associated with Alzheimer's disease," European Journal of Medicinal Chemistry, 2015, 103:289-301.

Osatuke et al., "Insight in schizophrenia: a review of etiological models and supporting research," Compr. Psychiatry, Jan.-Feb. 2008, 49(1):70-77.

Scarr, "Muscarinic receptors: their roles in disorders of the central nervous system and potential as therapeutic targets," CNS Neuroscience & Therapeutics, 2012, 18:369-379.

Snyder et al., "The Unexpected Diaxial Orientation of cis-3,5-Difluoropiperidine in Water: A Potent CF—NH Charge-Dipole Effect," J. Am. Chem. Soc., 2000, 122(3):544-545.

Tasker et al., "P110—Single and Multiple Dose Safety, Tolerability and Pharmacokinetics of the Selective M1 Receptor Partial Agonist HTL0018318 in Healthy Volunteers," The Journal of Prevention of Alzheimer's Disease, 2018, 5(1):S64-S65.

Tasker et al., "Single and multiple dose safety, tolerability and pharmacokinetics of the selective M1 receptor partial agonist HTL0018318 in healthy volunteers," Poster Presentation, Sosei Heptares, Nov. 2018, 2 pages.

Tecle et al., "Design and Synthesis of m1-Selective Muscarinic Agonists: (R)-(-)-(Z)-1-Azabicyclo[2.2.1 ]heptan-3-one, O-(3-(3'-Methoxyphenyl)-2-propynyl)-oxime Maleate (CI-1017), a Functionally m1-Selective Muscarinic Agonist," J Med Chem., 1998, 41(14):2524-2536.

Tietje et al., "Preclinical Characterization of A-582941: A Novel α7 Neuronal Nicotinic Receptor Agonist with Broad Spectrum Cognition-Enhancing Properties," CNS Neuroscience & Therapeutics, 2008, 14:65-82.

Toja et al., "1-Alkyl-1,2,5,6-tetrahydropyridine-3-carboxaldehyde-0-alkyl-oximes. a new class of potent orally active muscarinic agonists related to arecoline," Eur J Med Chem, 1991, 26:853-868.

Venkatesh et al., "Role of the development scientist in compound lead selection and optimization," J Pharm Sci., 2000, 89:145-154.

Chakraburtty, "Psychotic Disorders: Types of Mental Illnesses," MedicineNet.com, Feb. 1, 2007, 5 pages.

Chen et al., "Animal models of Alzheimer's disease: Applications, evaluation, and perspectives," Zoological Research, 2022, 43(6):1026-1040.

PHARMACEUTICAL COMPOUNDS

This application is a continuation of U.S. patent application Ser. No. 16/450,261, filed Jun. 24, 2019, which claims benefit of GB Application No.: 1810239.2, filed Jun. 22, 2018. These applications are herein incorporated by reference.

This invention relates to a class of novel bridged morpholine compounds, their salts, pharmaceutical compositions containing them and their use in therapy of the human body. In particular, the invention is directed to a class of compounds, which are agonists of the muscarinic $M_1$ and/or $M_4$ receptors, and hence are useful in the treatment of Alzheimer's disease, schizophrenia, cognitive disorders and other diseases mediated by the muscarinic $M_1/M_4$ receptors, as well as the treatment or alleviation of pain.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 *Science*). In schizophrenia, which is also characterised by cognitive impairments, mAChR density is reduced in the pre-frontal cortex, hippocampus and caudate putamen of schizophrenic subjects (Dean et al., 2002 *Mol Psychiatry*). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting. (www.drugs.com/pro/donepezil.html; www.drugs.com/pro/rivastigmine.html). Further discovery efforts have targeted the identification of direct $M_1$ mAChR agonists to target increases in cognitive function. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, non-amyloidgenic and amyloidgenic. Cleavage of APP by γ-secretase is common to both pathways, but in the former APP is cleaved by an α-secretase to yield soluble APPα. The cleavage site is within the Aβ sequence, thereby precluding its formation. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3xTgAD transgenic mouse, a model of the different components of Alzheimer's disease (Caccamo et al., 2006 *Neuron*). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*). Muscarinic receptors have also been implicated in the neurobiology of addiction. The reinforcing effects of cocaine and other addictive substances are mediated by the mesolimbic dopamine system where behavioural and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3): 367-78). Furthermore xanomeline has been demonstrated to block the effects of cocaine in these models. Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 *Arch Neurol*). This compound was also assessed in a small Phase II study of schizophrenics and gave a significant reduction in positive and negative symptoms when compared to placebo control (Shekhar et al., 2008 *Am J Psych*). However, in all clinical studies xanomeline and other related mAChR agonists have displayed an unacceptable safety margin with respect to cholinergic side effects, including nausea, gastrointestinal pain, diarrhoea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 *Bioorg Med Chem Lett*; Johnson et al., 2010 *Bioorg Med Chem Lett*; Budzik et al., 2010 *ACS Med Chem Lett*). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

The Invention

The present invention provides compounds having activity as muscarinic $M_1$ and/or $M_4$ receptor agonists. More particularly, the invention provides compounds that exhibit selectivity for the $M_1$ or $M_4$ receptor relative to the $M_2$ and $M_3$ receptor subtypes. Accordingly, in a first embodiment (Embodiment 1.1), the invention provides a compound of the formula (1):

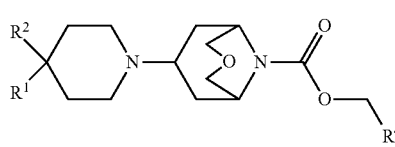

(1)

or a salt thereof, wherein:

$R^1$ is selected from $NR^5R^6$; $CONR^8R^9$; an optionally substituted 5- or 6-membered ring containing 0, 1, 2 or 3 heteroatoms selected from O, N and S and oxidized forms thereof; or $R^1$ is linked to $R^2$ to form an optionally substituted spirocyclic group;

$R^2$ is selected from hydrogen; fluorine; cyano; hydroxy; amino; and a $C_{1-3}$ non-aromatic hydrocarbon group which is optionally substituted with one to six fluorine atoms and wherein one of the carbon atoms of the hydrocarbon group may optionally be replaced by a heteroatom selected from O, N and S and oxidized forms thereof, or $R^2$ is linked to $R^1$ to form an optionally substituted spirocyclic group;

$R^4$ is H or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$ is $COR^7$, a non-aromatic $C_{1-6}$ hydrocarbon group optionally substituted with one or more fluorine atoms or optionally substituted with a 5- or 6-membered ring containing 0, 1, 2 or 3 heteroatoms selected from O, N and S and oxidized forms thereof, or $R^5$ can be joined together with $R^6$ to form an optionally substituted monocyclic or bicyclic ring containing 0, 1, 2 or 3 heteroatoms selected from O, N and S and oxidized forms thereof, $R^6$ is hydrogen, a non-aromatic $C_{1-6}$ hydrocarbon group optionally substituted with one or more fluorine atoms or optionally substituted with a 5- or 6-membered optionally substituted ring containing 0, 1, 2 or 3 heteroatoms selected from O, N and S and oxidized forms thereof, or $R^6$ can be joined together with $R^5$ or $R^7$ to form an optionally substituted monocyclic or bicyclic ring containing 0, 1, 2 or 3 heteroatoms selected from O, N and S and oxidized forms thereof, $R^7$ is a non-aromatic $C_{1-6}$ hydrocarbon group optionally substituted with one or more fluorine atoms, or $R^7$ can be joined together with $R^6$ to form an optionally substituted monocyclic or bicyclic ring containing 0, 1, 2 or 3 heteroatoms selected from O, N and S and oxidized forms thereof, $R^9$ is hydrogen, a non-aromatic $C_{1-6}$ hydrocarbon group optionally substituted with one or more fluorine atoms, or $R^9$ can be joined together with $R^9$ to form an optionally substituted monocyclic or bicyclic ring containing 0, 1, 2 or 3 heteroatoms selected from O, N and S and oxidized forms thereof, and $R^9$ is a non-aromatic $C_{1-6}$ hydrocarbon group optionally substituted with one or more fluorine atoms, or $R^9$ can be joined together with $R^9$ to form an optionally substituted monocyclic or bicyclic ring containing 0, 1, 2 or 3 heteroatoms selected from O, N and S and oxidized forms thereof.

Particular compounds of the formula (1) are as further defined in the following Embodiments:

1.2. A compound according to Embodiment 1.1 wherein $R^1$ is $NR^5R^6$; $CONR^8R^9$; an optionally substituted 5- or 6-membered ring containing 1 or 2 heteroatoms selected from O or N; or $R^1$ is linked to $R^2$ to form an optionally substituted spirocyclic ring having 3, 4 or 5 atoms containing 0, 1 or 2 heteroatoms selected from O or N.

1.3 A compound according to Embodiment 1.2 wherein $R^1$ is $NR^5R^6$ or $CONR^8R^9$.

1.4 A compound according to Embodiment 1.2 wherein $R^1$ is linked to $R^2$ to form an optionally substituted spirocyclic ring having 3, 4 or 5 atoms containing 0, 1 or 2 heteroatoms selected from O or N.

1.5. A compound according to Embodiment 1.4 wherein $R^1$ is linked to $R^2$ to form an optionally substituted spirocyclic ring having 3, 4 or 5 atoms containing 0, 1 or 2 heteroatoms selected from O or N, wherein the optional substituents are selected from $C_1$-$C_3$ alkyl, $C_1$-$C_3$ alkoxy, halogen, cyano, oxo, hydroxyl or amino or a further fused ring.

1.6. A compound according to Embodiment 1.2 wherein $R^1$ is an optionally substituted 5- or 6-membered ring containing 1 or 2 heteroatoms selected from O or N.

1.7. A compound according to Embodiment 1.6 wherein $R^1$ is an optionally substituted 5- or 6-membered aromatic ring containing 1 or 2 nitrogen heteroatoms.

1.8. A compound according to Embodiment 1.6 or Embodiment 1.7 wherein $R^1$ is an optionally substituted 5- or 6-membered aromatic ring containing 1 or 2 nitrogen heteroatoms, wherein the optional substituents are selected from $C_1$-$C_3$ alkyl, $C_1$-$C_3$ alkoxy, halogen, cyano, oxo, hydroxyl or amino.

1.9. A compound according to any one of Embodiments 1.1 to 1.8 wherein $R^5$ is selected from $COR^7$, a non-aromatic $C_{1-6}$ hydrocarbon group optionally substituted with a 6 membered aromatic ring containing 0, 1, or 2 nitrogen heteroatoms, or $R^5$ can be joined together with $R^6$ to form an optionally substituted monocyclic or bicyclic ring containing 0, 1, 2 or 3 heteroatoms selected from O, N and S and oxidized forms thereof, or $R^7$ can be joined together with $R^6$ to form an optionally substituted monocyclic or bicyclic ring containing 0, 1, 2 or 3 heteroatoms selected from O, N and S and oxidized forms thereof.

1.10. A compound according to Embodiment 1.9 wherein $R^5$ is $COCH_3$, a non-aromatic $C_{1-6}$ hydrocarbon group or $R^5$ can be joined together with $R^6$ to form an optionally substituted monocyclic ring or $R^5$ is $COR^7$ where $R^7$ can be joined together with $R^6$ to form an optionally substituted monocyclic ring.

1.11. A compound according to Embodiment 1.10 wherein $R^5$ is $COCH_3$, a non-aromatic $C_{1-6}$ hydrocarbon group or $R^5$ can be joined together with $R^6$ to form an optionally substituted monocyclic ring, wherein the optional substituents are selected from $C_1$-$C_3$ alkyl, $C_1$-$C_3$ alkoxy, halogen, cyano, oxo, hydroxyl or amino, wherein the $C_1$-$C_3$ alkyl or $C_1$-$C_3$ alkoxy groups can have an optional substituent selected from halogen, cyano, oxo, hydroxyl or amino, or $R^5$ is $COR^7$ where $R^7$ can be joined together with $R^6$ to form an optionally substituted monocyclic ring, wherein the optional substituents are selected from $C_1$-$C_3$ alkyl, $C_1$-$C_3$ alkoxy, halogen, cyano, oxo, hydroxyl or amino, wherein the $C_1$-$C_3$ alkyl or $C_1$-$C_3$ alkoxy groups can have an optional substituent selected from halogen, cyano, oxo, hydroxyl or amino.

1.12. A compound according to any one of Embodiments 1.1 to 1.11 wherein $R^6$ is selected from hydrogen, a non-aromatic $C_{1-6}$ hydrocarbon group optionally substituted with a 6-membered optionally substituted aromatic ring containing 0, 1, or 2 nitrogen heteroatoms, or $R^6$ can be joined together with $R^5$ or $R^7$ to form an optionally substituted monocyclic or bicyclic ring containing 0, 1, 2 or 3 heteroatoms selected from O, N and S and oxidized forms thereof.

1.13. A compound according to Embodiment 1.12 wherein $R^6$ is hydrogen, a non-aromatic $C_{1-6}$ hydrocarbon group optionally substituted with an optionally substituted phenyl ring, or $R^6$ can be joined together with $R^5$ or $R^7$ to form an optionally substituted monocyclic ring.

1.14. A compound according to Embodiment 1.13 wherein $R^6$ is hydrogen, a non-aromatic $C_{1-6}$ hydrocarbon group optionally substituted with an optionally substituted phenyl ring, wherein the optional substituents on the phenyl ring are selected from $C_1$-$C_3$ alkyl, $C_1$-$C_3$ alkoxy, halogen, cyano, oxo, hydroxyl or amino, wherein the $C_1$-$C_3$ alkyl or $C_1$-$C_3$ alkoxy groups can have an optional substituent selected from halogen, cyano, oxo, hydroxyl or amino, or $R^6$ can be joined together with $R^5$ or $R^7$ to form an optionally substituted monocyclic ring wherein the optional substituents are selected from $C_1$-$C_3$ alkyl, $C_1$-$C_3$ alkoxy, halogen, cyano, oxo, hydroxyl or amino, wherein the $C_1$-$C_3$ alkyl or $C_1$-$C_3$ alkoxy groups can have an optional substituent selected from halogen, cyano, oxo, hydroxyl or amino.

1.15. A compound according to Embodiment 1.3 wherein $R^8$ is hydrogen, a non-aromatic $C_{1-6}$ hydrocarbon group, or $R^8$ can be joined together with $R^9$ to form an optionally substituted monocyclic ring, wherein the optional substituents are selected from $C_1$-$C_3$ alkyl, $C_1$-$C_3$ alkoxy, halogen, cyano, oxo, hydroxyl or amino.

1.16. A compound according to Embodiment 1.3 wherein $R^9$ is a non-aromatic $C_{1-6}$ hydrocarbon group, or $R^9$ can be joined together with $R^8$ to form an optionally substituted monocyclic ring wherein the optional substituents are selected from $C_1$-$C_3$ alkyl, $C_1$-$C_3$ alkoxy, halogen, cyano, oxo, hydroxyl or amino.

1.17. A compound according to any one of Embodiments 1.1 to 1.16 being a compound of the formula (1):

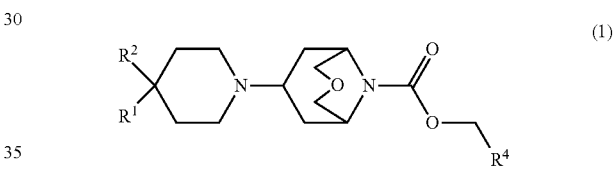

or a salt thereof, wherein:

$R^1R^2$ is selected from:

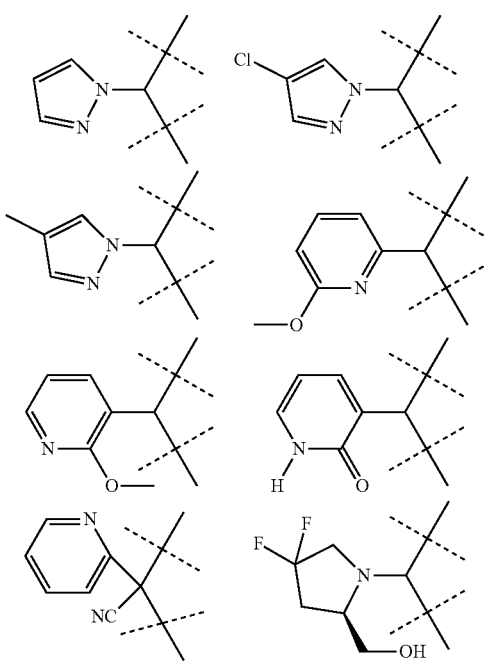

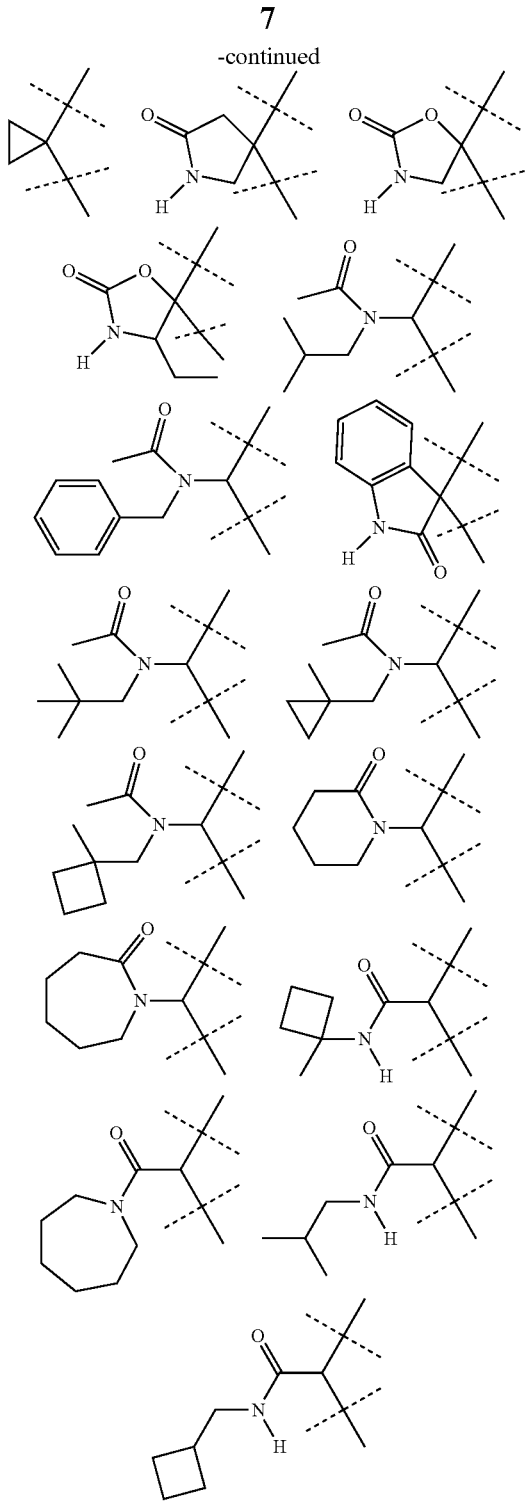

1.18. A compound according to any one of Embodiments 1.1 to 1.17 wherein $R^4$ is H or an acyclic $C_{1-4}$ hydrocarbon group optionally substituted with one or more fluorine atoms.

1.19. A compound according to Embodiment 1.18 wherein $R^4$ is H or an acyclic $C_{1-3}$ hydrocarbon group optionally substituted with one or more fluorine atoms.

1.20. A compound according to Embodiment 1.19 wherein $R^4$ is H or a $C_{1-3}$ alkyl group or a $C_{1-2}$ alkynyl group.

1.21 A compound according to Embodiment 1.20 wherein $R^4$ is selected from H, methyl, fluoromethyl, ethyl, ethynyl and 1-propynyl.

1.22 A compound according to Embodiment 1.21 wherein $R^4$ is methyl.

1.23 A compound according to Embodiment 1.21 wherein $R^4$ is H.

1.24 A compound according to Embodiment 1.1 which is as defined in any one of Examples 1-1 to 8-25.

1.25 A compound according to any one of Embodiments 1.1 to 1.24 having a molecular weight of less than 550, for example less than 500, or less than 450.

1.26 A compound according to any one of Embodiments 1.1 to 1.25 which is in the form of a salt.

1.27 A compound according to Embodiment 1.26 wherein the salt is an acid addition salt.

1.28 A compound according to Embodiment 1.26 or Embodiment 1.27 wherein the salt is a pharmaceutically acceptable salt.

Definitions

In this application, the following definitions apply, unless indicated otherwise.

The term "treatment", in relation to the uses of the compounds of the formula (1) is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" (as in "$C_{1-5}$ non-aromatic hydrocarbon group" or "acyclic $C_{1-5}$ non-aromatic hydrocarbon group") refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" and "cycloalkenyl" are used in their conventional sense (e.g. as defined in the IUPAC Gold Book) unless indicated otherwise. The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^4$, $R^5$, $R^6$, $R^7$, $R^8$ and $R^9$ above, where stated, one or two but not all, carbon atoms of the non-aromatic hydrocarbon group may optionally be replaced by a heteroatom selected from O, N and S and oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—S(O)$_2$—$CH_2$—, replacement of a carbon atom in a —$CH_2$—$CH_2$—$CH_2$— chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1) can exist in the form of salts, for example acid addition salts or, in certain cases salts of organic and inorganic bases such as carboxylate, sulfonate and phosphate salts. All such salts are within the scope of this invention, and references to compounds of the formula (1) include the salt forms of the compounds as defined in Embodiments 1.26 to 1.28.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.27) may be formed with a wide variety of acids, both inorganic and organic. Examples of acid addition salts falling within Embodiment 1.27 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1 S)-camphor-10-sulfonic, capric, caproic, caprylic, cinnamic, citric, cyclamic, dodecylsulfuric, ethane-1,2-disulfonic, ethane-sulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) contain an amine function, these may form quaternary ammonium salts (Embodiment 1.29), for example by reaction with an alkylating agent according to methods well known to the skilled person. Such quaternary ammonium compounds are within the scope of formula (1).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.30), the invention provides a geometric isomer of a compound according to any one of Embodiments 1.1 to 1.29.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.31) the invention provides a compound according to any one of Embodiments 1.1 to 1.30 which contains a chiral centre. The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, $4^{th}$ Edition, John Wiley & Sons, New York, 1992, pages 109-114, and see also Cahn, Ingold & Prelog, *Angew. Chem. Int. Ed. Engl.,* 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.32), the invention provides compositions containing a compound according to Embodiment 1.31 having one or more chiral centres, wherein at least 55% (e.g. at least 60%, 65%, 70%, 75%, 80%, 85%, 90% or 95%) of the compound of Embodiment 1.31 is present as a single optical isomer (e.g. enantiomer or diastereoisomer).

In one general embodiment (Embodiment 1.33), 99% or more (e.g. substantially all) of the total amount of the compound (or compound for use) of Embodiment 1.31 is present as a single optical isomer.

For example, in one embodiment (Embodiment 1.34) the compound is present as a single enantiomer.

In another embodiment (Embodiment 1.35), the compound is present as a single diastereoisomer.

The invention also provides mixtures of optical isomers, which may be racemic or non-racemic. Thus, the invention provides:

1.36 A compound according to Embodiment 1.31 which is in the form of a racemic mixture of optical isomers.

1.37 A compound according to Embodiment 1.31 which is in the form of a non-racemic mixture of optical isomers.

Isotopes

The compounds of the invention as defined in any one of Embodiments 1.1 to 1.37 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.38), the compound of any one of Embodiments 1.1 to 1.37 contains no radioactive isotopes. Such compounds are preferred for therapeutic use. In another embodiment (Embodiment 1.39), however, the compound of any one of Embodiments 1.1 to 1.37 may contain one or more radioisotopes. Compounds containing such radioisotopes may be useful in a diagnostic context.

Solvates

Compounds of the formula (1) as defined in any one of Embodiments 1.1 to 1.39 may form solvates. Preferred solvates are solvates formed by the incorporation into the solid state structure (e.g. crystal structure) of the compounds of the invention of molecules of a non toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.40 and 1.41, the invention provides:

1.40 A compound according to any one of Embodiments 1.1 to 1.39 in the form of a solvate.

1.41 A compound according to Embodiment 1.40 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.42), the invention provides a compound as defined in any one of Embodiments 1.1 to 1.40 in an anhydrous form (e.g. anhydrous crystalline form).

Crystalline and Amorphous Forms

The compounds of any one of Embodiments 1.1 to 1.40 may exist in a crystalline or non crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1). Accordingly, in further embodiments, the invention provides:

1.43 A compound according to any one of Embodiments 1.1 to 1.42 in a crystalline form.

1.44 A compound according to any one of Embodiments 1.1 to 1.42 which is:
(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.45 A compound according to any one of Embodiments 1.1 to 1.42 which is in an amorphous form.

Prodrugs

The compounds of the formula (1) as defined in any one of Embodiments 1.1 to 1.45 may be presented in the form of a pro-drug. By "prodrugs" is meant for example any compound that is converted in vivo into a biologically active compound of the formula (1), as defined in any one of Embodiments 1.1 to 1.45.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.46), the invention provides a pro-drug of a compound as defined in any one of Embodiments 1.1 to 1.45 wherein the compound contains a functional group which is convertible under physiological conditions to form a hydroxyl group or amino group.

Complexes and Clathrates

Also encompassed by formula (1) in Embodiments 1.1 to 1.46 are complexes (e.g. inclusion complexes or clathrates with compounds such as cyclodextrins, or complexes with metals) of the compounds of Embodiments 1.1 to 1.46.

Accordingly, in another embodiment (Embodiment 1.47), the invention provides a compound according to any one of Embodiments 1.1 to 1.46 in the form of a complex or clathrate.

Biological Activity and Therapeutic Uses

The compounds of the present invention have activity as muscarinic $M_1$ and/or $M_4$ receptor agonists. The muscarinic activity of the compounds can be determined using the Phospho-ERK1/2 assay described in Example A below.

A significant advantage of compounds of the invention is that they are highly selective for the $M_1$ and/or $M_4$ receptors relative to the $M_2$ and $M_3$ receptor subtypes. Compounds of the invention are neither agonists nor antagonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 95) against the $M_1$ and/or $M_4$ receptor in the functional assay described in Example A, they may have $pEC_{50}$ values of less than 5 and $E_{max}$ values of less than 20% when tested against the $M_2$ and $M_3$ subtypes in the functional assay of Example A.

Some compounds of the invention have activity at both the $M_1$ and $M_4$ receptors, and some have activity at the $M_4$ receptor.

Accordingly, in Embodiments 2.1 to 2.16, the invention provides:

2.1 A compound according to any one of Embodiments 1.1 to 1.47 for use in medicine.

2.2 A compound according to any one of Embodiments 1.1 to 1.47 for use as a muscarinic $M_1$ and/or $M_4$ receptor agonist.

2.3 A compound according to any one of Embodiments 1.1 to 1.47 which is a muscarinic $M_1$ receptor agonist having a $pEC_{50}$ greater than 6.9 and an $E_{max}$ of at least 80 against the $M_1$ receptor in the assay of Example A herein or an assay substantially similar thereto.

2.4 A compound according to Embodiment 2.3 which is a muscarinic $M_1$ receptor agonist having a $pEC_{50}$ greater than 7.0.

2.5 A compound according to Embodiment 2.3 or Embodiment 2.4 having an $E_{max}$ of at least 90 against the $M_1$ receptor.

2.6 A compound according to any one of Embodiments 1.1 to 1.47 which is a muscarinic $M_1$ and $M_4$ receptor agonist having a $pEC_{50}$ in the range from 6.0 to 7.8 and an $E_{max}$ of at least 70 against the muscarinic $M_1$ and $M_4$ receptors in the assay of Example A herein or an assay substantially similar thereto.

2.7 A compound according to any one of Embodiments 1.1 to 1.47 which is a muscarinic $M_4$ receptor agonist having a $pEC_{50}$ greater than 7.0.

2.8 A compound according to Embodiment 2.6 or Embodiment 2.7 having an $E_{max}$ of at least 90 against the $M_4$ receptor.

2.9 A compound according to any one of Embodiments 1.1 to 1.47 which is a muscarinic $M_4$ receptor agonist having a $pEC_{50}$ in the range from 6.0 to 7.8 and an $E_{max}$ of at least 70 against the muscarinic $M_4$ receptor in the assay of Example A herein or an assay substantially similar thereto.

2.10 A compound according to any one of Embodiments 2.3 to 2.9 which is selective for the $M_1$ and $M_4$ receptor compared to the muscarinic $M_2$ and $M_3$ receptors.

2.11 A compound according to Embodiment 2.9 which is selective for the $M_4$ receptor compared to the muscarinic $M_2$ and $M_3$ receptors.

2.12 A compound according to any one of Embodiments 2.3 to 2.5 which is selective for the $M_1$ receptor compared to the muscarinic $M_2$, $M_3$ and $M_4$ receptors.

2.13 A compound according to any one of Embodiments 2.7 or 2.9 which is selective for the $M_4$ receptor compared to the muscarinic $M_1$, $M_2$ and $M_3$ receptors.

2.14 A compound according to any one of Embodiments 2.3 to 2.13 which has a $pEC_{50}$ of less than 5 and an $E_{max}$ of less than 50 against the muscarinic $M_2$ and $M_3$ receptor subtypes.

2.15 A compound according to Embodiment 2.14 which has a $pEC_{50}$ of less than 4.5 and/or an $E_{max}$ of less than 30 against the muscarinic $M_2$ and $M_3$ receptor subtypes.

2.16 A compound according to any one of Embodiments 1.1 to 1.47 and Embodiments 2.3 to 2.15 for use in the treatment of a disease or condition mediated by the muscarinic $M_1$ and/or $M_4$ receptors.

By virtue of their muscarinic $M_1$ and/or $M_4$ receptor agonist activity, compounds of the invention can be used in the treatment of Alzheimer's disease, schizophrenia and other psychotic disorders, cognitive disorders and other diseases mediated by the muscarinic $M_1$ and/or $M_4$ receptor, and can also be used in the treatment of various types of pain. Accordingly, in Embodiments 2.17 to 2.38, the invention provides:

2.17 A compound according to any one of Embodiments 1.1 to 1.47 for use in the treatment of a cognitive disorder or psychotic disorder.

2.18 A compound for use in according to Embodiment 2.17 wherein the cognitive disorder or psychotic disorder comprises, arises from or is associated with a condition selected from cognitive impairment, Mild Cognitive Impairment (including mild cognitive impairment due to Alzhimer's disease and/or prodromal Alzheimer's disease), fronto-temporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease (including prodromal Alzheimer's disease and stages 1, 2, and 3 early Alzheimer's disease as defined by the US Food and Drug Admistration's "Early Alzheimer's disease: Developing Drugs for Treatment" available at fda.gov/downloads/Drugs/GuidanceComplianceRegulatorylnformation/Guidances/UCM5967 28.pdf), progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, AIDS-related dementia or other dementia states such as multi-infarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and and schizo-affective disorder.

2.19 A compound according to any one of Embodiments 1.1 to 1.47 for use in the treatment of Alzheimer's disease or dementia with Lewy bodies.

2.20 A compound according to any one of Embodiments 1.1 to 1.47 for use in the treatment of Schizophrenia.

2.21 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.47.

2.22 A method according to Embodiment 2.21 wherein the cognitive disorder comprises, arises from or is associated with a condition as defined in Embodiment 2.18.

2.23 A method according to Embodiment 2.22 wherein the cognitive disorder arises from or is associated with Alzheimer's disease or dementia with Lewy bodies.

2.24 A method according to Embodiment 2.22 wherein the cognitive disorder is Schizophrenia.

2.25 The use of a compound according to any one of Embodiments 1.1 to 1.47 for the manufacture of a medicament for the treatment of a cognitive disorder.

2.26 The use according to Embodiment 2.25 wherein the cognitive disorder comprises, arises from or is associated with a condition as defined in Embodiment 2.18.

2.27 The use according to Embodiment 2.26 wherein the cognitive disorder arises from or is associated with Alzheimer's disease or dementia with Lewy bodies.

2.28 The use according to Embodiment 2.26 wherein the cognitive disorder is Schizophrenia.

2.29 A compound according to any one of Embodiments 1.1 to 1.47 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.30 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.47.

2.31 A compound according to any one of Embodiments 1.1 to 1.47 for the treatment of peripheral disorders such as reduction of intra ocular pressure in Glaucoma and treatment of dry eyes and dry mouth including Sjogren's Syndrome.

2.32 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.47.

2.33 The use of a compound according to any one of Embodiments 1.1 to 1.47 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.34 The use of a compound according to any one of Embodiments 1.1 to 1.47 for the use in the treatment of skin lesions for example due to pemphigus vulgaris, dermatitis herpetiformis, pemphigoid and other blistering skin conditions.

2.35 The use of a compound according to any one of Embodiments 1.1 to 1.47 for the use in treating, preventing, ameliorating or reversing conditions associated with altered gastro intestinal function and motility such as functional dyspepsia, irritable bowel syndrome, gastroesophageal acid reflux (GER) and esophageal dysmotility, symptoms of gastroparesis and chronic diarrhoea.

2.36 The use of a compound according to any one of Embodiments 1.1 to 1.47 for the use in in the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

2.37 The use of a compound according to any one of Embodiments 1.1 to 1.47 for the treatment of addiction.

2.38 The use of a compound according to any one of Embodiments 1.1 to 1.47 for the treatment of movement disorders such as Parkinson's disease, ADHD, Huntingdon's disease, tourette's syndrome and other syndromes associated with dopaminergic dysfunction as an underlying pathogenetic factor driving disease.

2.39 The use of a compound according to any one of Embodiments 1.1 to 1.47 for the treatment of behavioural and psychological symptoms of dementia (BPSD; including agitation, verbal aggressiveness, physical aggressiveness, depression, anxiety, abnormal motor behaviour, elated mood, irritablility, apathy, disinhibition, impulsivity. delusions, hallucinations, sleep changes, and appetite changes).

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.47, which process comprises:

(A) the reaction of a compound of the formula (10):

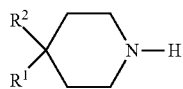

(10)

with a compound of the formula (11):

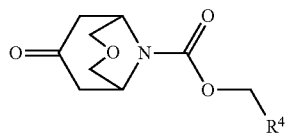

(11)

under reductive amination conditions; wherein $R^1$, $R^2$ and $R^4$ are as defined in any one of Embodiments 1.1 to 1.47; or B) the reaction of a compound of the formula (12):

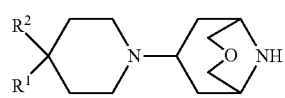

(12)

with a compound of the formula LG-C(=O)—O—CH$_2$—R$^4$; wherein $R^1$, $R^2$ and $R^4$ are as defined in any one of Embodiments 1.1 to 1.47 and LG represents a suitable leaving group such as Cl, 1-imidazole or 4-nitrophenol; or (C) when it is required to prepare a compound of formula (1) wherein $R^1$ comprises CONR$^8$R$^9$:

the reaction of a compound of the formula (13):

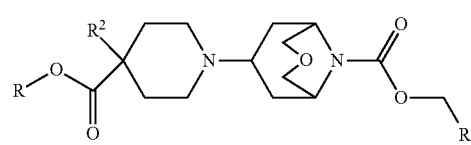

(13)

with an amine of the formula R$^8$R$^9$NH; wherein R represents a suitable group such as methyl- or ethyl- and $R^2$, $R^4$, $R^8$ and $R^9$ are as defined in any one of Embodiments 1.1 to 1.47; or (D) when it is required to prepare a compound of formula (1) wherein $R^1$ comprises CONR$^8$R$^9$:

the reaction of a compound of the formula (14):

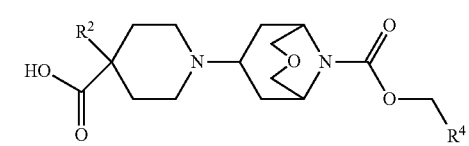

(14)

with an amine of the formula R$^8$R$^9$NH; wherein $R^2$, $R^4$, $R^8$ and $R^9$ are as defined in any one of Embodiments 1.1 to 1.47;

and optionally:

(E) converting one compound of the formula (1) to another compound of the formula (1).

In process variant (A), the ketone (11) is reacted with the amine (10) under reductive amination conditions. The reductive amination reaction is typically carried out at ambient temperature to mild heating (e.g. at a temperature of about 20° C. to about 70° C.) using a borohydride reducing agent such as sodium triacetoxy-borohydride (STAB) in a solvent such as dichloromethane (DCM), dichloroethane (DCE), N,N-dimethylformamide (DMF) or methanol (MeOH) containing an acid such as acetic acid (AcOH) or trifluoroacetic acid (TFA), or sodium cyanoborohydride (NaCNBH$_3$) in combination with zinc chloride (ZnCl$_2$) in a solvent such as MeOH, or STAB in a solvent such as DCM or DCE containing an acid such as AcOH or TFA in combination with titanium tetraisopropoxide (Ti(O$^i$Pr)$_4$). Optionally, the amine (10) may be present in the reaction as an acid salt such as a hydrogen chloride (HCl), hydrogen bromide (HBr) or a TFA salt, optionally in the presence of a tertiary base such as triethylamine (TEA) or N,N-diisopropylamine (DIPEA).

Amines of the formula (10) may be sourced commercially or may be prepared by a variety of different methods that exist in the art and that are well known to the skilled person. For example, when it is required to prepare a compound of formula (1) wherein $R^1$ comprises an optionally substituted 5- or 6-membered aromatic ring and $R^2$ is hydrogen, amines of the formula (10) can be prepared by the sequence of reactions shown in Scheme 1 below:

Scheme 1

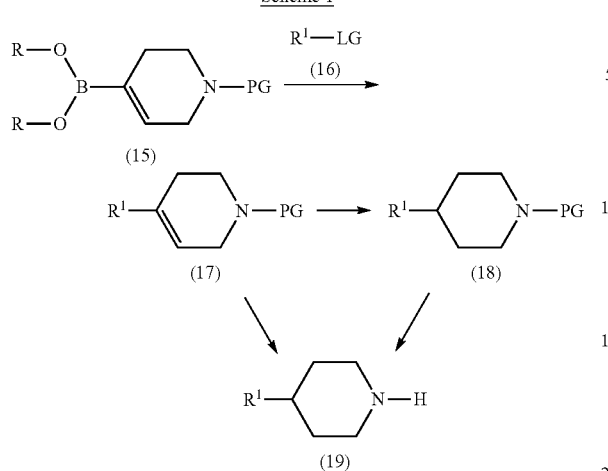

Thus, a compound of formula (15), wherein R is hydrogen, or the two R groups are joined together as —C(CH$_3$)$_2$—C(CH$_3$)$_2$—, and PG represents a suitable protecting group such as tert-butyloxycarbonyl (BOC), benzyloxy carbonyl (CBZ) or benzyl (Bn), can be reacted with a compound of formula (16), wherein R$^1$ is an optionally substituted 5- or 6-membered aromatic ring and LG represents a suitable leaving group such as halogen (e.g. iodide, bromide or chloride) or a sulphonic acid ester (e.g. a tosylate, mesylate or triflate), under suitable palladium catalyzed 'Suzuki' coupling conditions that are well known to the skilled person, to form a compound of formula (17). For example, suitable palladium catalyzed coupling conditions might comprise reaction with a suitable catalyst such as palladium(II) acetate (Pd(OAc)$_2$), tetrakis(triphenylphosphine)palladium(0) (Pd(Ph$_3$)$_4$), tris(dibenzylideneacetone)dipalladium(0) (Pd$_2$(dba)$_3$), or (1,1'-bis(diphenylphosphino)ferrocene)palladium(II) dichloride (Pd(dppf)Cl$_2$) optionally in the presence of a suitable ligand such as tricyclohexylphosphine (P(Cy)$_3$), 2-dicyclohexylphosphino-2',4',6'-triisopropylbiphenyl (XPhos), 2-dicyclohexylphosphino-2',6'-diisopropoxybiphenyl (RuPhos) or 4,5-bis(diphenylphosphino)-9,9-dimethylxanthene (Xantphos), in the presence of a suitable base such as potassium carbonate (K$_2$CO$_3$), potassium phosphate (K$_3$PO$_4$), potassium tert-butoxide (KO$^t$Bu), potassium acetate (KOAc), sodium carbonate (Na$_2$CO$_3$) or cesium carbonate (Cs$_2$CO$_3$), in a suitable solvent such as benzene, toluene, tetrahydrofuran (THF), 1,4-dioxane, H$_2$O, ethanol (EtOH) or DMF, or a mixture of two or more of the aforementioned solvents, at a temperature of about room temperature to about 150° C., optionally using a sealed vessel under a reaction pressure greater than atmospheric pressure, optionally using conventionally heating or microwave heating. Once formed, the compound of formula (17) can be reduced using suitable hydrogenation conditions to form a compound of formula (18). Suitable hydrogenation conditions might be reaction with hydrogen (H$_2$) in the presence of a palladium on carbon (Pd/C) catalyst in a suitable solvent such as EtOH or MeOH at a temperature of about 20° C. to about 80° C. Once formed, the protecting group PG can be removed from the compound of formula (18) using suitable conditions to form amine (19). For example, when the protecting group PG is BOC, then suitable conditions to effect its removal might be reaction with an acid such as HCl in a solvent such as 1,4-dioxane or diethyl ether (Et$_2$O), or TFA in a solvent such as DCM. Alternatively, when the protecting group PG is CBZ or Bn, then amine (19) can be formed directly from the compound of formula (17) in one step by using suitable hydrogenation conditions such as reaction with H$_2$ in the presence of a Pd/C or palladium hydroxide on carbon (Pd(OH)$_2$/C) catalyst in a suitable solvent such as EtOH or MeOH at a temperature of about 20° C. to about 80° C.

Alternatively, when it is required to prepare a compound of formula (1) wherein R$^2$ is hydrogen and R$^1$ comprises NR$^6$COR$^7$, wherein R$^6$ is a non-aromatic C$_{1-6}$ hydrocarbon group and R$^7$ is as defined in any one of Embodiments 1.1 to 1.47, amines of the formula (10) can be prepared by the sequence of reactions shown in Scheme 2 below:

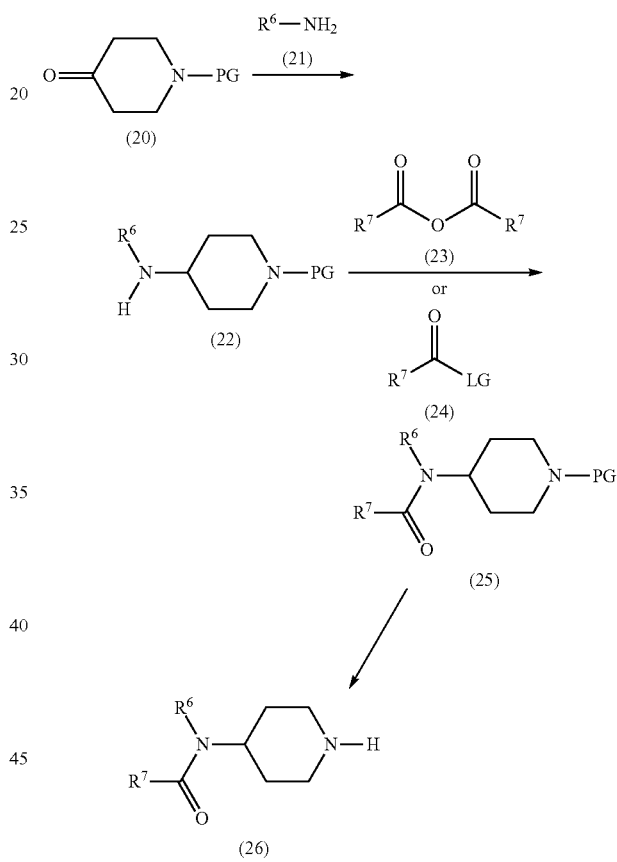

Thus, a ketone of formula (20), wherein PG represents a suitable protecting group such as BOC, CBZ or Bn, can be reacted with an amine of formula (21), wherein R$^6$ is a non-aromatic C$_{1-6}$ hydrocarbon group, under reductive amination conditions to form a compound of formula (22). The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or NaCNBH$_3$ in combination with ZnCl$_2$ in a solvent such as MeOH, or STAB in a solvent such as DCM or DCE containing an acid such as AcOH or TFA in combination with Ti(O$^i$Pr)$_4$. Optionally, the amine of formula (21) may be present in the reaction as an acid salt such as a HCl, HBr or a TFA salt, optionally in the presence of a tertiary base such as TEA or DIPEA. Alternatively, when the protecting group PG is not labile under hydrogenation conditions, the reductive amination reaction can be accomplished by using H₂ in the presence of a Pd/C or Pd(OH)₂/C catalyst in a suitable solvent such as EtOH or MeOH at a temperature of about 20° C. to about 80° C. Once formed, the compound of formula (22) can be reacted with a compound of formula (23) or a compound of formula (24), wherein R⁷ is as defined in any one of Embodiments 1.1 to 1.47 and LG represents an OH group or a suitable leaving group such as Cl, 1-imidazole, or RO(C=O)O (wherein R represents a group such as ethyl- or isobutyl-) under acylation conditions to form amide (25). For the reaction between the compound of formula (22) and a compound of formula (23), suitable acylation conditions might be reaction at a temperature between about 0° C. to about 100° C. in a solvent such as DCM, THF or DMF, optionally in the presence of a tertiary base such as TEA or DIPEA. For the reaction between the compound of formula (22) and a compound of formula (24), wherein LG represents an OH group, it will be well known to the skilled person that many suitable conditions exist in the art to effect formation of amide (25).

For example reaction with an amide coupling reagent such as diisopropylcarbodiimide (DIC), ethyl-(N,N-dimethylamino)propylcarbodiimide hydrochloride (EDC), (benzotriazol-1-yloxy)tripyrrolidinophosphonium hexafluorophosphate (PyBOP), O-(7-azabenzotriazol-1-yl)-N,N,N,N-tetramethyluronium hexafluorophosphate (HATU), (1-cyano-2-ethoxy-2-oxoethylidenaminooxy)dimethylamino-morpholino-carbenium hexafluorophosphate (COMU) or 2,4,6-tripropyl-1,3,5,2,4,6-trioxatriphosphorinane-2,4,6-trioxide (T3P), optionally in the presence of a tertiary base such as TEA or DIPEA, optionally in the presence of 1-hydroxybenzotriazole (HOBt), in a solvent such as DCM, THF or DMF, at a temperature between about 0° C. to about 100° C. Alternatively, for the reaction between the compound of formula (22) and a compound of formula (24), wherein LG represents a leaving group such as Cl, 1-imidazole, or RO(C=O)O (wherein R represents a group such as ethyl- or isobutyl-), suitable acylation conditions might be reaction at a temperature between about 0° C. to about 100° C. in a solvent such as DCM, THF or DMF, optionally in the presence of a tertiary base such as TEA or DIPEA. Once formed, the protecting group PG can be removed from the compound of formula (25) using suitable conditions to form amine (26). For example, when the protecting group PG is BOC, then suitable conditions to effect its removal might be reaction with an acid such as hydrogen chloride (HCl) in a solvent such as 1,4-dioxane or Et₂O, or TFA in a solvent such as DCM. Alternatively, when the protecting group PG is CBZ or Bn, then suitable deprotection conditions might be reaction with H₂ in the presence of a Pd/C or Pd(OH)₂/C catalyst in a suitable solvent such as EtOH or MeOH at a temperature of about 20° C. to about 80° C.

Alternatively, when it is required to prepare a compound of formula (1) wherein R¹ is an optionally substituted monocyclic or bicyclic lactam ring of the form:

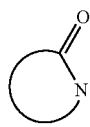

amines of the formula (10) can be prepared by the sequence of reactions shown in Scheme 3 below:

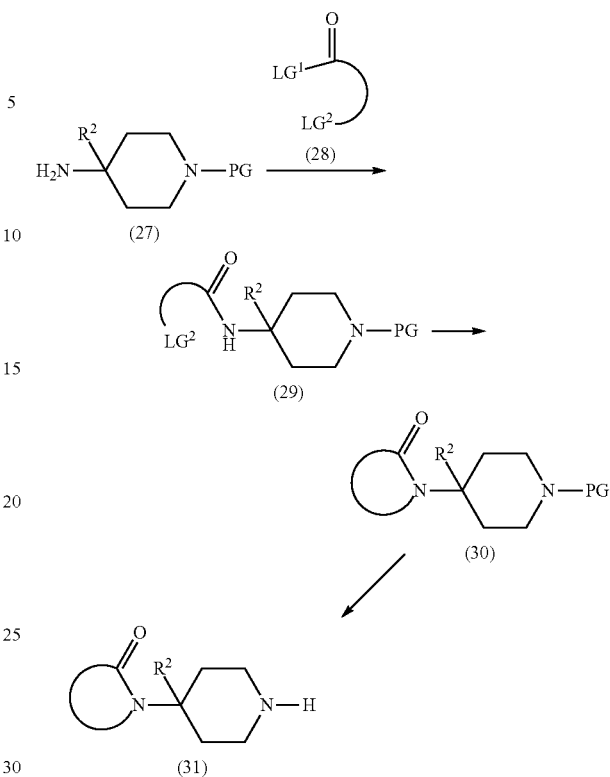

Thus, an amine of formula (27), wherein R² is as defined in any one of Embodiments 1.1 to 1.47 and PG represents a suitable protecting group such as BOC, CBZ or Bn, can be reacted with a compound of formula (28), wherein LG¹ and LG² can be the same or different and represent suitable leaving groups, to form an amide of formula (29). For example, LG¹ could represent an OH group, or a group such as Cl, 1-imidazole, or RO(C=O)O (wherein R represents a group such as ethyl- or isobutyl-) and LG² could represent a halogen such as Cl, Br or I, or a sulphonic acid ester such as a tosylate (OTs), mesylate (OMs) or triflate (OTf). When LG¹ represents an OH group, an amide of formula (29) can be formed from a compound of formula (27) and a compound of formula (28) by using an amide coupling reagent such as DIC, EDC, PyBOP, HATU, COMU or T3P, optionally in the presence of a tertiary base such as TEA or DIPEA, optionally in the presence of HOBt, in a solvent such as DCM, THF or DMF, at a temperature between about 0° C. to about 100° C. Alternatively, when LG¹ represents a group such as Cl, 1-imidazole, or RO(C=O)O (wherein R represents a group such as ethyl- or isobutyl-), an amide of formula (29) can be formed from a compound of formula (27) and a compound of formula (28) by reaction at a temperature between about 0° C. to about 100° C. in a solvent such as DCM, THF or DMF, optionally in the presence of a tertiary base such as TEA or DIPEA. Once formed, the amide of formula (29) can be cyclized to form a lactam of formula (30). Typical cyclisation conditions might be treatment with a suitable base such as sodium hydride (NaH), K₂CO₃, Cs₂CO₃, K'OBu, TEA or DIPEA, in a suitable solvent such as THF, DMF or N-methyl-2-pyrrolidone (NMP) at a temperature between about 0° C. to about 100° C. Once formed, the protecting group PG can be removed from the lactam of formula (30) using suitable conditions to form amine (31). For example, when the protecting group PG is BOC, then suitable conditions to effect its removal might be reaction with an acid such as HCl in a solvent such as 1,4-dioxane or $Et_2O$, or TFA in a solvent such as DCM. Alternatively, when the protecting group PG is CBZ or Bn, then suitable deprotection conditions might be reaction with $H_2$ in the presence of a Pd/C or $Pd(OH)_2$/C catalyst in a suitable solvent such as EtOH or MeOH at a temperature of about 20° C. to about 80° C.

Ketones of the formula (11) can be prepared by the sequence of reactions shown in Scheme 4 below:

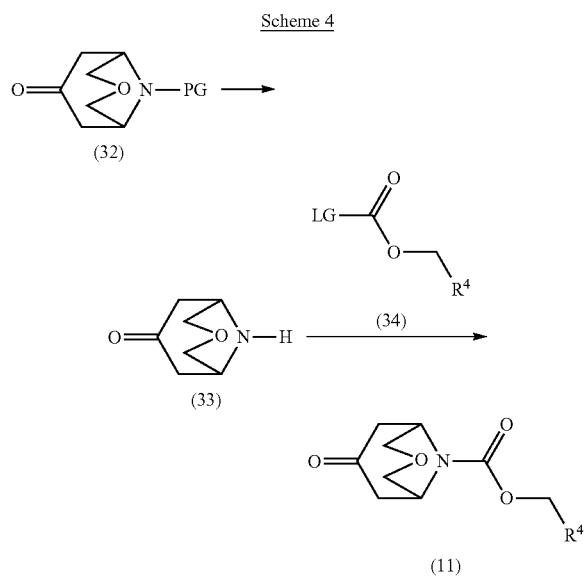

Thus, a protected amino ketone of the formula (32), wherein PG represents a suitable protecting group such as BOC, CBZ or Bn, can be deprotected to give amino ketone (33). For example, when the protecting group PG is BOC, then suitable conditions to effect its removal might be reaction with an acid such as HCl in a solvent such as 1,4-dioxane or $Et_2O$, or TFA in a solvent such as DCM. Alternatively, when the protecting group PG is CBZ or Bn, then suitable deprotection conditions might be reaction with $H_2$ in the presence of a Pd/C or $Pd(OH)_2$/C catalyst in a suitable solvent such as EtOH or MeOH at a temperature of about 20° C. to about 80° C. Once formed, amino ketone (33) can be reacted with a compound of formula (34), wherein $R^4$ is as defined in any one of Embodiments 1.1 to 1.47 and LG represents a suitable leaving group such as Cl, 1-imidazole or 4-nitrophenol, under suitable conditions to form ketone (11). Typically, such conditions are reaction at a temperature between about 0° C. to about 50° C. in a solvent such as DCM, THF or DMF, optionally in the presence of a tertiary base such as TEA or DIPEA.

In process variant (B), the amine of formula (12) is typically reacted with a compound of the formula LG-C(=O)—O—$CH_2$—$R^4$; wherein $R^4$ is as defined in any one of Embodiments 1.1 to 1.47 and LG represents a suitable leaving group such as Cl, 1-imidazole or 4-nitrophenol, at a temperature between about 0° C. to about 50° C. in a solvent such as DCM, THF or DMF, optionally in the presence of a tertiary base such as TEA or DIPEA.

Amines of the formula (12) can be prepared by the sequence of reactions shown in Scheme below:

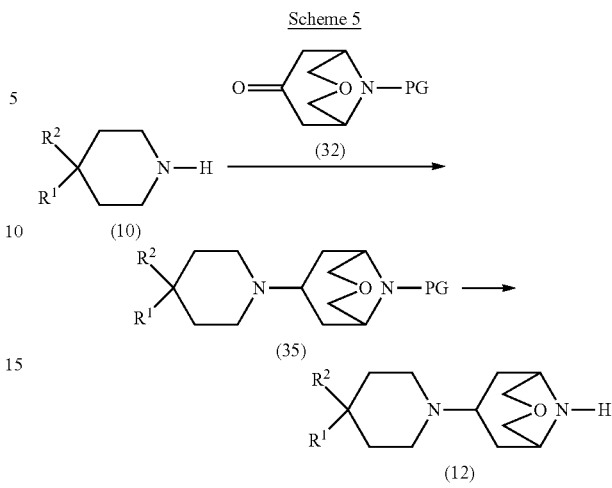

Thus, an amine of formula (10), wherein $R^1$ and $R^2$ are as defined in any one of Embodiments 1.1 to 1.47, can be reacted with a ketone (32) wherein PG represents a suitable protecting group such as BOC, CBZ or Bn, under reductive amination conditions to form a compound of formula (35). The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or $NaCNBH_3$ in combination with $ZnCl_2$ in a solvent such as MeOH, or STAB in a solvent such as DCM or DCE containing an acid such as AcOH or TFA in combination with $Ti(O^iPr)_4$. Optionally, the amine of formula (10) may be present in the reaction as an acid salt such as a HCl, HBr or a TFA salt, optionally in the presence of a tertiary base such as TEA or DIPEA. Alternatively, when the protecting group PG is not labile under hydrogenation conditions, the reductive amination reaction can be accomplished by using $H_2$ in the presence of a Pd/C or $Pd(OH)_2$/C catalyst in a suitable solvent such as EtOH or MeOH at a temperature of about 20° C. to about 80° C. Once formed, the protecting group PG can be removed from the compound of formula (35) using suitable conditions to form an amine of formula (12). For example, when the protecting group PG is BOC, then suitable conditions to effect its removal might be reaction with an acid such as HCl in a solvent such as 1,4-dioxane or $Et_2O$, or TFA in a solvent such as DCM. Alternatively, when the protecting group PG is CBZ or Bn, then suitable deprotection conditions might be reaction with $H_2$ in the presence of a Pd/C or $Pd(OH)_2$/C catalyst in a suitable solvent such as EtOH or MeOH at a temperature of about 20° C. to about 80° C.

In process variant (C), the ester of formula (13) is reacted with the amine of formula $R^8R^9NH$ under conditions suitable to effect the formation of an amide. Typically, such conditions are reaction at a temperature between about 0° C. to about 110° C. in a solvent such as toluene in combination with a reagent such as trimethylaluminium ($Me_3Al$), optionally in the presence of a tertiary base such as TEA or DIPEA. It will be well known to the skilled person that other suitable conditions exist to effect formation of an amide from an ester of formula (13) and an amine of formula $R^8R^9NH$, such as reaction in the presence of isopropylmagnesium chloride ($^iPrMgCl$) in a suitable solvent, or by direct heating of an ester of formula (13) and an amine of formula $R^8R^9NH$ together, optionally in the presence of a suitable solvent, optionally in the presence of a suitable base such as TEA or DIPEA.

An ester of formula (13) can be prepared by the sequence of reactions shown in Scheme 6 below:

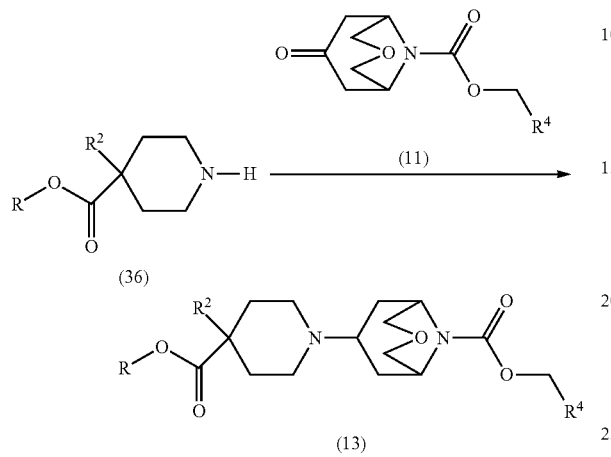

Thus, an ester of formula (36), wherein R² is as defined in any one of Embodiments 1.1 to 1.47 and R represents a suitable group such as methyl- or ethyl-, can be reacted with a ketone of formula (11), wherein R⁴ is as defined in any one of Embodiments 1.1 to 1.47, under reductive amination conditions to form an ester of formula (13). The reductive amination reaction is typically carried out at ambient temperature to mild heating (e.g. at a temperature of about 20° C. to about 70° C.) using a borohydride reducing agent such as STAB in a solvent such as DCM, DCE, DMF or MeOH containing an acid such as AcOH or TFA, or NaCNBH₃ in combination with ZnCl₂ in a solvent such as MeOH, or STAB in a solvent such as DCM or DCE containing an acid such as AcOH or TFA in combination with Ti(OⁱPr)₄. Optionally, the amine of formula (10) may be present in the reaction as an acid salt such as a HCl, HBr or a TFA salt, optionally in the presence of a tertiary base such as TEA or DIPEA. Alternatively, when it is appropriate to do so, the reductive amination reaction can be accomplished by using H₂ in the presence of a Pd/C or Pd(OH)₂/C catalyst in a suitable solvent such as EtOH or MeOH at a temperature of about 20° C. to about 80° C.

In process variant (D), the carboxylic acid of formula (14) is reacted with the amine of formula R⁸R⁹NH under conditions suitable to effect the formation of an amide. It will be well known to the skilled person that many suitable conditions exist in the art to effect formation of amide from a carboxylic acid of formula (14) and an amine of formula R⁸R⁹NH. For example, reaction with an amide coupling reagent such as DIC, EDC, PyBOP, HATU, COMU or T3P, optionally in the presence of a tertiary base such as TEA or DIPEA, optionally in the presence of HOBt, in a solvent such as DCM, THF or DMF, at a temperature between about 0° C. to about 100° C.

A carboxylic acid of formula (14) can be prepared by the reaction shown in Scheme 7 below:

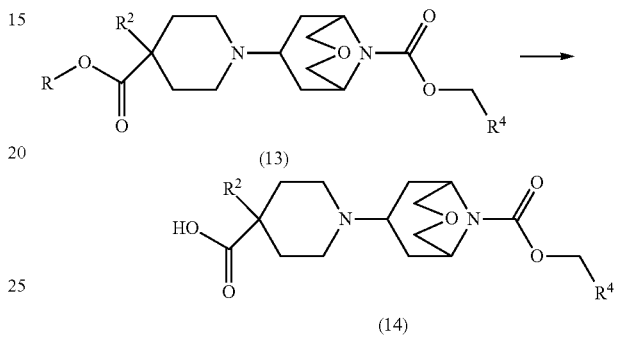

Thus, an ester of formula (13), wherein R² and R⁴ are as defined in any one of Embodiments 1.1 to 1.47 and R represents a suitable group such as methyl- or ethyl-, tert-butyl- or benzyl-can be reacted under conditions suitable to effect cleavage of the ester to form a carboxylic acid of formula (14). Typically, when R represents methyl- or ethyl-, basic conditions might used, for example reaction with a reagent such as lithium hydroxide (LiOH), sodium hydroxide (NaOH) or potassium hydroxide (KOH) in a solvent such as THF, MeOH, EtOH, water (H₂O) or a combination of two or more of the aforementioned solvents, at a temperature of between about 0° C. to about 100° C. Alternatively, when R represents tert-butyl-, acidic conditions might be used, for example reaction with a reagent such as TFA in a solvent such as DCM, or reaction with HCl in a solvent such as 1,4-dioxane or Et₂O. Alternatively, when R represents benzyl-, hydrogenolysis conditions might be used, for example reaction with H₂ in the presence of a Pd/C or Pd(OH)₂/C catalyst in a suitable solvent such as EtOH or MeOH at a temperature of about 20° C. to about 80° C.

Alternatively, the carboxylic acid of formula (14) can be reacted with the amine of formula R⁸R⁹NH to effect the formation of an amide by the sequence of reactions shown in Scheme 8 below:

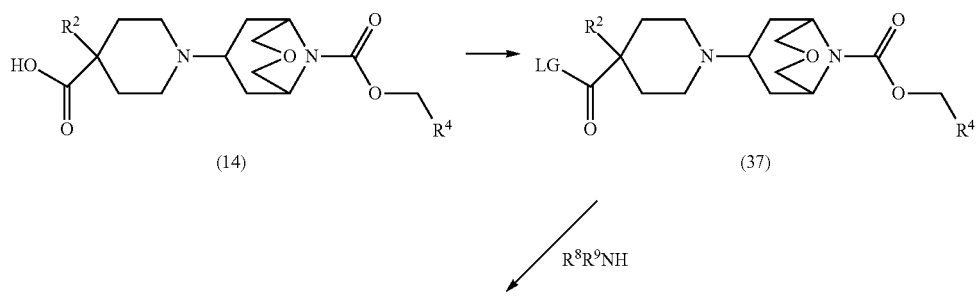

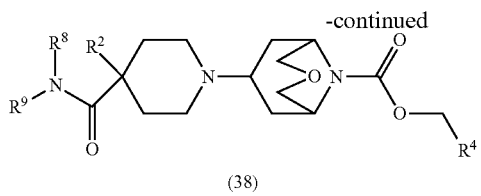

(38)

Thus, the carboxylic acid of formula (14) can be reacted to form a compound of formula (37), wherein $R^2$, $R^4$, $R^8$ and $R^9$ are as defined in any one of Embodiments 1.1 to 1.47 and LG represents a suitable leaving group such as Cl, 1-imidazole, or RO(C=O)O (wherein R represents a group such as ethyl- or isobutyl-). Typically, such conditions are reaction with a reagent such as oxalyl chloride or thionyl chloride (LG=Cl), 1,1'-carbonyldiimidazole (CDI) (LG=1-imidazole) or ethyl- or isobutyl-chloroformate (LG=RO(C=O)O), optionally in the presence of a tertiary base such as TEA or DIPEA, optionally in the presence of a catalyst such as DMF, in a suitable solvent such as DCM, THF or DMF. Once formed, the compound of formula (37), is reacted with an amine of the formula $R^8R^9NH$ under conditions suitable to effect the formation of amide (38). Typically, such conditions are reaction at a temperature between about 0° C. to about 100° C. in a solvent such as DCM, THF or DMF, optionally in the presence of a tertiary base such as TEA or DIPEA.

In process variant (E), one compound of the formula (1) can be converted into another compound of the formula (1) by methods well known to the skilled person. Examples of synthetic procedures for converting one functional group into another functional group are set out in standard texts such as *March's Advanced Organic Chemistry: Reactions, Mechanisms, and Structure,* 7th Edition, Michael B. Smith, John Wiley, 2013, (ISBN: 978-0-470-46259-1), Organic Syntheses, Online Edition, www.orgsyn.org, (ISSN 2333-3553) and Fiesers' Reagents for Organic Synthesis, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Greene's Protective Groups in Organic Synthesis,* Fifth Edition, Editor: Peter G. M. Wuts, John Wiley, 2014, (ISBN: 9781118057483).

Compounds made by the foregoing methods may be isolated and purified by any of a variety of methods well known to those skilled in the art and examples of such methods include recrystallisation and chromatographic techniques such as column chromatography (e.g. flash chromatography), HPLC and SFC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.47 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragees, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers. Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 8-25

Some of the compounds of Examples 1-1 to 8-25 shown in Table 1 below have been prepared. Their NMR and LCMS properties and the methods used to prepare them are set out in Table 3. The starting materials for each of the Examples are listed in Table 2.

TABLE 1

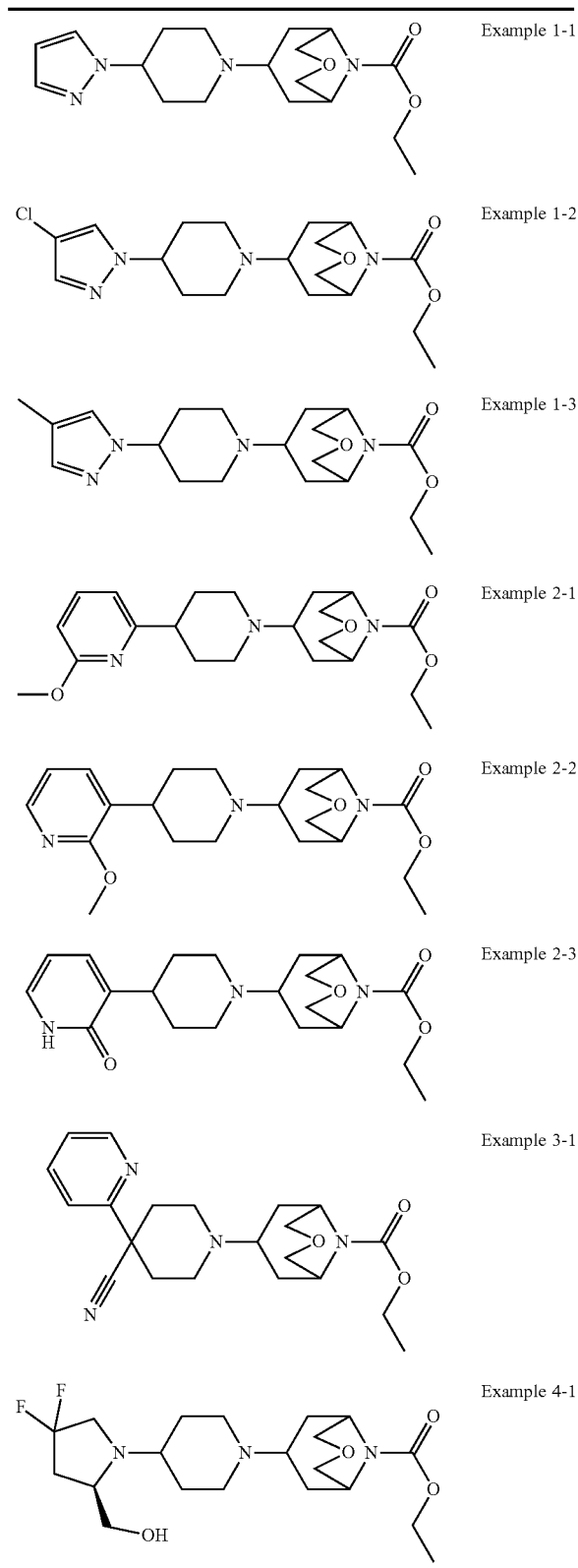

TABLE 1-continued
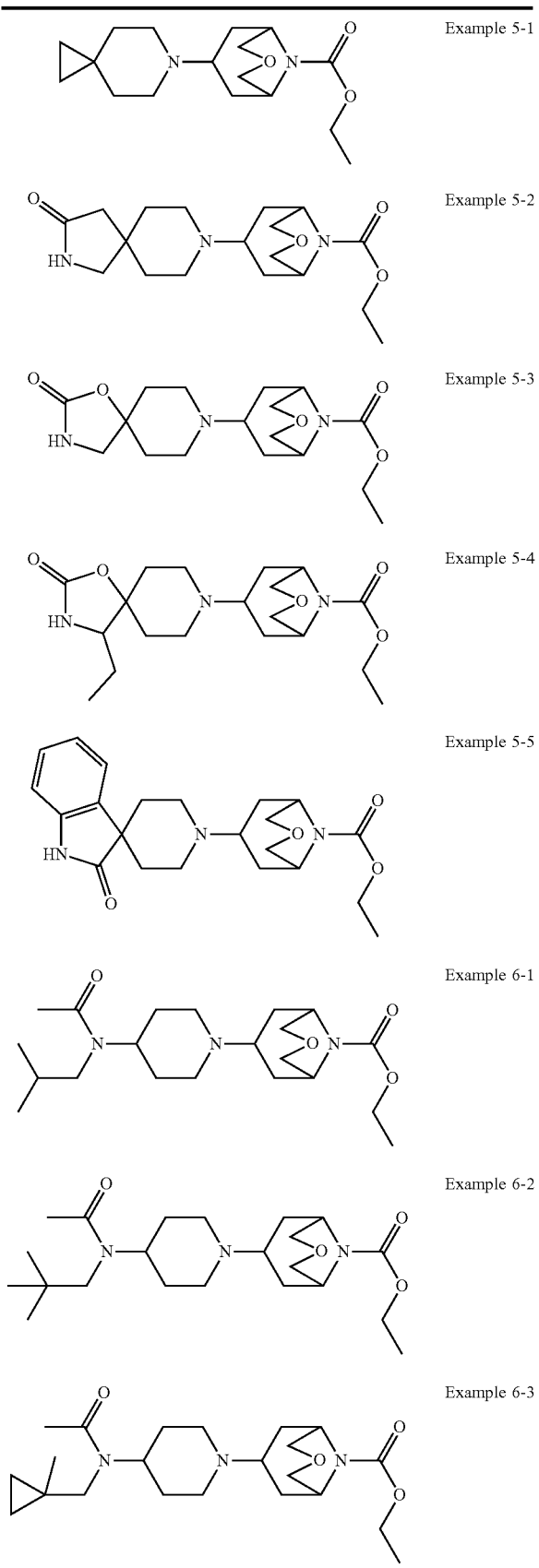
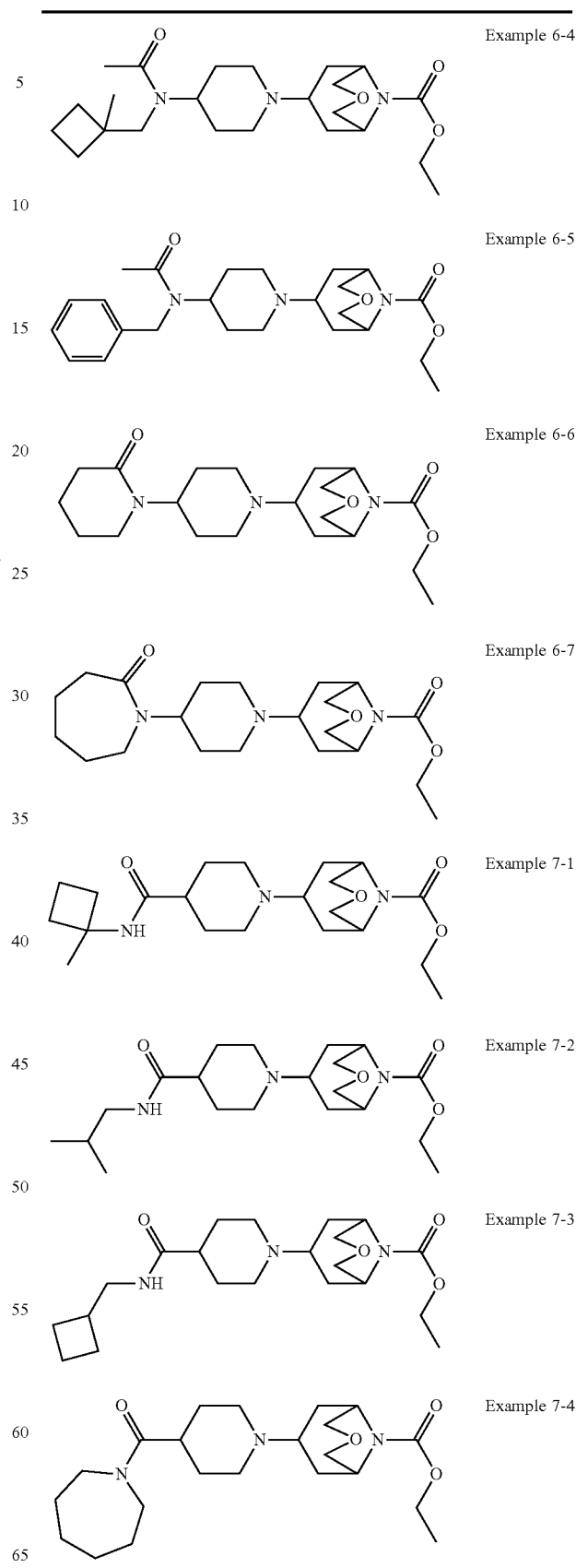

TABLE 1-continued
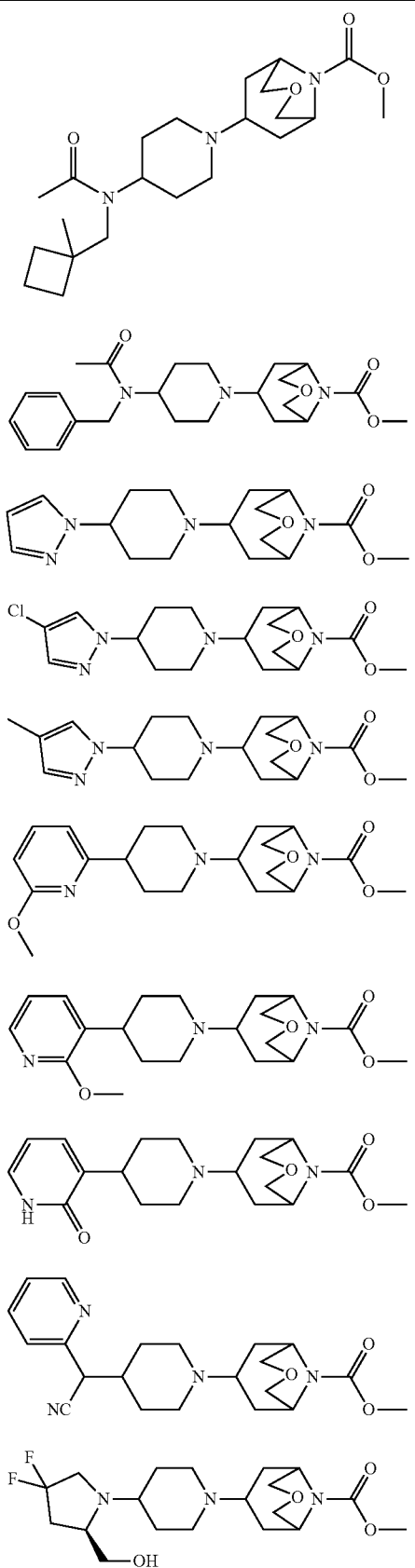
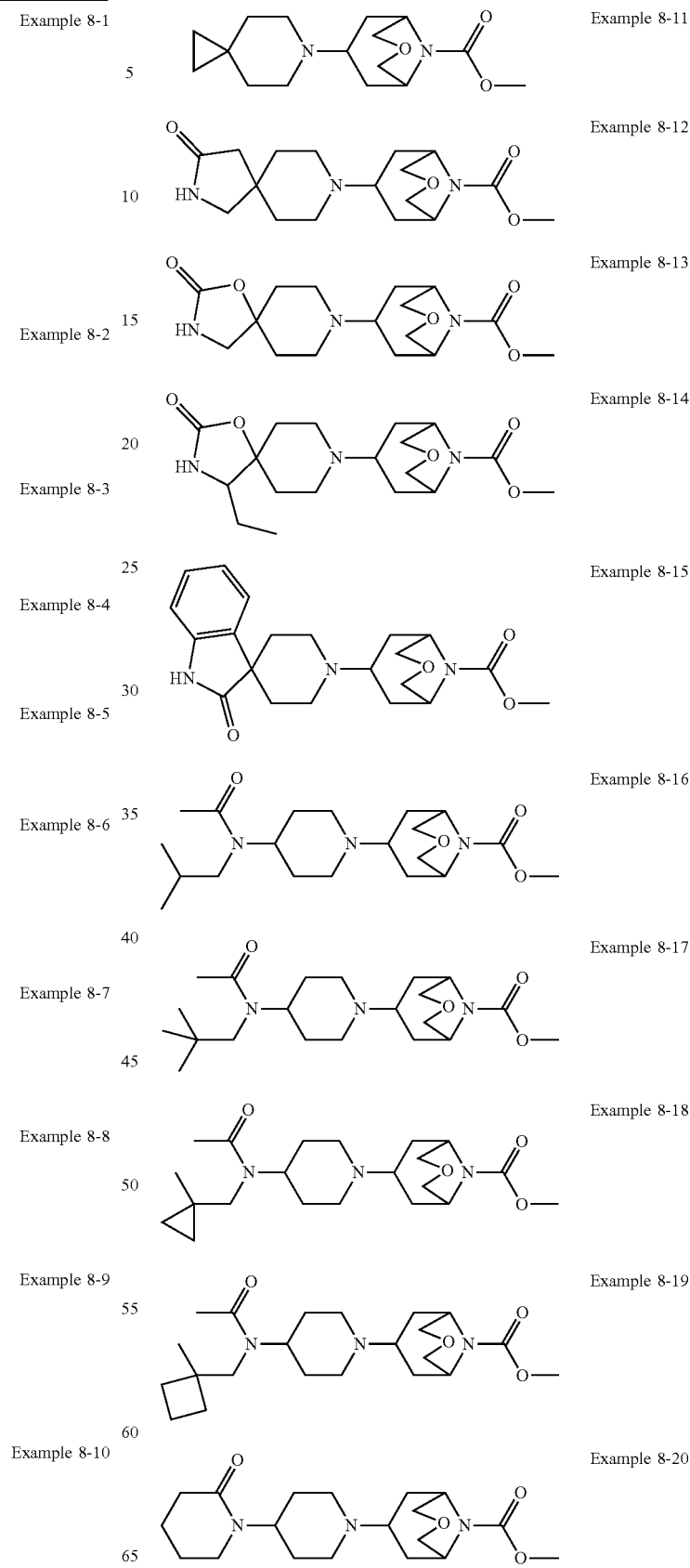

TABLE 1-continued

| Structure | Example |
|---|---|
| (structure) | Example 8-21 |
| (structure) | Example 8-22 |
| (structure) | Example 8-23 |
| (structure) | Example 8-24 |
| (structure) | Example 8-25 |

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and the Silica gel F254 as a stationary phase from Merck. Microwave-mediated reactions were performed in Biotage Initiator or CEM Discover microwave reactors.

LCMS Analysis

LCMS analysis of compounds was performed under electrospray conditions using the instruments and methods given in the tables below:

| System ID | Instrument Name | LC Detector | Mass Detector |
|---|---|---|---|
| 1 | Waters 2695 | Photo Diode Array | ZQ-2000 Detector |
| 2 | Waters Acquity H Class | Photo Diode Array | SQ Detector |
| 3 | Shimadzu Nexera | Photo Diode Array | LCMS-2020 |
| 4 | Agilent 1290 RRLC with Agilent 6120 Mass detector | Photo Diode Array | Agilent 6120 |

| Method Name | Solvent System | Column used | Gradient | UV Range | Mass Range | Column Temp. ° C. | Flow Rate ml/min |
|---|---|---|---|---|---|---|---|
| A | (A) 5 mM ammonium acetate + 0.1% formic acid in water (B) 0.1% formic acid in acetonitrile | BEH C18 2.1 × 50 mm, 1.7 μm or equivalent | 95:5 at 0.01 min up to 0.40 min, 65:35 at 0.80 min, 45:55 at 1.20 min, 0:100 at 2.50 min up to 3.30 min, 95:5 at 3.31 min up to 4.00 min | 200-400 nm | 100-1200 amu | Ambient | 0.55 |
| B | (A) 20 mM ammonium acetate in water (B) methanol | X-Bridge C18 4.6 × 150 mm, 5 μm or equivalent | 90:10 at 0.01 min, 10:90 at 5.00 min, 0:100 at 7.00 min up to 11.00 min, 90:10 at 11.01 min up to 12.00 min | 200-400 nm | 60-1000 amu | Ambient | 1.00 |
| C | (A) 0.1% ammonia in water (B) 0.1% ammonia in acetonitrile | X-Bridge O18 4.6 × 50 mm, 3.5 μm or equivalent | 95:5 at 0.01 min, 10:90 at 5.00 min, 5:95 at 5.80 min up to 7.20 min, 95:5 at 7.21 min up to 10.00 min | 200-400 nm | 60-1000 amu | Ambient | 1.00 |
| D | (A) 5 mM ammonium bicarbonate in water (B) acetonitrile | X-Bridge C18 4.6 × 50 mm, 3.5 μm or equivalent | 95:5 at 0.01 min, 10:90 at 5.00 min, 5:95 at 5.80 min up to 7.20 min, 95:5 at 7.21 min up to 10.00 min | 200-400 nm | 60-1000 amu | Ambient | 1.00 |

LCMS data in the experimental section and Tables 2 and 3 are given in the format: (Instrument system, Method): Mass ion, retention time, UV detection wavelength.

Compound Purification

Final purification of compounds was performed by preparative reversed phase HPLC, chiral HPLC or chiral SFC using the instruments and methods detailed below where data is given in the following format: Purification technique: [phase (column description, column length×internal diameter, particle size), solvent flow-rate, gradient—given as % of mobile phase B in mobile phase A (over time), mobile phase (A), mobile phase (B)].

Preparative HPLC Purification:
Shimadzu LC-20AP binary system with SPD-20A UV detector Chiral HPLC Purification:
Shimadzu LC-20AP binary system with SPD-20A UV detector Chiral SFC Purification:
Waters SFC 200

Purification Method A
SFC: [(CHIRALPAK AD-H, 250×21 mm, 5 μm), 80 mL per min, mobile phase (A): 100% liquid $CO_2$, (B): 0.1% diethylamine in IPA:MeOH (50:50), Isocratic (A:B) (85:15) (over 10 mins)]

Purification Method B
Prep HPLC: [Reversed phase (X-BRIDGE C-8, 250×19 mm, 5 μm), 16 mL per min, gradient 5-40% (over 35 min), 40% (over 2 min), 100% (over 2 min), then 100-5% (over 4 min), mobile phase (A): 5 mM ammonium bicarbonate+0.1% ammonia in water, (B) 100% acetonitrile]

Purification Method C
Prep HPLC: [Reversed Phase (X SELECT PHENYL HEXYL, 250×19 mm, 5 μm), 15 mL per min, gradient 20-35% (over 30 min), 100% (over 2 min), then 100-20% (over 2 min), mobile phase (A): 0.1% formic acid in water, (B) 100% acetonitrile]

Purification Method D
SFC: [(CHIRALPAK IB, 250×21 mm, 5 μm), 75 mL per min, mobile phase (A): 100% liquid $CO_2$, (B): 0.1% diethylamine in MeOH, Isocratic (A:B) (90:10) (over 8 min)]

Purification Method E
SFC: [(CHIRALCEL OX-H, 250×21 mm, 5 μm), 70 mL per min, mobile phase (A): 100% liquid $CO_2$, (B): 0.1% diethylamine in IPA:MeOH (50:50), Isocratic (A:B) (75:25) (over 13 mins)]

Purification Method F
Prep HPLC: [Reversed Phase (X SELECT PHENYL HEXYL, 250×19 mm, 5 μm), 18 mL per min, gradient 5-65% (over 20 min), 100% (over 2 min), then 100-5% (over 3 min), mobile phase (A): mM ammonium bicarbonate+0.1% ammonia in water, (B) 100% acetonitrile]

Purification Method G
SFC: [(CHIRALPAK IC, 250×21 mm, 5 μm), 70 mL per min, mobile phase (A): 100% liquid $CO_2$, (B): 0.1% diethylamine in IPA, Isocratic (A:B) (75:25) (over 20 mins)]

Purification Method H
Prep HPLC: [Reversed Phase (X SELECT PHENYL HEXYL, 250×19 mm, 5 μm), 15 mL per min, gradient 5-55% (over 18 min), 100% (over 2 min), then 100-5% (over 3 min), mobile phase (A): 5 mM ammonium bicarbonate+0.1% ammonia in water, (B) 100% acetonitrile]

Purification Method I
SFC: [(CHIRALPAK AD-H, 250×21 mm, 5 μm), 70 mL per min, mobile phase (A): 100% liquid $CO_2$, (B): 0.2% diethylamine in IPA:MeOH (50:50), Isocratic (A:B) (75:25) (over 9 mins)]

Purification Method J
Prep HPLC: [Reversed Phase (X-BRIDGE C-8, 250×19 mm, 5 μm), 17 mL per min, gradient 0-50% (over 33 min), 100% (over 2 min), then 100-0% (over 2 min), mobile phase (A): 5 mM ammonium bicarbonate+0.1% ammonia in water, (B) 100% acetonitrile]

Purification Method K
SFC: [(CHIRALPAK AD-H, 250×21 mm, 5 μm), 75 mL per min, mobile phase (A): 100% liquid $CO_2$, (B): 0.1% diethylamine in MeOH, Isocratic (A:B) (85:15) (over 14.0 mins)]

Purification Method L
Prep HPLC: [Reversed Phase (X SELECT PHENYL HEXYL, 250×19 mm, 5 μm), 17 mL per min, gradient 35-45% (over 17 min), 100% (over 2 min), then 100-35% (over 2 min), mobile phase (A): 5 mM ammonium bicarbonate+0.1% ammonia in water, (B) 100% acetonitrile]

Purification Method M
SFC: [(CHIRALCEL OX-H, 250×21 mm, 5 μm), 75 mL per min, mobile phase (A): 100% liquid CO2, (B): 0.1% diethylamine in MeOH, Isocratic (A:B) (85:15) (over 20 mins)]

Purification Method N
Prep HPLC: [Reversed Phase (X-BRIDGE C-18, 250×19 mm, 5 μm), 16 mL per min, gradient 25% (over 46 min), 100% (over 3 min), then 100-25% (over 5 min), mobile phase (A): 5 mM ammonium bicarbonate+0.05% ammonia in water, (B) 100% acetonitrile]

Purification Method O
SFC: [(CHIRALPAK AD-H, 250×21 mm, 5 μm), 70 mL per min, mobile phase (A): 100% liquid $CO_2$, (B): 0.1% diethylamine in IPA:MeOH (50:50), Isocratic (A:B) (75:25) (over 17.0 mins)]

Purification Method P
Prep HPLC: [Reversed Phase (X-BRIDGE C-8, 250×19 mm, 5 μm), 15 mL per min, gradient 5-20% (over 35 min), 100% (over 2 min), then 100-5% (over 3 min), mobile phase (A): 5 mM ammonium bicarbonate+0.05% ammonia in water, (B) 100% acetonitrile]

Purification Method Q
SFC: [(CHIRALPAK IB, 250×20 mm, 5 μm), 70 mL per min, mobile phase (A): 100% liquid $CO_2$, (B): 0.1% diethylamine in IPA:MeOH (50:50), Isocratic (A:B) (85:15) (over 9 mins)]

Purification Method R
Prep HPLC: [Reversed Phase (X SELECT PHENYL HEXYL, 250×19 mm, 5 μm), 13 mL per min, gradient 15-40% (over 20 min), 100% (over 2 min), then 100-15% (over 3 min), mobile phase (A): 5 mM ammonium bicarbonate+0.1% ammonia in water, (B) 100% acetonitrile]

Purification Method S
SFC: [(CHIRALPAK AD-H, 250×21 mm, 5 μm), 80 mL per min, mobile phase (A): 100% liquid $CO_2$, (B): 0.1% diethylamine MeOH, Isocratic (A:B) (75:25) (over 8 min)]

Purification Method T
Prep HPLC: [Reversed Phase (X-BRIDGE C-8, 250×19 mm, 5 μm), 16 mL per min, gradient 20-30% (over 25 min), 30% (over 5 min), 100% (over 2 min), then 100-20% (over 3 min), mobile phase (A): 5 mM ammonium bicarbonate+0.05% ammonia in water, (B): 100% acetonitrile]

Purification Method U
Chiral HPLC [Normal Phase (CHIRALPAK AD-H 250× 21 mm, 5 μm), 18 mL per min, mobile phase (A): 0.1% diethylamine in hexane, B) 0.1% diethylamine in IPA: MeOH (25:75), Isocratic (A:B) (80:20) (over 25 min)]

Purification Method V
    Prep HPLC: [Reversed Phase (X-BRIDGE C-8, 250×19 mm, 5 μm), 16 mL per min, gradient 10-35% (over 30 min), 35% (over 14 min), 100% (over 2 min), then 100-10% (over 2 min), mobile phase (A): 5 mM ammonium bicarbonate+0.1% ammonia in water, (B): 100% acetonitrile]
Purification Method W
    Chiral HPLC: [Normal Phase (CHIRALPAK AD-H 250×21 mm, 5 μm), 18 mL per min, mobile phase (A): 0.1% diethylamine in hexane, B) 0.1% diethylamine in IPA:MeOH (30:70), Isocratic (A:B) (85:15) (over 20 min)]
Purification Method X
    Prep HPLC: [Reversed Phase (X-BRIDGE C-18, 250×19 mm, 5 μm), 15 mL per min, gradient 10-40% (over 25 min), 40% (over 5 min), 100% (over 2 min), then 100-10% (over 4 min), mobile phase (A): 5 mM ammonium bicarbonate+0.1% ammonia in water, (B): 100% acetonitrile]
Purification Method Y
    Chiral HPLC [Normal Phase (CHIRALPAK AD-H 250×21 mm, 5 μm), 18 mL per min, mobile phase (A): 0.1% diethylamine in hexane, B) 0.1% diethylamine in IPA, Isocratic (A:B) (90:10) (over 37 min)]
Purification Method Z
    Prep HPLC: [Reversed Phase (X SELECT PHENYL HEXYL, 250×19 mm, 5 μm), 15 mL per min, gradient 20-50% (over 23 min), 100% (over 2 min), then 100-20% (over 4 min), mobile phase (A): 5 mM ammonium bicarbonate+0.1% ammonia in water, (B) 100% acetonitrile]
Purification Method AA
    SFC: [(CHIRALPAK IB, 250×20 mm, 5 μm), 70 mL per min, mobile phase (A): 100% liquid $CO_2$, (B): 0.1% diethylamine in MeOH, Isocratic (A:B) (85:15) (over 7 min)]
Purification Method AB
    Prep HPLC: [Reversed Phase (X-BRIDGE C-8, 250×19 mm, 5 μm), 15 mL per min, gradient 20-45% (over 20 min), 100% (over 2 min), then 100-20% (over 5 min) mobile phase (A): 5 mM ammonium bicarbonate+0.1% ammonia in water, (B) 100% acetonitrile]
Purification Method AC
    Chiral HPLC [Normal Phase (CHIRALPAK AD-H 250×21 mm, 5 μm), 18 mL per min, mobile phase (A): 0.1% diethylamine in hexane, B) 0.1% diethylamine in IPA:MeOH (25:75), Isocratic (A:B) (80:20) (over 50 min)]
Purification Method AD
    Prep HPLC: [Reversed Phase (X-BRIDGE C-8, 250×19 mm, 5 μm), 15 mL per min, gradient 0-28% (over 25 min), 28% (over 5 min), 100% (over 2 min), then 100-0% (over 3 min), mobile phase (A): 5 mM ammonium bicarbonate+0.05% ammonia in water, (B) 100% acetonitrile]
Purification Method AE
    SFC: [(CHIRALPAK IB, 250×20 mm, 5 μm), 70 mL per min, mobile phase (A): 100% liquid $CO_2$, (B): 0.1% diethylamine in IPA:MeOH (50:50), Isocratic (A:B) (80:20) (over 10 mins)]
Purification Method AF
    Prep HPLC: [Reversed Phase (X SELECT PHENYL HEXYL, 250×19 mm, 5 μm), 15 mL per min, gradient 5-27% (over 42 min), 27% (over 6 min), 100% (over 2 min), then 100-5% (over 3 min), mobile phase (A): 5 mM ammonium bicarbonate+0.05% ammonia in water, (B) 100% acetonitrile]
Purification Method AG
    SFC: [(CHIRALPAK AD-H, 250×21 mm, 5 μm), 70 mL per min, mobile phase (A): 100% liquid $CO_2$, (B): 0.1% diethylamine in IPA:MeOH (50:50), Isocratic (A:B) (70:30) (over 6 mins)]
Purification Method AN
    Prep HPLC: [Reversed Phase (X-BRIDGE C-8, 250×19 mm, 5 μm), 15 mL per min, gradient 15-35% (over 20 min), 35% (over 3 min), 100% (over 2 min), then 100-15% (over 4 min), mobile phase (A): 5 mM ammonium bicarbonate+0.1% ammonia in water, (B) 100% acetonitrile]
Purification Method AI
    SFC: [(CHIRALPAK IB, 250×20 mm, 5 μm), 70 mL per min, mobile phase (A): 100% liquid CO2, (B): 0.1% diethylamine in IPA:MeOH (50:50), Isocratic (A:B) (85:15) (over 8 mins)]
Purification Method AJ
    Prep HPLC: [Reversed Phase (X SELECT PHENYL HEXYL, 250×19 mm, 5 μm), 15 mL per min, gradient 0-38% (over 28 min), 100% (over 2 min), then 100-0% (over 3 min), mobile phase (A): 5 mM ammonium bicarbonate+0.1% ammonia in water, (B) 100% acetonitrile]
Purification Method AK
    SFC: [(CHIRALPAK IB, 250×20 mm, 5 μm), 70 mL per min, mobile phase (A): 100% liquid $CO_2$, (B): 0.1% ammonia in IPA:MeOH (50:50), Isocratic (A:B) (88:12) (over 20 mins)]
Purification Method AL
    Prep HPLC: [Reversed Phase (X SELECT PHENYL HEXYL, 250×19 mm, 5 μm), 15 mL per min, gradient 0-40% (over 24 min), 40% (over 4 min), 100% (over 4 min), then 100-0% (over 3 min), mobile phase (A): 5 mM ammonium bicarbonate+0.1% ammonia in water, (B) 100% acetonitrile]
Purification Method AM
    SFC: [(CHIRALPAK AD-H, 250×21 mm, 5 μm), 70 mL per min, mobile phase (A): 100% liquid $CO_2$, (B): 0.1% diethylamine in IPA:MeOH (50:50), Isocratic (A:B) (87:13) (over 12 mins)]
Purification Method AN
    Prep HPLC: [Reversed Phase (X-BRIDGE C-8, 250×19 mm, 5 μm, 13 mL per min, gradient 0-30% (over 55 min), 30% (over 20 min), 100% (over 2 min), then 100-0% (over 3 min), mobile phase (A): 5 mM ammonium bicarbonate+0.05% ammonia in water, (B) 100% acetonitrile]
Purification Method AO
    SFC: [(CHIRALPAK IB, 250×20 mm, 5 μm), 80 mL per min, mobile phase (A): 100% liquid $CO_2$, (B): 0.1% diethylamine in IPA:MeOH (50:50), Isocratic (A:B) (85:15) (over 9 mins)]
Purification Method AP
    Prep HPLC: [Reversed Phase (X-BRIDGE C-18, 250×19 mm, 5 μm, 10 mL per min, gradient 10-70% (over 20 min), 70% (over 2 min), 100% (over 2 min), then 100-10% (over 4 min), mobile phase (A): 5 mM ammonium bicarbonate+0.1% ammonia in water, (B) 100% acetonitrile]
Purification Method AQ
    Prep HPLC: [Reversed Phase (X-BRIDGE C-8, 250×19 mm, 5 μm, 14 mL per min, gradient 15-30% (over 35 min), 70% (over 16 min), 100% (over 2 min), then 100-15% (over 6 min), mobile phase (A): 5 mM ammonium bicarbonate+0.1% ammonia in water, (B) 100% acetonitrile]
Purification Method AR
    Prep HPLC: [Reversed Phase (X-BRIDGE C-8, 250×19 mm, 5 μm, 16 mL per min, gradient 20% (over 60 min), 100% (over 2 min), then 100-20% (over 5 min), mobile phase (A): 5 mM ammonium bicarbonate+0.1% ammonia in water, (B) 100% acetonitrile]

Abbreviations atm.=atmosphere
conc.=concentrated
DCM=dichloromethane
DMF=dimethylformamide
ES(I)=electro spray ionisation
EtOAc=ethyl acetate
h=hour(s)
$H_2O$=water
HCl=hydrogen chloride, hydrochloric acid
HPLC=high performance liquid chromatography
IPA=isopropanol (propan-2-ol)
LC=liquid chromatography
MeOH=Methanol
min(s)=minute(s)
MS=mass spectrometry
nm=nanometre(s)
NMR=nuclear magnetic resonance
SFC=supercritical fluid chromatography
TEA=triethylamine
TFA=trifluoroacetic acid
TLC=thin layer chromatography Prefixes n-, s-, i-, t- and tert-have their usual meanings: normal, secondary, iso, and tertiary.

Synthesis of Intermediates:

Route 1

Typical Procedure for the Preparation of Ketones, as Exemplified by the Preparation of Intermediate 3, ethyl 7-oxo-3-oxa-9-azabicyclo[3.3.1]nonane-9-carboxylate

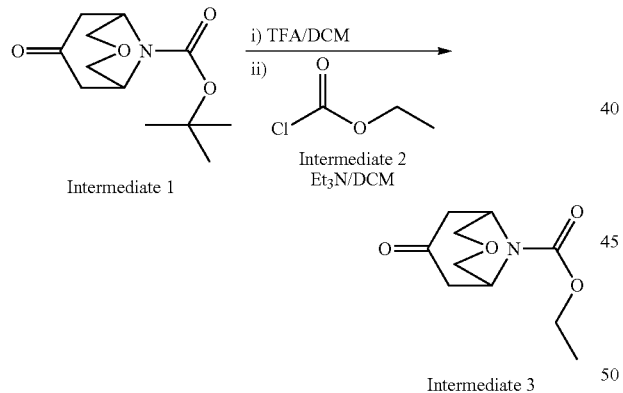

tert-Butyl 7-oxo-3-oxa-9-azabicyclo[3.3.1]nonane-9-carboxylate (Intermediate 1) (200 mg, 0.83 mmol) was dissolved in DCM (8 mL) and the solution was cooled down to 0° C. TFA (1 mL) was added drop wise, and the resulting reaction mixture was stirred at 25° C. for 6 h. The solvents were removed in-vacuo and the residue was purified by triturating with diethyl ether (3×1 mL) to give the crude 3-oxa-9-azabicyclo[3.3.1]nonan-7-one trifluoroacetate (115 mg, 98%) as a white solid.

LCMS (System 4, Method C): m/z 142 (M+H)+ (ESI+ve), at 0.59-0.80 min, 202 nm.

Triethylamine (0.3 mL, 2.44 mmol) was added to a solution of the crude 3-oxa-9-azabicyclo[3.3.1]nonan-7-one trifluoroacetate (115 mg, 0.82 mmol) in DCM (10 mL), and the mixture was cooled to 0° C. and stirred for 20 min. Ethyl chloroformate (Intermediate 2) (0.13 mL, 1.22 mmol) was then added drop wise at 0° C., and the resulting reaction mixture was stirred at 25° C. for 1 h. The solvents were removed in-vacuo, and the residue was partitioned between $H_2O$ (80 mL) and EtOAc (60 mL). The aqueous layer was further extracted with EtOAc (2×60 mL), and the combined organic layers were dried ($Na_2SO_4$) and the solvents were removed in-vacuo to give ethyl 7-oxo-3-oxa-9-azabicyclo[3.3.1]nonane-9-carboxylate (Intermediate 3) as a gum (170 mg, 98%), which was used without further purification.

The data for Intermediate 3 are in Table 2

Route 2

Typical Procedure for the Preparation of Piperidines, as Exemplified by the Preparation of Intermediate 9, 2-methoxy-6-(piperidin-4-yl)pyridine Hydrochloride

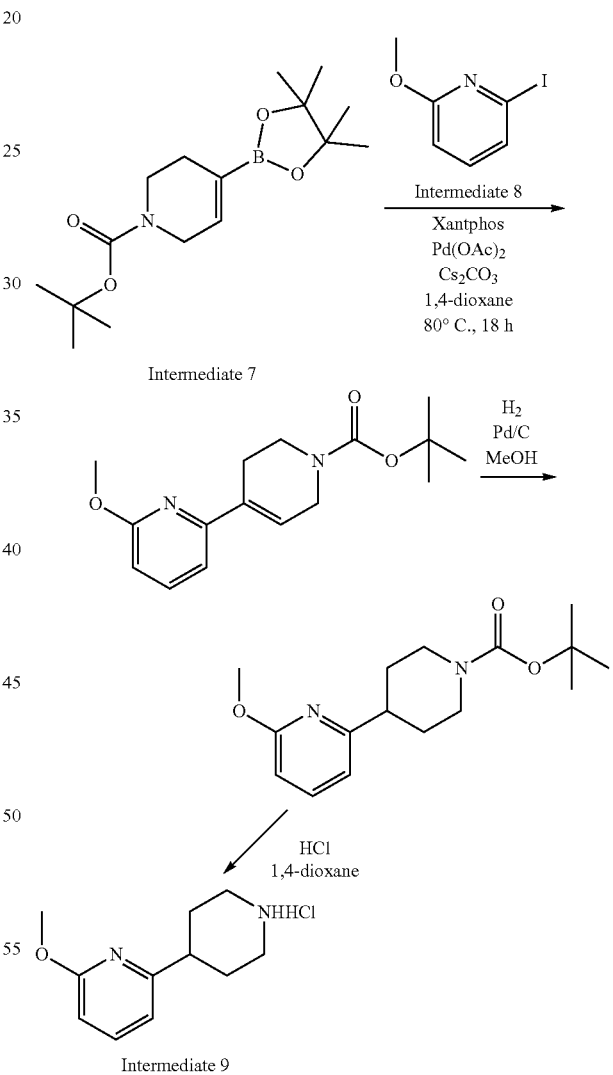

tert-Butyl 4-(4,4,5,5-tetramethyl-1,3,2-dioxaborolan-2-yl)-3,6-dihydropyridine-1(2H)-carboxylate (Intermediate 7) (395 mg, 1.28 mmol) and $Cs_2CO_3$ (1.03 g, 3.19 mmol) were added to a solution of 2-iodo-6-methoxypyridine (Intermediate 8) (300 mg, 1.28 mmol) in 1,4-dioxane (10 mL) and the resulting mixture was degassed under a nitrogen atmosphere for 20 min. (9,9-Dimethyl-9H-xanthene-4,5-diyl)bis(diphenylphosphane) (Xantphos, 36 mg, 0.06 mmol) and palladium(II) acetate (29 mg, 0.13 mmol) were added and the resulting reaction mixture was stirred at 80° C. for 18 h. The solvents were removed in-vacuo and residue was partitioned between H₂O (80 mL) and EtOAc (60 mL). The aqueous layer was further extracted with EtOAc (60 mL) and the combined organic layers were dried (Na₂SO₄) and the solvent was removed in-vacuo. The residue was purified by column chromatography (normal phase neutral activated alumina, 10% to 12% EtOAc in hexane) to give tert-butyl 6-methoxy-3',6'-dihydro-2,4'-bipyridine-1'(2'H)-carboxylate (310 mg, 84%) as a gum.

LCMS (System 3, Method D): m/z 291 (M+H)⁺ (ESI+ve), at 5.73 min, 202 nm. 10% Palladium on carbon (50% moisture, 100 mg) was added to a solution of tert-butyl 6-methoxy-3',6'-dihydro-2,4'-bipyridine-1'(2'H)-carboxylate (300 mg, 1.03 mmol) in MeOH (20 mL) and the resulting mixture was stirred under an atmosphere of hydrogen (1 atm pressure) at 70° C. for 40 h. The reaction mixture was filtered through Celite and the filtrate was concentrated in-vacuo. The crude product was triturated with pentane to give tert-butyl 4-(6-methoxypyridin-2-yl)piperidine-1-carboxylate (240 mg, 79%) as a gum.

LCMS (System 3, Method D): m/z 293 (M+H)⁺ (ESI+ve), at 5.05 min, 202 nm.

tert-Butyl 4-(6-methoxypyridin-2-yl)piperidine-1-carboxylate (240 mg, 0.82 mmol) was dissolved in 1,4-dioxane (5 mL) and cooled to 0° C. HCl solution in 1,4-dioxane (4 M, 5 mL) was added drop wise and the resulting reaction mixture was stirred at 25° C. for 8 h. The solvents were removed in-vacuo, and the residue was purified by trituration with pentane (3×2 mL) to give 2-methoxy-6-(piperidin-4-yl)pyridine hydrochloride (Intermediate 9) (130 mg, 82%) as a solid.

The data for Intermediate 9 are in Table 2.

Route 3

Typical Procedure for the Preparation of Piperidines, as Exemplified by the Preparation of Intermediate 21, N-(2-methylpropyl)-N-(piperidin-4-yl)acetamide Hydrochloride

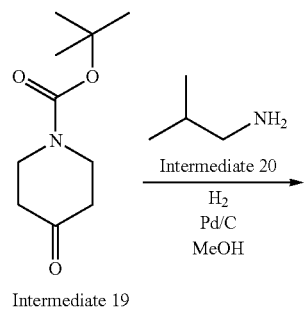

Intermediate 19    Intermediate 20

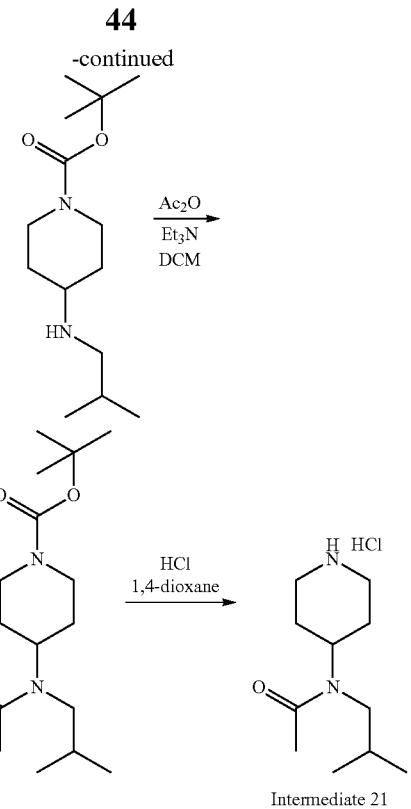

Intermediate 21 tert-Butyl 4-oxopiperidine-1-carboxylate (Intermediate 19) (5.0 g, 25.1 mmol) was dissolved in MeOH (50 mL) and 2-methylpropan-1-amine (Intermediate 20) (1.83 g, 25.1 mmol) was added. 10% Palladium hydroxide on carbon (50% moisture, 500 mg) was then added, and the resulting reaction mixture was stirred under an atmosphere of hydrogen (1 atm pressure) at 25° C. for 17 h. The mixture was filtered through Celite and the filtrate was concentrated in-vacuo to give tert-butyl 4-[(2-methylpropyl)amino]piperidine-1-carboxylate (5.0 g, 78%) as a gum.

LCMS (System 3, Method D): m/z 257 (M+H)⁺ (ESI+ve), at 3.39 min, 202 nm.

tert-Butyl 4-[(2-methylpropyl)amino]piperidine-1-carboxylate (5.0 g, 19.5 mmol) was dissolved in DCM (50 mL) and cooled to 0° C. Triethylamine (2.7 mL, 19.5 mmol) was added drop wise at 0-5° C. and the mixture was stirred at 0-5° C. for 10 min. Acetic anhydride (2.3 g, 23.4 mmol) was then added drop wise at 0-5° C., and the resulting reaction mixture was stirred at 25° C. for 2 h. The solvents were removed in-vacuo to give tert-butyl 4-[acetyl(2-methylpropyl)amino]piperidine-1-carboxylate (5.5 g, 89%) as a liquid.

LCMS (System 3, Method D): m/z 597 (2M+H)+, 284 (M-Me+H)⁺ (ESI+ve), at 4.03 min, 202 nm.

tert-butyl 4-[acetyl(2-methylpropyl)amino]piperidine-1-carboxylate (5.0 g, 15.8 mmol) was slowly dissolved in HCl solution in 1,4-dioxane (4 M, 50 mL), then the resulting mixture was stirred at 25° C. for 16 h. The solvents were removed in-vacuo, and the residue was purified by trituration with diethyl ether (3×250 mL) to give N-(2-methylpropyl)-N-(piperidin-4-yl)acetamide hydrochloride (Intermediate 21) (3.0 g, 88%) as a gum.

The data for Intermediate 21 are in Table 2.

Route 4

Typical Procedure for the Preparation of Piperidines, as Exemplified by the Preparation of Intermediate 23, N-(2,2-dimethylpropyl)-N-(piperidin-4-yl)acetamide Trifluoroacetate

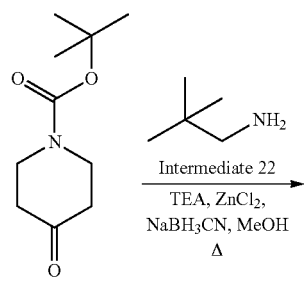

Intermediate 19

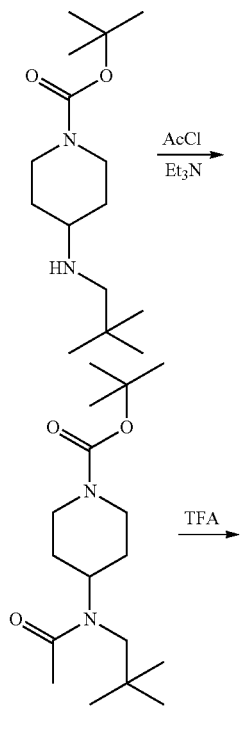

Intermediate 23 tert-Butyl 4-oxopiperidine-1-carboxylate (Intermediate 19) (3.0 g, 15.0 mmol), 2,2-dimethylpropan-1-amine (Intermediate 22) (1.5 g, 18 mmol), triethylamine (6.2 mL, 45 mmol) and ZnCl₂ (0.7 mL, 0.07 mmol) were dissolved in MeOH (30 mL) and the reaction mixture was stirred at 65° C. for 6 h. To this was then added NaBH₃CN (2.8 g, 45 mmol) portion wise at 0° C. The resulting reaction mixture was stirred at 25° C. for 17 h. The solvents were removed in-vacuo, and the residue was partitioned between H₂O (100 mL) and DCM (80 mL). The aqueous layer was further extracted with DCM (2×80 mL) and the combined organic phases were dried (Na₂SO₄) and concentrated in-vacuo to give tert-butyl 4-[(2,2-dimethylpropyl)amino]piperidine-1-carboxylate (3.5 g, 88%) as a yellow gum.

LCMS (System 3, Method D): m/z 271 (M+H)⁺, (ESI+ ve), at 4.22 min, 202 nm.

tert-Butyl 4-[(2,2-dimethylpropyl)amino]piperidine-1-carboxylate (3.5 g, 12 mmol) and triethylamine (5.3 mL, 30 mmol) were dissolved in DCM (20 mL) under nitrogen and stirred at 0° C. for 10 min. Acetyl chloride (1.3 mL, 19 mmol) was then added drop wise at 0-10° C. and the mixture was stirred at 25° C. for 2 h. The reaction mixture was partitioned between H₂O (150 mL) and EtOAc (120 mL). The aqueous layer was further extracted with EtOAc (2×120 mL) and the combined organic phases were dried (Na₂SO₄) and concentrated in-vacuo to give the crude product, which was purified by column chromatography (normal phase silica, 0 to 20% EtOAc in hexane to give tert-butyl 4-[acetyl(2,2-dimethylpropyl)amino]piperidine-1-carboxylate (3.1 g, 76%) as a yellow gum.

LCMS (System 3, Method D): m/z 313 (M+H)⁺, (ESI+ ve), at 4.41 min, 202 nm.

To a solution of tert-butyl 4-[acetyl(2,2-dimethylpropyl)amino]piperidine-1-carboxylate (3.1 g, 9 mmol) in DCM (14 mL) at 0° C. was added drop wise TFA (7.0 mL). The reaction was stirred at 25° C. for 6 h. The solvents were removed in-vacuo, and the residue was purified by triturating with pentane (3×1 mL) to give N-(2,2-dimethylpropyl)-N-(piperidin-4-yl)acetamide trifluoroacetate (Intermediate 23) (1.8 g, 86%) as a yellow gum.

The data for Intermediate 23 are in Table 2.

Route 5

Typical Procedure for the Preparation of Piperidines, as Exemplified by the Preparation of Intermediate 33, 1-(piperidin-4-yl)azepan-2-one Hydrochloride

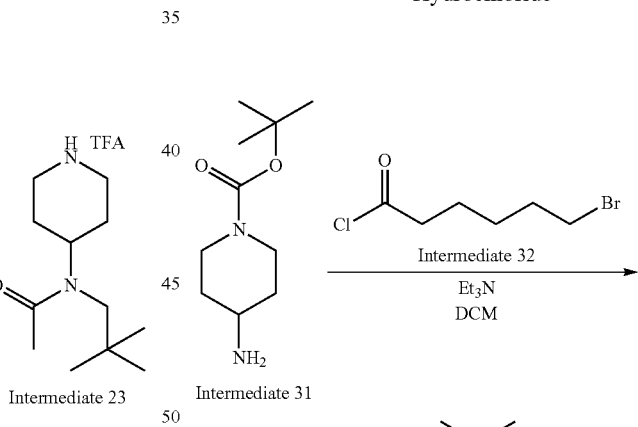

Intermediate 31

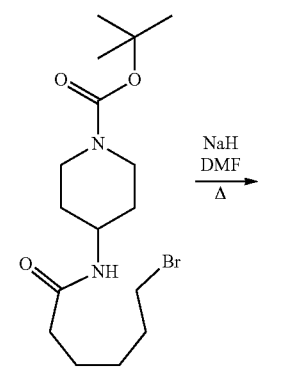

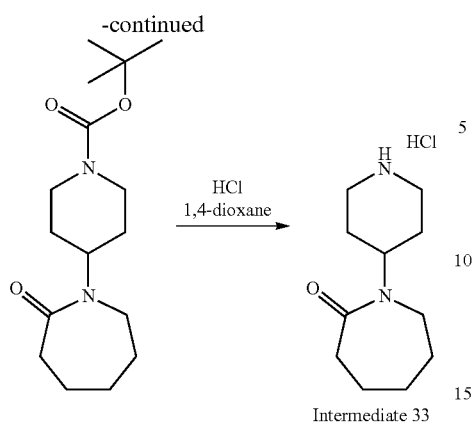

Intermediate 33

General Synthetic Procedures:
Route A

Typical Procedure for the Preparation of Piperidines as Exemplified by the Preparation of Example 1-1, Ethyl 7-[4-(1H-pyrazol-1-yl)piperidin-1-yl]-3-oxa-9-azabicyclo[3.3.1]nonane-9-carboxylate

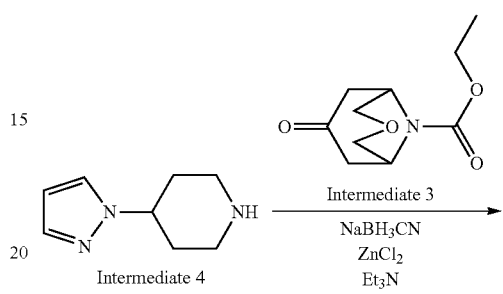

Example 1-1 tert-Butyl 4-aminopiperidine-1-carboxylate (Intermediate 31) (5.0 g, 25.0 mmol), was dissolved in DCM (50 mL) and triethylamine (4.17 mL, 30.0 mmol) was added. The mixture was cooled to 0° C. and then 6-bromohexanoyl chloride (Intermediate 32) (6.4 g, 30.0 mmol) was added. The resulting reaction mixture was stirred at 25° C. for 2 h and then the mixture was partitioned between H$_2$O (100 mL) and EtOAc (100 mL). The aqueous layer was further extracted with EtOAc (2×25 mL), the combined organic layers were dried (Na$_2$SO$_4$) and the solvent was removed in-vacuo to give tert-butyl 4-[(6-bromohexanoyl)amino]piperidine-1-carboxylate (5.5 g, 78%) as a solid.

LCMS (System 3, Method D): m/z 375/377 (M−H)$^−$, (ESI−ve), at 4.10 min, 202 nm.

tert-Butyl 4-[(6-bromohexanoyl)amino]piperidine-1-carboxylate (5.0 g, 13.2 mmol) was dissolved in DMF (100 mL) and NaH suspension in mineral oil (60%, 638 mg, 15.9 mmol) was added portion wise at 0-5° C. The reaction mixture was then heated to 80° C. and stirred for 2 h. The reaction mixture was partitioned between H$_2$O (100 mL) and EtOAc (100 mL) and the aqueous layer was further extracted with EtOAc (2×25 mL). The combined organic layers were dried (Na$_2$SO$_4$), the solvent was removed in-vacuo, and the crude product was purified by column chromatography (silica 60-120 mesh, 0% to 18% EtOAc in hexane) to give tert-butyl 4-(2-oxoazepan-1-yl)piperidine-1-carboxylate (1.0 g, 25%) as a gum.

LCMS (System 3, Method D): m/z 297 (M+H)$^+$, 241 (M−56+H)$^+$ (ESI+ve), at 3.73 min, 202 nm.

tert-Butyl 4-(2-oxoazepan-1-yl)piperidine-1-carboxylate (1.0 g, 3.37 mmol) was dissolved in HCl solution in 1,4-dioxane (4 M, 10 mL) and the resulting reaction mixture was stirred at 25° C. for 16 h. The solvents were removed in-vacuo and the residue was purified by trituration with diethyl ether (3×250 mL) to give 1-(piperidin-4-yl)azepan-2-one hydrochloride (Intermediate 33) (450 mg, 68%) as a gum.

The data for Intermediate 33 are in Table 2.

4-(1H-Pyrazol-1-yl)piperidine (Intermediate 4) (150 mg, 0.9 mmol), ethyl 7-oxo-3-oxa-9-azabicyclo[3.3.1]nonane-9-carboxylate (Intermediate 3) (232 mg, 1.0 mmol), triethylamine (499 mg, 4.9 mmol) and zinc chloride solution (1 M in diethyl ether, 0.03 mL, 0.03 mmol) were dissolved in MeOH (5 mL) under nitrogen and stirred for 8 h at 50-60° C. After 8 h, NaBH$_3$CN (184 mg, 2.9 mmol) was added portion wise at 0-10° C. and the resulting mixture was stirred at 50-60° C. until the reaction was complete. The reaction mixture was partitioned between H$_2$O (20 mL) and EtOAc (30 mL), and the aqueous layer was further extracted with EtOAc (2×30 mL). The combined organic layers were dried (Na$_2$SO$_4$) and the solvent was removed in-vacuo to give the crude product, which was purified using purification method A to give ethyl 7-[4-(1H-pyrazol-1-yl)piperidin-1-yl]-3-oxa-9-azabicyclo[3.3.1]nonane-9-carboxylate, Example 1-1 Isomer 1 (11 mg, 4%) as a gum and ethyl 7-[4-(1H-pyrazol-1-yl)piperidin-1-yl]-3-oxa-9-azabicyclo[3.3.1]nonane-9-carboxylate, Isomer 2 (39 mg, 12%) as a gum.

The data for Example 1-1 Isomer 1 are in Table 3.

Route B

Typical Procedure for the Preparation of Pyridones from Methoxy Pyridines as Exemplified by the Preparation of Example 2-3, ethyl 7-[4-(2-oxo-1,2-dihydropyridin-3-yl)piperidin-1-yl]-3-oxa-9-azabicyclo[3.3.1]nonane-9-carboxylate

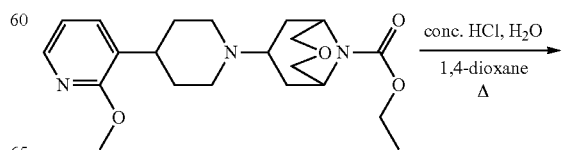

Example 2-2

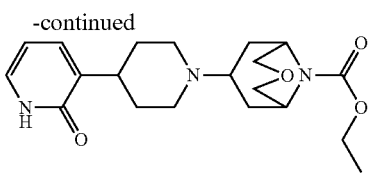

Example 2-3

To a stirred solution of ethyl 7-[4-(2-methoxypyridin-3-yl)piperidin-1-yl]-3-oxa-9-azabicyclo[3.3.1]nonane-9-carboxylate (Example 2-2) as a mixture of isomers (0.09 g, 2.31 mmol) in 1,4-dioxane (1.5 mL), were added H$_2$O (1 mL) and conc. HCl (1 mL) and then the reaction mixture was stirred at 100° C. for 16 h. The solvents were removed in-vacuo, the residue was partitioned between H$_2$O (2 mL) and EtOAc (10 mL), and the aqueous layer was further extracted with EtOAc (2×5 mL). The combined organic layers were dried (Na$_2$SO$_4$), the solvent was removed in-vacuo and the residue was purified using purification method H followed by purification method I to give ethyl 7-[4-(2-oxo-1,2-dihydropyridin-3-yl)piperidin-1-yl]-3-oxa-9-azabicyclo[3.3.1]nonane-9-carboxylate, Example 2-3 Isomer 1 (2 mg, 2%) as a gum and ethyl 7-[4-(2-oxo-1,2-dihydropyridin-3-yl)piperidin-1-yl]-3-oxa-9-azabicyclo[3.3.1]nonane-9-carboxylate, Example 2-3 Isomer 2 (20 mg, 23%) as a gum.

The data for Example 2-3 Isomer 1 and Isomer 2 are in Table 3.

Route C

Typical Procedure for the Preparation of Piperidine-4-Carboxamides as Exemplified by the Preparation of Example 7-1, ethyl 7-{4-[(1-methylcyclobutyl)carbamoyl]piperidin-1-yl}-3-oxa-9-azabicyclo[3.3.1]nonane-9-carboxylate

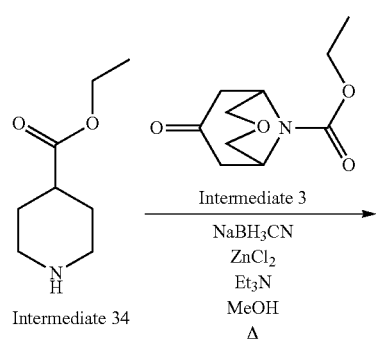

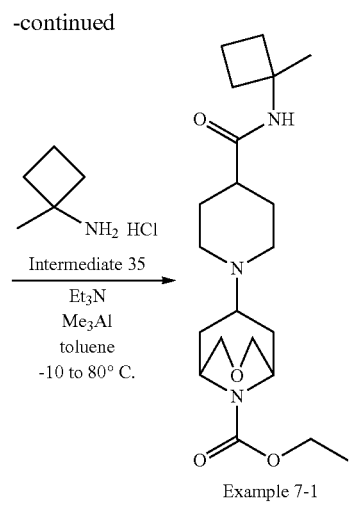

Example 7-1

Ethyl piperidine-4-carboxylate (Intermediate 34) (1.0 g, 6.36 mmol), ethyl 7-oxo-3-oxa-9-azabicyclo[3.3.1]nonane-9-carboxylate (Intermediate 3) (1.30 g, 6.36 mmol), triethylamine (2.7 mL, 19.1 mmol) and ZnCl$_2$ (86 mg, 0.63 mmol) were dissolved in MeOH (20 mL) and the mixture was stirred at 70° C. for 8 h. The reaction mixture was then cooled to 0° C. and NaBH$_3$CN (1.20 g, 19.1 mmol) was added portion wise. The resulting mixture was stirred at 70° C. for 150 h and then the solvents were removed in-vacuo. The residue was partitioned between H$_2$O (150 mL) and EtOAc (120 mL) and the aqueous layer was further extracted with EtOAc (2×120 mL). The combined organic layers were dried (Na$_2$SO$_4$), the solvent was removed in-vacuo, and the residue was purified by column chromatography (normal phase neutral activated alumina, 20% to 80% EtOAc in hexane) to give ethyl 7-[4-(ethoxycarbonyl)piperidin-1-yl]-3-oxa-9-azabicyclo[3.3.1]nonane-9-carboxylate (800 mg, 36%) as a gum.

LCMS (System 3, Method D): m/z 341 (M−14+H)$^+$, (ESI+ve), at 2.87 min, 202 nm.

1-Methylcyclobutan-1-amine hydrochloride (Intermediate 35) (102 mg, 0.85 mmol) was dissolved in toluene (10 mL), triethylamine (0.3 mL, 1.69 mmol) was added and the mixture was cooled to −10° C. Trimethylaluminium solution in toluene (2 M, 0.8 mL, 1.69 mmol) was added and the reaction mixture was stirred at −10° C. for 20 min. Ethyl 7-[4-(ethoxycarbonyl)piperidin-1-yl]-3-oxa-9-azabicyclo[3.3.1]nonane-9-carboxylate (200 mg, 0.56 mmol) was then added at −10° C. and the resulting mixture was stirred at 80° C. for 18 h. The solvents were removed in-vacuo, and the residue was partitioned between H$_2$O (80 mL) and DCM (60 mL). The aqueous layer was further extracted with DCM (2×60 mL) and the combined organic layers were dried (Na$_2$SO$_4$), and the solvent was removed in-vacuo. The residue (230 mg) was purified using purification method AH followed by purification method AI to give ethyl 7-{4-[(1-methylcyclobutyl)carbamoyl]piperidin-1-yl}-3-oxa-9-azabicyclo[3.3.1]nonane-9-carboxylate, Example 7-1 Isomer 1 (6 mg, 3%) as a gum and ethyl 7-{4-[(1-methylcyclobutyl)carbamoyl]piperidin-1-yl}-3-oxa-9-azabicyclo[3.3.1]nonane-9-carboxylate, Example 7-1 Isomer 2 (23 mg, 10%) as a gum.

The data for Example 7-1 Isomer 1 and Isomer 2 are in Table 3.

TABLE 2

Starting Materials and Intermediates
Table 2

| Intermediate Number | Name | Synthetic Route | Intermediates Used | Data |
|---|---|---|---|---|
| 1 | tert-Butyl 7-oxo-3-oxa-9-azabicyclo[3.3.1]nonane-9-carboxylate | — | — | Commercially available, CAS: 280761-97-9 |
| 2 | Ethyl chloroformate | — | — | Commercially available, CAS: 541-41-3 |
| 3 | Ethyl 7-oxo-3-oxa-9-azabicyclo[3.3.1]nonane-9-carboxylate | 1 | 1 and 2 | LCMS (System 2, Method A): m/z 214 $(M + H)^+$ (ESI + ve), at 1.53 min, 202 nm |
| 4 | 4-(1H-Pyrazol-1-yl)piperidine | — | — | Commercially available, CAS: 762240-09-5 |
| 5 | 4-(4-Chloro-1H-pyrazol-1-yl)piperidine | — | — | Commercially available, CAS: 1251305-58-4 |
| 6 | 4-(4-methyl-1H-pyrazol-1-yl)piperidine | — | — | Commercially available, CAS: 1211520-55-6 |
| 7 | tert-Butyl 4-(4,4,5,5-tetramethyl-1,3,2-dioxaborolan-2-yl)-3,6-dihydropyridine-1(2H)-carboxylate | — | — | Commercially available, CAS: 286961-14-6 |
| 8 | 2-Iodo-6-methoxypyridine | — | — | Commercially available, CAS: 182275-70-3 |
| 9 | 2-Methoxy-6-(piperidin-4-yl)pyridine hydrochloride | 2 | 7 and 8 | LCMS (System 3, Method D): m/z 193 $(M + H)^+$ (ESI + ve), at 2.23 min, 202 nm See WO2015118342 |
| 10 | 3-Iodo-2-methoxypyridine | — | — | Commercially available, CAS: 112197-15-6 |
| 11 | 2-Methoxy-3-(piperidin-4-yl)pyridine hydrochloride | 2 | 7 and 10 | LCMS (System 2, Method A): m/z 193 $(M + H)^+$ (ESI + ve), at 1.42 min, 273 nm See WO2015118342 |
| 12 | 4-(Pyridin-2-yl)piperidine-4-carbonitrile | — | — | Commercially available, CAS: 767263-33-2 |
| 13 | [(2R)-4,4-Difluoro-1-(piperidin-4-yl)pyrrolidin-2-yl]methanol | — | — | See WO2017021728 |
| 14 | 6-Azaspiro[2.5]octane | — | — | Commercially available, CAS: 872-64-0 |
| 15 | 2,8-Diazaspiro[4.5]decan-3-one | — | — | Commercially available, CAS: 561314-57-6 |
| 16 | 1-Oxa-3,8-diazaspiro[4.5]decan-2-one | — | — | Commercially available, CAS: 5052-95-9 |
| 17 | 4-Ethyl-1-oxa-3,8-diazaspiro[4.5]decan-2-one | — | — | See WO2016147011 |
| 18 | Spiro[indole-3,4'-piperidin]-2(1H)-one | — | — | Commercially available, CAS: 252882-61-4 |
| 19 | tert-Butyl 4-oxopiperidine-1-carboxylate | — | — | Commercially available, CAS: 79099-07-3 |
| 20 | 2-Methylpropan-1-amine | — | — | Commercially available, CAS: 78-81-9 |
| 21 | N-(2-Methylpropyl)-N-(piperidin-4-yl)acetamide hydrochloride | 3 | 19 and 20 | LCMS (System 1, Method B): m/z 199 $(M + H)^+$ (ESI + ve), at 4.09 min, 220 nm |
| 22 | 2,2-Dimethylpropan-1-amine | — | — | Commercially available, CAS: 5813-64-9 |
| 23 | N-(2,2-Dimethylpropyl)-N-(piperidin-4-yl)acetamide trifluoroacetate | 4 | 19 and 22 | LCMS (System 3, Method D): m/z 213 $(M + H)^+$, (ESI + ve), at 2.24 min, 202 nm |
| 24 | 1-(1-Methylcyclopropyl)methanamine | — | — | Commercially available, CAS: 98137-40-7 |
| 25 | N-[(1-methylcyclopropyl)methyl]-N-(piperidin-4-yl)acetamide trifluoroacetate | 4 | 19 and 24 | LCMS (System 3, Method D): m/z 211 $(M + H)^+$, (ESI + ve), at 2.00 min, 202 nm |
| 26 | 1-(1-Methylcyclobutyl)methanamine | — | — | Commercially available, CAS: 933722-69-1 |
| 27 | N-[(1-methylcyclobutyl)methyl]-N-(piperidin-4-yl)acetamide trifluoroacetate | 4 | 19 and 26 | LCMS (System 3, Method D): m/z 225 $(M + H)^+$, (ESI + ve), at 2.24 min, 202 nm |
| 28 | 1-Phenylmethanamine | — | — | Commercially available, CAS: 100-46-9 |
| 29 | N-Benzyl-N-(piperidin-4-yl)acetamide hydrochloride | 3 | 19 and 28 | LCMS (System 3, Method D): m/z 233 $(M + H)^+$ (ESI + ve), at 1.99 min, 202 nm |
| 30 | [1,4'-bipiperidin]-2-one | — | — | Commercially available, CAS: 159874-26-7 |
| 31 | tert-Butyl 4-aminopiperidine-1-carboxylate | — | — | Commercially available, CAS: 87120-72-7 |

TABLE 2-continued

Starting Materials and Intermediates
Table 2

| Intermediate Number | Name | Synthetic Route | Intermediates Used | Data |
|---|---|---|---|---|
| 32 | 6-Bromohexanoyl chloride | — | — | Commercially available, CAS: 22809-37-6 |
| 33 | 1-(Piperidin-4-yl)azepan-2-one hydrochloride | 5 | 31 and 32 | LCMS (System 3, Method D): m/z 197 (M + H)$^+$, 393 (2M + H)$^+$, (ESI + ve), at 1.55 min, 202 nm |
| 34 | Ethyl piperidine-4-carboxylate | — | — | Commercially available, CAS: 1126-09-6 |
| 35 | 1-Methylcyclobutan-1-amine hydrochloride | — | — | Commercially available, CAS: 174886-05-6 |
| 36 | 1-Cyclobutylmethanamine | — | — | Commercially available, CAS: 4415-83-2 |
| 37 | Azepane | — | — | Commercially available, CAS: 111-49-9 |
| 38 | Methyl chloroformate | — | — | Commercially available, CAS: 79-22-1 |
| 39 | Methyl 7-oxo-3-oxa-9-azabicyclo[3.3.1]nonane-9-carboxylate | 1 | 1 and 38 | LCMS (System 3, Method D): m/z 200 (M + H)$^+$ (ESI + ve), at 1.68 min, 202 nm |

TABLE 3

NMR and LCMS properties and the methods used to prepare and purify compounds represented by Examples 1-8-2

| Ex. No. | Name | Synthetic Method and Intermediates Used | Purification Method | $^1$H NMR | LCMS Analysis System and Method | LCMS data |
|---|---|---|---|---|---|---|
| 1-1 | Isomer 1: Ethyl 7-[4-(1H-pyrazol-1-yl)piperidin-1-yl]-3-oxa-9-azabicyclo[3.3.1]nonane-9-carboxylate | A 3 and 4 | A | $^1$H NMR (400 MHz, METHANOL-d$_4$) δ ppm 1.24-1.32 (m, 3 H), 1.62-1.77 (m, 2 H), 1.94-2.07 (m, 2 H), 2.07-2.18 (m, 2 H), 2.23-2.39 (m, 3 H), 2.39-2.52 (m, 2 H), 3.05-3.16 (m, 2 H), 3.48-3.57 (m, 2 H), 3.57-3.68 (m, 2 H), 4.10-4.21 (m, 3 H), 4.21-4.34 (m, 2 H), 6.21-6.42 (m, 1 H), 7.42-7.57 (m, 1 H), 7.63-7.79 (m, 1 H) | 1 D | m/z 349 (M + H)$^+$ (ESI$^+$), at 3.28 min, 202 nm |
| 1-2 | Isomer 1: Ethyl 7-[4-(4-chloro-1H-pyrazol-1-yl)piperidin-1-yl]-3-oxa-9-azabicyclo[3.3.1]nonane-9-carboxylate | A 3 and 5 | B | $^1$H NMR (400 MHz, METHANOL-d$_4$) δ ppm 1.22-1.33 (m, 3 H), 1.61-1.76 (m, 2 H), 1.93-2.05 (m, 2 H), 2.05-2.13 (m, 2 H), 2.23-2.37 (m, 3 H), 2.37-2.48 (m, 2 H), 3.03-3.16 (m, 2 H), 3.47-3.56 (m, 2 H), 3.57-3.66 (m, 2 H), 4.07-4.20 (m, 3 H), 4.20-4.30 (m, 2 H), 7.43 (s, 1 H), 7.77 (s, 1 H) | 3 D | m/z 383, 385 (M + H)$^+$ (ESI$^+$), at 3.31 min, 202 nm |
| 1-2 | Isomer 2: Ethyl 7-[4-(4-chloro-1H-pyrazol-1-yl)piperidin-1-yl]-3-oxa-9-azabicyclo[3.3.1]nonane-9-carboxylate | A 3 and 5 | B | $^1$H NMR (400 MHz, METHANOL-d$_4$) δ ppm 1.20-1.37 (m, 3 H), 1.65-1.81 (m, 2 H), 1.90-2.21 (m, 6 H), 2.25-2.42 (m, 2 H), 3.07-3.24 (m, 2 H), 3.61-3.78 (m, 3 H), 3.81-3.97 (m, 2 H), 4.06-4.30 (m, 5 H), 7.43 (s, 1 H), 7.78 (s, 1 H) | 3 D | m/z 383, 385 (M + H)$^+$ (ESI$^+$), at 3.32 min, 202 nm |
| 1-3 | Isomer 1: Ethyl 7-[4-(4-methyl-1H-pyrazol-1-yl)piperidin-1-yl]-3-oxa-9-azabicyclo[3.3.1]nonane-9-carboxylate | A 3 and 6 | C then D | $^1$H NMR (400 MHz, METHANOL-d$_4$) δ ppm 1.27 (t, J = 7.1 Hz, 3 H), 1.61-1.79 (m, 2 H), 1.87-2.17 (m, 6 H), 2.23-2.37 (m, 3 H), 2.37-2.51 (m, 2 H), 3.02-3.17 (m, 2 H), 3.47-3.72 (m, 5 H), 4.02-4.11 (m, 1 H), 4.15 (q, J = 7.1Hz, 2 H), 4.20-4.31 (m, 2 H), 7.26 (s, 1 H), 7.44 (s, 1 H) | 3 C | m/z 363 (M + H)$^+$ (ESI$^+$), at 3.04 min, 202 nm |
| 1-3 | Isomer 2: Ethyl 7-[4-(4-methyl-1H-pyrazol-1-yl)piperidin-1-yl]-3-oxa-9-azabicyclo[3.3.1]nonane-9-carboxylate | A 3 and 6 | C then D | $^1$H NMR (400 MHz, METHANOL-d$_4$) δ ppm 1.21-1.33 (m, 3 H), 1.65-1.78 (m, 2 H), 1.88-2.01 (m, 2 H), 2.02-2.16 (m, 7 H), 2.25-2.40 (m, 2 H), 3.06-3.21 (m, 2 H), 3.61-3.76 (m, 3 H), 3.80-3.92 (m, 2 H), 4.02-4.23 (m, 5 H), 7.26 (s, 1 H), 7.44 (s, 1 H) | 3 C | m/z 363 (M + H)$^+$ (ESI$^+$), at 2.98 min, 202 nm |
| 2-1 | Isomer 1: Ethyl 7-[4-(6-methoxypyridin-2-yl)piperidin-1-yl]-3-oxa-9-azabicyclo[3.3.1]nonane-9-carboxylate | A 3 and 9 | C then E | $^1$H NMR (400 MHz, METHANOL-d$_4$) δ ppm 1.21-1.37 (m, 3 H), 1.67-1.80 (m, 2 H), 1.83-1.98 (m, 4 H), 2.07-2.19 (m, 2 H), 2.20-2.35 (m, 2 H), 2.54-2.71 (m, 1 H), 3.09-3.21 (m, 2 H), 3.59-3.75 (m, 3 H), 3.79-3.95 (m, 5 H), 4.08-4.24 (m, 4 H), 6.50-6.63 (m, 1 H), 6.73-6.86 (m, 1 H), 7.47-7.61 (m, 1 H) | 3 D | m/z 390 (M + H)$^+$ (ESI$^+$), at 3.62 min, 202 nm |

TABLE 3-continued

NMR and LCMS properties and the methods used to prepare and purify compounds represented by Examples 1-8-2

| Ex. No. | Name | Synthetic Method and Intermediates Used | Purification Method | $^1$H NMR | LCMS Analysis System and Method | LCMS data |
|---|---|---|---|---|---|---|
| 2-1 | Isomer 2: Ethyl 7-[4-(6-methoxypyridin-2-yl)piperidin-1-yl]-3-oxa-9-azabicyclo[3.3.1]nonane-9-carboxylate | A 3 and 9 | C then E | $^1$H NMR (400 MHz, METHANOL-$d_4$) δ ppm 1.23-1.35 (m, 3 H), 1.66-1.79 (m, 2 H), 1.84-1.99 (m, 4 H), 2.22-2.47 (m, 5 H), 2.56-2.69 (m, 1 H), 3.04-3.18 (m, 2 H), 3.49-3.57 (m, 2 H), 3.58-3.68 (m, 2 H), 3.89 (s, 3 H), 4.11-4.21 (m, 2 H), 4.22-4.32 (m, 2 H), 6.52-6.63 (m, 1 H), 6.75-6.83 (m, 1 H), 7.50-7.60 (m, 1 H) | 3 D | m/z 390 (M + H)$^+$ (ESI$^+$), at 3.52 min, 202 nm |
| 2-2 | Isomer 1: Ethyl 7-[4-(2-methoxypyridin-3-yl)piperidin-1-yl]-3-oxa-9-azabicyclo[3.3.1]nonane-9-carboxylate | A 3 and 11 | F then G | $^1$H NMR (400 MHz, METHANOL-$d_4$) δ ppm 1.21-1.39 (m, 3 H), 1.64-1.79 (m, 4 H), 1.80-1.92 (m, 2 H), 2.20-2.48 (m, 5 H), 2.77-2.91 (m, 1 H), 3.03-3.16 (m, 2 H), 3.47-3.73 (m, 4 H), 3.92 (s, 3 H), 4.11-4.21 (m, 2 H), 4.22-4.32 (m, 2 H), 6.82-6.99 (m, 1 H), 7.49-7.59 (m, 1 H), 7.89-8.01 (m, 1 H) | 3 D | m/z 390 (M + H)$^+$ (ESI$^+$), at 3.31 min, 272 nm |
| 2-2 | Isomer 2: Ethyl 7-[4-(2-methoxypyridin-3-yl)piperidin-1-yl]-3-oxa-9-azabicyclo[3.3.1]nonane-9-carboxylate | A 3 and 11 | F then G | $^1$H NMR (400 MHz, METHANOL-$d_4$) δ ppm 1.24-1.34 (m, 3 H), 1.63-1.80 (m, 4 H), 1.82-1.93 (m, 2 H), 2.08-2.20 (m, 2 H), 2.23-2.36 (m, 2 H), 2.78-2.91 (m, 1 H), 3.12-3.24 (m, 2 H), 3.62-3.76 (m, 3 H), 3.81-3.99 (m, 5 H), 4.09-4.23 (m, 4 H), 6.85-6.97 (m, 1 H), 7.49-7.60 (m, 1 H), 7.92-8.01 (m, 1 H) | 3 D | m/z 390 (M + H)$^+$ (ESI$^+$), at 3.23 min, 202 nm |
| 2-3 | Isomer 1: Ethyl 7-[4-(2-oxo-1,2-dihydropyridin-3-yl)piperidin-1-yl]-3-oxa-9-azabicyclo[3.3.1]nonane-9-carboxylate | B Example 2-2 | H then I | $^1$H NMR (400 MHz, METHANOL-$d_4$) δ ppm 1.22-1.40 (m, 3 H), 1.52-1.77 (m, 4 H), 1.84-1.96 (m, 2 H), 2.38 (d, J = 11.7 Hz, 4 H), 2.74-2.87 (m, 1 H), 3.03-3.16 (m, 2 H), 3.47-3.73 (m, 5 H), 4.11-4.21 (m, 2 H), 4.22-4.32 (m, 2 H), 6.35-6.45 (m, 1 H), 7.26-7.34 (m, 1 H), 7.40-7.48 (m, 1 H) | 3 D | m/z 376 (M + H)$^+$ (ESI$^+$), at 2.27 min, 202 nm |
| 2-3 | Isomer 2: Ethyl 7-[4-(2-oxo-1,2-dihydropyridin-3-yl)piperidin-1-yl]-3-oxa-9-azabicyclo[3.3.1]nonane-9-carboxylate | B Example 2-2 | H then I | $^1$H NMR (400 MHz, METHANOL-$d_4$) δ ppm 1.22-1.35 (m, 3 H), 1.51-1.65 (m, 2 H), 1.68-1.81 (m, 2 H), 1.85-1.97 (m, 2 H), 2.08-2.19 (m, 2 H), 2.23-2.36 (m, 2 H), 2.75-2.89 (m, 1 H), 3.11-3.23 (m, 2 H), 3.63-3.74 (m, 3 H), 3.81-3.95 (m, 2 H), 4.09-4.24 (m, 4 H), 6.34-6.43 (m, 1 H), 7.23-7.32 (m, 1 H), 7.39-7.48 (m, 1 H) | 3 D | m/z 376 (M + H)$^+$ (ESI$^+$), at 2.20 min, 202 nm |
| 3-1 | Isomer 1: Ethyl 7-[4-cyano-4-(pyridin-2-yl)piperidin-1-yl]-3-oxa-9-azabicyclo[3.3.1]nonane-9-carboxylate | A 3 and 12 | J then K | $^1$H NMR (400 MHz, METHANOL-$d_4$) δ ppm 1.28 (t, J = 7.3 Hz, 3 H), 1.67-1.85 (m, 2 H), 2.13-2.45 (m, 7 H), 2.63-2.82 (m, 2 H), 3.05-3.20 (m, 2 H), 3.50-3.58 (m, 2 H), 3.59-3.74 (m, 2 H), 4.17 (q, J = 7.3 Hz, 2 H), 4.23-4.37 (m, 2 H), 7.28-7.48 (m, 1 H), 7.57-7.71 (m, 1 H), 7.82-7.95 (m, 1 H), 8.51-8.67 (m, 1 H) | 3 D | m/z 385 (M + H)$^+$ (ESI$^+$), at 3.33 min, 202 nm |
| 3-1 | Isomer 2: Ethyl 7-[4-cyano-4-(pyridin-2-yl)piperidin-1-yl]-3-oxa-9-azabicyclo[3.3.1]nonane-9-carboxylate | A 3 and 12 | J then K | $^1$H NMR (400 MHz, METHANOL-$d_4$) δ ppm 1.22-1.46 (m, 3 H), 1.67-1.86 (m, 2 H), 2.06-2.38 (m, 6 H), 2.49-2.72 (m, 2 H), 3.11-3.25 (m, 2 H), 3.63-4.00 (m, 5 H), 4.09-4.31 (m, 4 H), 7.26-7.47 (m, 1 H), 7.56-7.72 (m, 1 H), 7.81-7.94 (m, 1 H), 8.52-8.67 (m, 1 H) | 3 D | m/z 385 (M + H)$^+$ (ESI$^+$), at 3.33 min, 202 nm |
| 4-1 | Isomer 1: Ethyl 7-{4-[(2R)-4,4-difluoro-2-(hydroxymethyl)pyrrolidin-1-yl]piperidin-1-yl}-3-oxa-9-azabicyclo[3.3.1]nonane-9-carboxylate | A 3 and 13 | L then M | $^1$H NMR (400 MHz, METHANOL-$d_4$) δ ppm 1.20-1.38 (m, 3 H), 1.45-1.57 (m, 2 H), 1.61-1.72 (m, 2 H), 1.77-1.87 (m, 2 H), 2.10-2.41 (m, 7 H), 2.64-2.77 (m, 1 H), 2.94-3.11 (m, 3 H), 3.14-3.28 (m, 2 H), 3.45-3.68 (m, 6 H), 4.10-4.19 (m, 2 H), 4.19-4.29 (m, 2 H) | 1 D | m/z 418 (M + H)$^+$ (ESI$^+$), at 3.01 min, 202 nm |
| 4-1 | Isomer 2: Ethyl 7-{4-[(2R)-4,4-difluoro-2-(hydroxymethyl)pyrrolidin-1-yl]piperidin-1-yl}-3-oxa-9-azabicyclo[3.3.1]nonane-9-carboxylate | A 3 and 13 | L then M | $^1$H NMR (400 MHz, METHANOL-$d_4$) δ ppm 1.20-1.36 (m, 3 H), 1.42-1.60 (m, 2 H), 1.63-1.75 (m, 2 H), 1.77-1.88 (m, 2 H), 2.03-2.25 (m, 5 H), 2.26-2.43 (m, 1 H), 2.62-2.78 (m, 1 H), 3.01-3.14 (m, 3 H), 3.15-3.26 (m, 2 H), 3.44-3.73 (m, 5 H), 3.78-3.92 (m, 2 H), 4.05-4.23 (m, 4 H) | 1 D | m/z 418 (M + H)$^+$ (ESI$^+$), at 2.93 min, 202 nm |
| 5-1 | Isomer 1: Ethyl 7-(6-azaspiro[2.5]oct-6-yl)-3-oxa-9-azabicyclo[3.3.1]nonane-9-carboxylate | A 3 and 14 | N | $^1$H NMR (400 MHz, METHANOL-$d_4$) δ ppm 0.21-0.38 (m, 4 H), 1.21-1.33 (m, 3 H), 1.37-1.55 (m, 4 H), 1.66-1.83 (m, 2 H), 2.03-2.18 (m, 2 H), 2.53-2.74 (m, 4 H), 3.60-3.75 (m, 3 H), 3.79-3.93 (m, 2 H), 4.06-4.22 (m, 4 H) | 1 D | m/z 309 (M + H)$^+$ (ESI$^+$), at 3.46 min, 202 nm |

TABLE 3-continued

NMR and LCMS properties and the methods used to prepare and purify compounds represented by Examples 1-8-2

| Ex. No. | Name | Synthetic Method and Intermediates Used | Purification Method | $^1$H NMR | LCMS Analysis System and Method | LCMS data |
|---|---|---|---|---|---|---|
| 5-1 | Isomer 2: Ethyl 7-(6-azaspiro[2.5]oct-6-yl)-3-oxa-9-azabicyclo[3.3.1]nonane-9-carboxylate | A 3 and 14 | N | $^1$H NMR (400 MHz, METHANOL-d$_4$) δ ppm 0.24-0.36 (m, 4 H), 1.20-1.33 (m, 3 H), 1.37-1.54 (m, 4 H), 1.66-1.79 (m, 2 H), 2.20-2.40 (m, 3 H), 2.58-2.76 (m, 4 H), 3.47-3.55 (m, 2 H), 3.57-3.69 (m, 2 H), 4.10-4.19 (m, 2 H), 4.20-4.32 (m, 2 H) | 1 D | m/z 309 (M + H)$^+$ (ESI$^+$), at 3.61 min, 202 nm |
| 5-2 | Isomer 1: Ethyl 7-(3-oxo-2,8-diazaspiro[4.5]dec-8-yl)-3-oxa-9-azabicyclo[3.3.1]nonane-9-carboxylate | A 3 and 15 | O | $^1$H NMR (400 MHz, METHANOL-d$_4$) δ ppm 1.20-1.36 (m, 4 H), 1.60-1.76 (m, 6 H), 2.18-2.24 (m, 2 H), 2.27-2.39 (m, 2 H), 2.50-2.72 (m, 4 H), 3.16-3.22 (m, 2 H), 3.47-3.55 (m, 2 H), 3.56-3.67 (m, 2 H), 4.09-4.19 (m, 2 H), 4.20-4.31 (m, 2 H) | 1 D | m/z 352 (M + H)$^+$ (ESI$^+$), at 2.56 min, 202 nm |
| 5-2 | Isomer 2: Ethyl 7-(3-oxo-2,8-diazaspiro[4.5]dec-8-yl)-3-oxa-9-azabicyclo[3.3.1]nonane-9-carboxylate | A 3 and 15 | O | $^1$H NMR (400 MHz, METHANOL-d$_4$) δ ppm 1.17-1.36 (m, 4 H), 1.56-1.79 (m, 5 H), 2.01-2.15 (m, 2 H), 2.18-2.27 (m, 2 H), 2.42-2.73 (m, 4 H), 3.11-3.25 (m, 2 H), 3.51-3.75 (m, 3 H), 3.77-3.94 (m, 2 H), 4.02-4.25 (m, 4 H) | 1 D | m/z 352 (M + H)$^+$ (ESI$^+$), at 2.56 min, 202 nm |
| 5-3 | Isomer 1: Ethyl 7-(2-oxo-1-oxa-3,8-diazaspiro[4.5]dec-8-yl)-3-oxa-9-azabicyclo[3.3.1]nonane-9-carboxylate | A 3 and 16 | P then Q | $^1$H NMR (400 MHz, METHANOL-d$_4$) δ ppm 1.22-1.33 (m, 3 H), 1.62-1.74 (m, 2 H), 1.77-1.88 (m, 2 H), 1.92-2.03 (m, 2 H), 2.23-2.37 (m, 3 H), 2.65-2.77 (m, 4 H), 3.34-3.38 (m, 2 H), 3.47-3.56 (m, 2 H), 3.57-3.67 (m, 2 H), 4.10-4.20 (m, 2 H), 4.21-4.31 (m, 2 H) | 3 D | m/z 354 (M + H)$^+$ (ESI$^+$), at 2.10 min, 202 nm |
| 5-3 | Isomer 2: Ethyl 7-(2-oxo-1-oxa-3,8-diazaspiro[4.5]dec-8-yl)-3-oxa-9-azabicyclo[3.3.1]nonane-9-carboxylate | A 3 and 6 | P then Q | $^1$H NMR (400 MHz, METHANOL-d$_4$) δ ppm 1.22-1.33 (m, 3 H), 1.63-1.76 (m, 2 H), 1.77-1.88 (m, 2 H), 1.91-2.02 (m, 2 H), 2.06-2.15 (m, 2 H), 2.56-2.81 (m, 4 H), 3.34-3.39 (m, 2 H), 3.62-3.73 (m, 3 H), 3.79-3.92 (m, 2 H), 4.08-4.21 (m, 4 H) | 3 D | m/z 354 (M + H)$^+$ (ESI$^+$), at 2.21 min, 202 nm |
| 5-4 | Isomer 1a: Ethyl 7-(4-ethyl-2-oxo-1-oxa-3,8-diazaspiro[4.5]dec-8-yl)-3-oxa-9-azabicyclo[3.3.1]nonane-9-carboxylate | A 3 and 17 | R then S | $^1$H NMR (400 MHz, METHANOL-d$_4$) δ ppm 0.93-1.03 (m, 3 H), 1.21-1.35 (m, 3 H), 1.37-1.51 (m, 1 H), 1.52-1.96 (m, 7 H), 2.17-2.37 (m, 3 H), 2.49-2.67 (m, 2 H), 2.79-2.94 (m, 2 H), 3.33-3.40 (m, 1 H), 3.47-3.55 (m, 2 H), 3.56-3.68 (m, 2 H), 4.09-4.19 (m, 2 H), 4.20-4.31 (m, 2 H) | 3 D | m/z 382 (M + H)$^+$ (ESI$^+$), at 2.49 min, 202 nm |
| 5-4 | Isomer 1b: Ethyl 7-(4-ethyl-2-oxo-1-oxa-3,8-diazaspiro[4.5]dec-8-yl)-3-oxa-9-azabicyclo[3.3.1]nonane-9-carboxylate | A 3 and 17 | R then S | $^1$H NMR (400 MHz, METHANOL-d$_4$) δ ppm 0.94-1.05(m, 3 H), 1.20-1.36 (m, 3 H), 1.39-1.51 (m, 1 H), 1.52-1.96 (m, 7 H), 2.19-2.41 (m, 3 H), 2.49-2.68 (m, 2 H), 2.78-2.94 (m, 2 H), 3.34-3.41 (m, 1 H), 3.46-3.56 (m, 2 H), 3.56-3.68 (m, 2 H), 4.10-4.19 (m, 2 H), 4.20-4.31 (m, 2 H) | 3 D | m/z 382 (M + H)$^+$ (ESI$^+$), at 2.50 min, 202 nm |
| 5-4 | Isomer 2a: Ethyl 7-(4-ethyl-2-oxo-1-oxa-3,8-diazaspiro[4.5]dec-8-yl)-3-oxa-9-azabicyclo[3.3.1]nonane-9-carboxylate | A 3 and 17 | R then S | $^1$H NMR (400 MHz, METHANOL-d$_4$) δ ppm 0.92-1.06 (m, 3 H), 1.19-1.35 (m, 3 H), 1.38-1.51 (m, 1 H), 1.52-1.98 (m, 7 H), 2.03-2.19 (m, 2 H), 2.40-2.62 (m, 2 H), 2.83-3.03 (m, 2 H), 3.33-3.43 (m, 1 H), 3.59-3.76 (m, 3 H), 3.80-3.94 (m, 2 H), 4.06-4.26 (m, 4 H) | 3 D | m/z 382 (M + H)$^+$ (ESI$^+$), at 2.48 min, 202 nm |
| 5-4 | Isomer 2b: Ethyl 7-(4-ethyl-2-oxo-1-oxa-3,8-diazaspiro[4.5]dec-8-yl)-3-oxa-9-azabicyclo[3.3.1]nonane-9-carboxylate | A 3 and 17 | R then S | $^1$H NMR (400 MHz, METHANOL-d$_4$) δ ppm 0.91-1.06 (m, 3 H), 1.21-1.35 (m, 3 H), 1.39-1.52 (m, 1 H), 1.53-1.98 (m, 7 H), 2.03-2.18 (m, 2 H), 2.42-2.61 (m, 2 H), 2.85-2.99 (m, 2 H), 3.33-3.41 (m, 1 H), 3.60-3.75 (m, 3 H), 3.79-3.94 (m, 2 H), 4.05-4.23 (m, 4 H) | 3 D | m/z 382 (M + H)$^+$ (ESI$^+$), at 2.49 min, 202 nm |
| 5-5 | Isomer 1: Ethyl 7-(2-oxo-1,2-dihydro-1'H-spiro[indole-3,4'-piperidin]-1'-yl)-3-oxa-9-azabicyclo[3.3.1]nonane-9-carboxylate | A 3 and 18 | T | $^1$H NMR (400 MHz, METHANOL-d$_4$) δ ppm 1.20-1.38 (m, 3 H), 1.69-2.02 (m, 6 H), 2.32-2.53 (m, 2 H), 2.83-3.00 (m, 2 H), 3.06-3.25 (m, 2 H), 3.46-3.78 (m, 5 H), 4.11-4.23 (m, 2 H), 4.24-4.38 (m, 2 H), 6.84-6.96 (m, 1 H), 6.97-7.08 (m, 1 H), 7.16-7.27 (m, 1 H), 7.33-7.44 (m, 1 H) | 3 D | m/z 400 (M + H)$^+$ (ESI$^+$), at 3.01 min, 202 nm |
| 5-5 | Isomer 2: Ethyl 7-(2-oxo-1,2-dihydro-1'H-spiro[indole-3,4'-piperidin]-1'-yl)-3-oxa-9-azabicyclo[3.3.1]nonane-9-carboxylate | A 3 and 18 | T | $^1$H NMR (400 MHz, METHANOL-d$_4$) δ ppm 1.22-1.35 (m, 3 H), 1.70-2.01 (m, 6 H), 2.13-2.24 (m, 2 H), 2.80-2.96 (m, 2 H), 3.07-3.18 (m, 2 H), 3.66-3.75 (m, 2 H), 3.77-3.96 (m, 3 H), 4.07-4.23 (m, 4 H), 6.86-6.96 (m, 1 H), 6.98-7.08 (m, 1 H), 7.14-7.24 (m, 1 H), 7.34-7.45 (m, 1 H) | 3 D | m/z 400 (M + H)$^+$ (ESI$^+$), at 3.01 min, 202 nm |

TABLE 3-continued

NMR and LCMS properties and the methods used to prepare and purify compounds represented by Examples 1-8-2

| Ex. No. | Name | Synthetic Method and Intermediates Used | Purification Method | $^1$H NMR | LCMS Analysis System and Method | LCMS data |
|---|---|---|---|---|---|---|
| 6-1 | Isomer 1: Ethyl 7-{4-[acetyl(2-methylpropyl)amino]piperidin-1-yl}-3-oxa-9-azabicyclo[3.3.1]nonane-9-carboxylate | A 3 and 21 | U | $^1$H NMR (400 MHz, METHANOL-d$_4$) δ ppm 0.79-1.04 (m, 6 H), 1.22-1.37 (m, 3 H), 1.61-1.86 (m, 5 H), 1.87-2.34 (m, 9 H), 3.01-3.23 (m, 4 H), 3.52-4.02 (m, 6 H), 4.05-4.24 (m, 4 H) | 3 D | m/z 396 (M + H)$^+$ (ESI$^+$), at 2.99 min, 220 nm |
| 6-1 | Isomer 2: Ethyl 7-{4-[acetyl(2-methylpropyl)amino]piperidin-1-yl}-3-oxa-9-azabicyclo[3.3.1]nonane-9-carboxylate | A 3 and 21 | U | $^1$H NMR (400 MHz, METHANOL-d$_4$) δ ppm 0.79-1.03 (m, 6 H), 1.26 (t, J = 7.0 Hz, 3 H), 1.59-2.47 (m, 14 H), 2.98-3.20 (m, 4 H), 3.44-3.95 (m, 6 H), 4.15 (q, J = 6.9 Hz, 2 H), 4.20-4.31 (m, 2 H) | 3 D | m/z 396 (M + H)$^+$ (ESI$^+$), at 3.02 min, 220 nm |
| 6-2 | Isomer 1: Ethyl 7-{4-[acetyl(2,2-dimethylpropyl)amino]piperidin-1-yl}-3-oxa-9-azabicyclo[3.3.1]nonane-9-carboxylate | A 3 and 23 | V then W | $^1$H NMR (400 MHz, METHANOL-d$_4$) δ ppm 0.88-1.08 (m, 9 H), 1.20-1.35 (m, 3 H), 1.60-1.94 (m, 5 H), 1.99-2.31 (m, 7 H), 2.59-2.78 (m, 1 H), 2.89-3.02 (m, 1 H), 3.05-3.16 (m, 2 H), 3.17-3.23 (m, 2 H), 3.53-3.73 (m, 3 H), 3.76-3.91 (m, 2 H), 4.05-4.23 (m, 4 H) | 3 D | m/z 410 (M + H)$^+$ (ESI$^+$), at 3.33 min, 220 nm |
| 6-3 | Isomer 1: Ethyl 7-(4-{acetyl[(1-methylcyclopropyl)methyl]amino}piperidin-1-yl)-3-oxa-9-azabicyclo[3.3.1]nonane-9-carboxylate | A 3 and 25 | X then Y | $^1$H NMR (400 MHz, METHANOL-d$_4$) δ ppm 0.29-0.63 (m, 4 H), 0.94-1.16 (m, 3 H), 1.19-1.45 (m, 7 H), 1.85 (br. s., 3 H), 2.08-2.25 (m, 3 H), 2.27-2.85 (m, 6 H), 3.12-3.26 (m, 1 H), 3.37-3.45 (m, 1 H), 3.50-3.79 (m, 5 H), 4.11-4.21 (m, 2 H), 4.23-4.35 (m, 2 H) | 3 D | m/z 408 (M + H)$^+$ (ESI$^+$), at 3.10 min, 202 nm |
| 6-3 | Isomer 2: Ethyl 7-(4-{acetyl[(1-methylcyclopropyl)methyl]amino}piperidin-1-yl)-3-oxa-9-azabicyclo[3.3.1]nonane-9-carboxylate | A 3 and 25 | X then Y | $^1$H NMR (400 MHz, METHANOL-d$_4$) δ ppm 0.26-0.59 (m, 4 H), 0.93-1.13 (m, 3 H), 1.20-1.38 (m, 3 H), 1.62-1.80 (m, 4 H), 1.89 (m, 1 H), 1.99-2.37 (m, 8 H), 3.06-3.21 (m, 2 H), 3.22-3.29 (m, 2 H), 3.59-3.77 (m, 4 H), 3.78-3.93 (m, 2 H), 4.06-4.24 (m, 4 H) | 3 D | m/z 408 (M + H)$^+$ (ESI$^+$), at 3.06 min, 202 nm |
| 6-4 | Isomer 1: Ethyl 7-(4-{acetyl[(1-methylcyclobutyl)methyl]amino}piperidin-1-yl)-3-oxa-9-azabicyclo[3.3.1]nonane-9-carboxylate | A 3 and 27 | Z then AA | $^1$H NMR (400 MHz, METHANOL-d$_4$) δ ppm 1.08-1.35 (m, 7 H), 1.54-1.84 (m, 8 H), 1.97-2.20 (m, 5 H), 2.21-2.51 (m, 6 H), 3.01-3.28 (m, 5 H), 3.47-3.55 (m, 2 H), 3.56-3.70 (m, 2 H), 4.08-4.18 (m, 2 H), 4.20-4.29 (m, 2 H) | 3 D | m/z 422 (M + H)$^+$ (ESI$^+$), at 3.56 min, 215 nm |
| 6-4 | Isomer 2: Ethyl 7-(4-{acetyl[(1-methylcyclobutyl)methyl]amino}piperidin-1-yl)-3-oxa-9-azabicyclo[3.3.1]nonane-9-carboxylate | A 3 and 27 | Z then AA | $^1$H NMR (400 MHz, METHANOL-d$_4$) δ ppm 1.05-1.36 (m, 7 H), 1.56-1.96 (m, 9 H), 1.97-2.30 (m, 9 H), 2.31-2.49 (m, 1 H), 3.04-3.17 (m, 2 H), 3.20-3.27 (m, 1 H), 3.34-3.45 (m, 1 H), 3.59-3.75 (m, 3 H), 3.78-3.91 (m, 2 H), 4.07-4.24 (m, 4 H) | 3 D | m/z 422 (M + H)$^+$ (ESI$^+$), at 3.54 min, 215 nm |
| 6-5 | Isomer 1: Ethyl 7-{4-[acetyl(benzyl)amino]piperidin-1-yl}-3-oxa-9-azabicyclo[3.3.1]nonane-9-carboxylate | A 3 and 29 | AB then AC | $^1$H NMR (400 MHz, METHANOL-d$_4$) δ ppm 1.09-1.38 (m, 3 H), 1.54-1.83 (m, 6 H), 1.97-2.42 (m, 7 H), 2.97-3.16 (m, 2 H), 3.58-3.74 (m, 3 H), 3.77-3.91 (m, 2 H), 4.03-4.22 (m, 4 H), 4.37-4.53 (m, 1 H), 4.55-4.67 (m, 2 H), 7.11-7.45 (m, 5 H) | 3 D | m/z 430 (M + H)$^+$ (ESI$^+$), at 3.05 min, 202 nm |
| 6-5 | Isomer 2: Ethyl 7-{4-[acetyl(benzyl)amino]piperidin-1-yl}-3-oxa-9-azabicyclo[3.3.1]nonane-9-carboxylate | A 3 and 29 | AB then AC | $^1$H NMR (400 MHz, METHANOL-d$_4$) δ ppm 1.16-1.35 (m, 3 H), 1.54-1.82 (m, 5 H), 1.97-2.39 (m, 9 H), 2.87-3.04 (m, 2 H), 3.43-3.65 (m, 4 H), 3.73-4.51 (m, 5 H), 4.52-4.68 (m, 2 H), 7.13-7.41 (m, 5 H) | 3 D | m/z 430 (M + H)$^+$ (ESI$^+$), at 3.06 min, 202 nm |
| 6-6 | Isomer 1: Ethyl 7-(2-oxo-1,4'-bipiperidin-1'-yl)-3-oxa-9-azabicyclo[3.3.1]nonane-9-carboxylate | A 3 and 30 | AD then AE | $^1$H NMR (400 MHz, METHANOL-d$_4$) δ ppm 1.26 (t, J = 7.0 Hz, 3 H), 1.57-1.71 (m, 4 H), 1.72-1.89 (m, 6 H), 2.18-2.45 (m, 7 H), 3.00-3.10 (m, 2 H), 3.23-3.29 (m, 2 H), 3.46-3.55 (m, 2 H), 3.56-3.67 (m, 2 H), 4.15 (q, J = 7.0 Hz, 2 H), 4.20-4.30 (m, 2 H), 4.33-4.45 (m, 1 H) | 3 D | m/z 380 (M + H)$^+$ (ESI$^+$), at 3.06 min, 220 nm |
| 6-6 | Isomer 2: Ethyl 7-(2-oxo-1,4'-bipiperidin-1'-yl)-3-oxa-9-azabicyclo[3.3.1]nonane-9-carboxylate | A 3 and 30 | AD then AE | $^1$H NMR (400 MHz, METHANOL-d$_4$) δ ppm 1.21-1.33 (m, 3 H), 1.57-1.86 (m, 10 H), 2.03-2.14 (m, 2 H), 2.19-2.31 (m, 2 H), 2.33-2.43 (m, 2 H), 3.08-3.19 (m, 2 H), 3.23-3.28 (m, 2 H), 3.57-3.73 (m, 3 H), 3.79-3.92 (m, 2 H), 4.08-4.21 (m, 4 H), 4.34-4.47 (m, 1 H) | 3 D | m/z 380 (M + H)$^+$ (ESI$^+$), at 2.52 min, 220 nm |
| 6-7 | Isomer 1: Ethyl 7-[4-(2-oxoazepan-1-yl)piperidin-1-yl]-3-oxa-9-azabicyclo[3.3.1]nonane-9-carboxylate | A 3 and 33 | AF then AG | $^1$H NMR (400 MHz, METHANOL-d$_4$) δ ppm 1.18-1.35 (m, 3 H), 1.51-1.85 (m, 11 H), 2.01-2.42 (m, 4 H), 2.48-2.61 (m, 2 H), 2.98-3.18 (m, 2 H), 3.33-3.43 (m, 2 H), 3.46-3.73 (m, 4 H), 3.79-3.91 (m, 2 H), 4.06-4.29 (m, 4 H), 4.33-4.47 (m, 1 H) | 3 D | m/z 394 (M + H)$^+$ (ESI$^+$), at 2.76 min, 202 nm |

TABLE 3-continued

NMR and LCMS properties and the methods used to prepare and purify compounds represented by Examples 1-8-2

| Ex. No. | Name | Synthetic Method and Intermediates Used | Purification Method | ¹H NMR | LCMS Analysis System and Method | LCMS data |
|---|---|---|---|---|---|---|
| 6-7 | Isomer 2: Ethyl 7-[4-(2-oxoazepan-1-yl)piperidin-1-yl]-3-oxa-9-azabicyclo[3.3.1]nonane-9-carboxylate | A 3 and 33 | AF then AG | $^1$H NMR (400 MHz, METHANOL-d$_4$) δ ppm 1.22-1.34 (m, 3 H), 1.53-1.82 (m, 12 H), 2.01-2.14 (m, 2 H), 2.17-2.28 (m, 2 H), 2.46-2.61 (m, 2 H), 3.04-3.16 (m, 2 H), 3.34-3.42 (m, 2 H), 3.56-3.75 (m, 3 H), 3.78-3.92 (m, 2 H), 4.06-4.22 (m, 4 H), 4.33-4.47 (m, 1 H) | 3 D | m/z 394 (M + H)$^+$ (ESI$^+$), at 2.71 min, 202 nm |
| 7-1 | Isomer 1: Ethyl 7-{4-[(1-methylcyclobutyl)carbamoyl]piperidin-1-yl}-3-oxa-9-azabicyclo[3.3.1]nonane-9-carboxylate | C 3, 34 and 35 | AH then AI | $^1$H NMR (400 MHz, METHANOL-d$_4$) δ ppm 1.20-1.34 (m, 3 H), 1.41 (s, 3 H), 1.62-2.03 (m, 11 H), 2.07-2.44 (m, 8 H), 2.98-3.11 (m, 2 H), 3.47-3.56 (m, 2 H), 3.57-3.67 (m, 2 H), 4.10-4.19 (m, 2 H), 4.20-4.30 (m, 2 H) | 3 D | m/z (M + H)$^+$ (ESI$^+$), at 2.43 min, 202 nm |
| 7-1 | Isomer 2: Ethyl 7-{4-[(1-methylcyclobutyl)carbamoyl]piperidin-1-yl}-3-oxa-9-azabicyclo[3.3.1]nonane-9-carboxylate | C 3, 34 and 35 | AH then AI | $^1$H NMR (400 MHz, METHANOL-d$_4$) δ ppm 1.18-1.34 (m, 3 H), 1.41 (s, 3 H), 1.62-1.90 (m, 8 H), 1.93-2.34 (m, 9 H), 2.86-2.99 (m, 1 H), 3.01-3.14 (m, 2 H), 3.54-3.73 (m, 3 H), 3.77-3.90 (m, 2 H), 4.05-4.25 (m, 4 H) | 3 D | m/z 394 (M + H)$^+$ (ESI$^+$), at 2.83 min, 202 nm |
| 7-2 | Isomer 1: Ethyl 7-{4-[(2-methylpropyl)carbamoyl]piperidin-1-yl}-3-oxa-9-azabicyclo[3.3.1]nonane-9-carboxylate | C 3, 34 and 20 | AJ then AK | $^1$H NMR (400 MHz, METHANOL-d$_4$) δ ppm 0.85-0.96 (m, 6 H), 1.22-1.33 (m, 3 H), 1.61-1.85 (m, 7 H), 2.12-2.38 (m, 6 H), 2.93-3.08 (m, 4 H), 3.48-3.56 (m, 2 H), 3.57-3.67 (m, 2 H), 4.10-4.19 (m, 2 H), 4.20-4.29 (m, 2 H) | 3 D | m/z 382 (M + H)$^+$ (ESI$^+$), at 2.81 min, 202 nm |
| 7-3 | Isomer 1: Ethyl 7-{4-[(cyclobutylmethyl)carbamoyl]piperidin-1-yl}-3-oxa-9-azabicyclo[3.3.1]nonane-9-carboxylate | C 3, 34 and 36 | AL then AM | $^1$H NMR (400 MHz, METHANOL-d$_4$) δ ppm 1.22-1.33 (m, 3 H), 1.60-1.81 (m, 8 H), 1.82-1.96 (m, 2 H), 1.97-2.09 (m, 2 H), 2.11-2.36 (m, 6 H), 2.41-2.55 (m, 1 H), 2.92-3.05 (m, 2 H), 3.13-3.23 (m, 2 H), 3.45-3.54 (m, 2 H), 3.55-3.66 (m, 2 H), 4.10-4.18 (m, 2 H), 4.19-4.28 (m, 2 H) | 3 D | m/z 394 (M + H)$^+$ (ESI$^+$), at 2.95 min, 202 nm |
| 7-4 | Isomer 1: Ethyl 7-[4-(azepan-1-ylcarbonyl)piperidin-1-yl]-3-oxa-9-azabicyclo[3.3.1]nonane-9-carboxylate | C 3, 34 and 37 | AN then AO | $^1$H NMR (400 MHz, METHANOL-d$_4$) δ ppm 1.20-1.40 (m, 5 H), 1.51-1.87 (m, 13 H), 2.14-2.38 (m, 5 H), 2.55-2.69 (m, 1 H), 2.95-3.06 (m, 2 H), 3.46-3.66 (m, 7 H), 4.10-4.18 (m, 2 H), 4.19-4.31 (m, 2 H) | 3 D | m/z 408 (M + H)$^+$ (ESI$^+$), at 3.28 min, 202 nm |
| 8-1 | Isomer 1: Methyl 7-(4-(N-((1-methylcyclobutyl)methyl)acetamido)piperidin-1-yl)-3-oxa-9-azabicyclo[3.3.1]nonane-9-carboxylate | A 27 and 39 | AP then AQ | $^1$H NMR (400 MHz, Methanol-d$_4$) δ 4.28-4.17 (m, 2H), 3.71 (s, 3H), 3.67-3.45 (m, 6H), 3.09-2.98 (m, 2H), 2.44-2.19 (m, 6H), 2.17 (s, 1.5H), 2.12-2.02 (m, 3H), 2.01 (s, 1.5H), 1.83-1.55 (m, 9H), 1.23 (s, 1.5H), 1.12 (s, 1.5H). | 3 D | m/z 408 (M + H)$^+$ (ESI$^+$), at 3.18 min, 202 nm |
| 8-1 | Isomer 2: Methyl 7-(4-(N-((1-methylcyclobutyl)methyl)acetamido)piperidin-1-yl)-3-oxa-9-azabicyclo[3.3.1]nonane-9-carboxylate | A 27 and 39 | AP | $^1$H NMR (400 MHz, Methanol-d$_4$) δ 4.15-4.07 (m, 2H), 3.89-3.78 (m, 2H), 3.70-3.58 (m, 4H), 3.29 (s, 1H), 3.24 (s, 1H), 3.14-3.06 (m, 2H), 2.44-2.30 (m, 1H), 2.29-2.19 (m, 1H), 2.17 (s, 2H), 2.16-2.02 (m, 6H), 2.01 (s, 2H), 1.96-1.83 (m, 1H), 1.83-1.55 (m, 9H), 1.23 (s, 1.5H), 1.12 (s, 1.5H). | 3 D | m/z 408 (M + H)$^+$ (ESI$^+$), at 3.10 min, 202 nm |
| 8-2 | Isomer 1: Methyl 7-(4-(N-benzylacetamido)piperidin-1-yl)-3-oxa-9-azabicyclo[3.3.1]nonane-9-carboxylate | A 39 and 29 | AR | $^1$H NMR (400 MHz, Methanol-d$_4$) δ 7.42-7.33 (m, 1H), 7.31-7.13 (m, 4H), 4.65-4.54 (m, 2H), 4.50-4.36 (m, 1H), 4.27-4.14 (m, 2H), 3.89-3.77 (m, 1H), 3.69 (s, 3H), 3.63-3.45 (m, 4H), 3.02-2.92 (m, 2H), 2.41-2.13 (m, 4H), 2.28 (s, 1.5H), 2.04 (s, 1.5H), 1.84-1.54 (m, 6H). | 3 C | m/z 416 (M + H)$^+$ (ESI$^+$), at 2.79 min, 202 nm |
| 8-2 | Isomer 2: Methyl 7-(4-(N-benzylacetamido)piperidin-1-yl)-3-oxa-9-azabicyclo[3.3.1]nonane-9-carboxylate | A 39 and 29 | AR | $^1$H NMR (400 MHz, Methanol-d$_4$) δ 7.40-7.33 (m, 1H), 7.31-7.15 (m, 4H), 4.66-4.56 (m, 2H), 4.49-4.39 (m, 1H), 4.14-4.04 (m, 2H), 3.89-3.76 (m, 2H), 3.70 (s, 3H), 3.68-3.55 (m, 3H), 3.08-2.99 (m, 2H), 2.28 (s, 1.5H), 2.25-2.15 (m, 2H), 2.08-1.99 (m, 2H), 2.05 (s, 1.5H), 1.81-1.57 (m, 6H). | 3 C | m/z 416 (M + H)$^+$ (ESI$^+$), at 2.79 min, 202 nm |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen,* 2008). ERK1/2 phosphorylation is a downstream consequence of both Gq/11 and Gi/o protein coupled receptor activation, making it highly suitable for the assessment of M$_1$, M$_3$ (Gq/11 coupled) and M$_2$, M$_4$ receptors (Gi/o coupled), rather than using different assay formats for different receptor subtypes. CHO cells stably expressing the human muscarinic M$_1$, M$_2$, M$_3$ or M$_4$ receptor were plated (25K/well) onto 96-well tissue culture plates in MEM-alpha+10% dialysed FBS. Once adhered, cells were serum-starved overnight. Agonist stimulation was performed by the addition of 5 µL agonist to the cells for 5 min (37° C.). Media was removed and 50 µL of lysis buffer added. After 15 min, a 4 µL sample was transferred to 384-well plate and 7 µL of detection mixture added. Plates were incubated for 2 h with gentle agitation in the dark and then read on a PHERAstar plate reader. $pEC_{50}$ and $E_{max}$ figures were calculated from the resulting data for each receptor subtype and the results are set out in Table 4 below.

For the vast majority of examples at least two diastereomers exist and these have been separated, unless otherwise stated, using the techniques of reversed phase HPLC, chiral HPLC or chiral SFC. Isomer assignment (Isomer 1, Isomer 2, etc.) is based on the retention time of the compound using the separation technique that was performed in the final purification step. By implication, this could be reversed phase HPLC, chiral HPLC or chiral SFC retention time, and this will vary from compound to compound.

Analytical data for active isomers is reported in Table 3. Data for several weakly active compounds are included in Table 4 to highlight the preference for absolute stereochemistry.

TABLE 4

| | Muscarinic Activity | | | |
|---|---|---|---|---|
| Ex. No. | $pEC_{50}$ M1 (% Emax cf. ACh) | $pEC_{50}$ M2 (% Emax cf. ACh) | $pEC_{50}$ M3 (% Emax cf. ACh) | $pEC_{50}$ M4 (% Emax cf. ACh) |
| ACh | 8.33 (102) | 7.82 (105) | 8.12 (115) | 8.09 (110) |
| 1-1 Isomer 1 | 6.37 (116) | 6.24 (57) | <4.70 (13) | 7.28 (100) |
| 1-2 Isomer 1 | 7.82 (96) | 7.06 (69) | <4.70 (2) | 8.54 (78) |
| 1-2 Isomer 2 | 7.11 (67) | <4.70 (10) | <4.70 (2) | 7.88 (51) |
| 1-3 Isomer 1 | 7.26 (124) | 6.55 (112) | 5.60 (40) | 8.14 (99) |
| 1-3 Isomer 2 | 6.50 (45) | <4.70 (11) | <4.70 (5) | 6.95 (81) |
| 2-1 Isomer 1 | 6.60 (44) | NT | NT | <4.70 (17) |
| 2-1 Isomer 2 | 6.80 (40) | NT | NT | <4.70 (20) |
| 2-2 Isomer 1 | <4.70 (63) | <4.70 (3) | <4.70 (4) | 7.44 (61) |
| 2-2 Isomer 2 | <4.70 (10) | <4.70 (3) | <4.70 (5) | 6.95 (37) |
| 2-3 Isomer 1 | 6.71 (77) | 6.54 (45) | <4.70 (9) | 8.19 (99) |
| 2-3 Isomer 2 | 6.76 (34) | <4.70 (10) | <4.70 (5) | 7.94 (65) |
| 3-1 Isomer 1 | 5.86 (97) | NT | NT | 6.89 (94) |
| 3-1 Isomer 2 | 5.86 (79) | NT | NT | 6.51 (78) |
| 4-1 Isomer 1 | 6.81 (108) | 6.60 (87) | <4.70 (11) | 7.51 (114) |
| 4-1 Isomer 2 | 6.40 (47) | <4.70 (17) | <4.70 (4) | 7.00 (59) |
| 5-1 Isomer 1 | 7.14 (47) | <4.70 (8) | <4.70 (0) | <4.70 (13) |
| 5-1 Isomer 2 | 6.85 (66) | <4.70 (13) | <4.70 (8) | 7.47 (41) |
| 5-2 Isomer 1 | 6.50 (82) | NT | NT | 6.52 (36) |
| 5-2 Isomer 2 | 7.36 (61) | <4.70 (8) | <4.70 (5) | <4.70 (18) |
| 5-3 Isomer 1 | 5.84 (75) | NT | NT | 6.08 (33) |
| 5-3 Isomer 2 | 6.90 (73) | <4.70 (4) | <4.70 (5) | <4.70 (17) |
| 5-4 Isomer 1a | 5.83 (76) | <4.70 (3) | <4.70 (4) | 6.84 (81) |
| 5-4 Isomer 1b | <4.70 (9) | NT | NT | 6.50 (30) |
| 5-4 Isomer 2a | 6.01 (75) | NT | NT | 6.70 (61) |
| 5-4 Isomer 2b | 7.13 (25) | <4.70 (1) | <4.70 (4) | <4.70 (20) |
| 5-5 Isomer 1 | 6.54 (75) | 6.91 (24) | <4.70 (4) | 7.67 (99) |
| 5-5 Isomer 2 | 7.27 (108) | 7.12 (67) | NT | 8.07 (108) |
| 6-1 Isomer 1 | 6.75 (93) | <4.70 (26) | <4.70 (7) | 6.82 (77) |
| 6-1 Isomer 2 | 7.21 (102) | 6.49 (90) | <4.70 (62) | 7.76 (111) |
| 6-2 Isomer 1 | 6.21 (71) | NT | NT | 5.98 (45) |
| 6-3 Isomer 1 | 6.92 (124) | 6.45 (36) | <4.70 (390) | 7.22 (93) |
| 6-3 Isomer 2 | 6.71 (90) | <4.70 (11) | <4.70 (9) | 6.41 (44) |
| 6-4 Isomer 1 | 7.84 (103) | 6.44 (33) | NT | 7.37 (80) |
| 6-4 Isomer 2 | 7.47 (72) | <4.70 (15) | <4.70 (19) | 6.69 (38) |
| 6-5 Isomer 1 | 6.78 (92) | <4.70 (11) | <4.70 (13) | 6.52 (50) |
| 6-5 Isomer 2 | 7.80 (91) | 5.63 (68) | 5.55 (83) | 6.84 (73) |
| 6-6 Isomer 1 | 6.60 (103) | 6.47 (60) | <4.70 (7) | 7.72 (109) |
| 6-6 Isomer 2 | 6.01 (50) | <4.70 (6) | <4.70 (3) | 7.09 (48) |
| 6-7 Isomer 1 | 6.19 (111) | 5.99 (87) | <4.70 (28) | 7.12 (105) |
| 6-7 Isomer 2 | 5.66 (41) | <4.70 (5) | <4.70 (2) | 6.76 (52) |
| 7-1 Isomer 1 | 6.42 (91) | NT | NT | 6.49 (76) |
| 7-1 Isomer 2 | 5.76 (62) | NT | NT | <4.70 (54) |

TABLE 4-continued

| | Muscarinic Activity | | | |
|---|---|---|---|---|
| Ex. No. | $pEC_{50}$ M1 (% Emax cf. ACh) | $pEC_{50}$ M2 (% Emax cf. ACh) | $pEC_{50}$ M3 (% Emax cf. ACh) | $pEC_{50}$ M4 (% Emax cf. ACh) |
| 7-2 Isomer 1 | 7.10 (96) | NT | NT | 6.34 (72) |
| 7-3 Isomer 1 | 7.45 (100) | 5.83 (62) | <4.70 (57) | 6.56 (97) |
| 7-4 Isomer 1 | 6.26 (85) | NT | NT | <4.70 (65) |
| 8-1 Isomer 1 | 7.07 (123) | NT | NT | 6.81 (77) |
| 8-1 Isomer 2 | 6.63 (86) | NT | NT | 6.24 (47) |
| 8-2 Isomer 1 | 7.10 (99) | NT | NT | 6.18 (54) |
| 8-2 Isomer 2 | 6.22 (60) | NT | NT | <4.70 (27) |

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1):

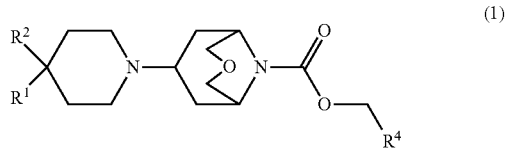

or a pharmaceutically acceptable salt thereof, wherein:
$R^1$ is $CONR^8R^9$;
$R^2$ is selected from hydrogen; fluorine; cyano; hydroxy; amino; and a $C_{1-3}$ non-aromatic hydrocarbon group which is optionally substituted with one to six fluorine atoms and wherein one of the carbon atoms of the hydrocarbon group may optionally be replaced by a heteroatom selected from O, N and S and oxidized forms thereof;
$R^4$ is H or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;
$R^8$ is hydrogen, a non-aromatic $C_{1-6}$ hydrocarbon group optionally substituted with one or more fluorine atoms, or $R^8$ can be joined together with $R^9$ to form an optionally substituted monocyclic or bicyclic ring containing 0, 1, 2 or 3 heteroatoms selected from O, N and S and oxidized forms thereof, and
$R^9$ is a non-aromatic $C_{1-6}$ hydrocarbon group optionally substituted with one or more fluorine atoms, or $R^9$ can be joined together with $R^8$ to form an optionally substituted monocyclic or bicyclic ring containing 0, 1, 2 or 3 heteroatoms selected from O, N and S and oxidized forms thereof.

2. The compound according to claim 1, or a pharmaceutically acceptable salt thereof, wherein $R^2$ is H.

3. The compound according to claim 1, or a pharmaceutically acceptable salt thereof, wherein $R^4$ is H or methyl.

4. The compound according to claim 1, or a pharmaceutically acceptable salt thereof, wherein $R^2$ is hydrogen and $R^1$ is selected from the group consisting of:

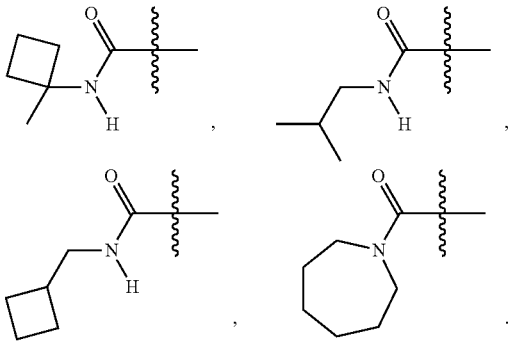

5. The compound according to claim 1, which is selected from the group consisting of:
Ethyl 7-{4-[(1-methylcyclobutyl)carbamoyl]piperidin-1-yl}-3-oxa-9-azabicyclo[3.3.1]nonane-9-carboxylate;
Ethyl 7-{4-[(2-methylpropyl)carbamoyl]piperidin-1-yl}-3-oxa-9-azabicyclo[3.3.1]nonane-9-carboxylate;
Ethyl 7-{4-[(cyclobutylmethyl)carbamoyl]piperidin-1-yl}-3-oxa-9-azabicyclo[3.3.1]nonane-9-carboxylate;
Ethyl 7-[4-(azepan-1-ylcarbonyl)piperidin-1-yl]-3-oxa-9-azabicyclo[3.3.1]nonane-9-carboxylate;
Methyl 7-{4-[(1-methylcyclobutyl)carbamoyl]piperidin-1-yl}-3-oxa-9-azabicyclo[3.3.1]nonane-9-carboxylate;
Methyl 7-{4-[(2-methylpropyl)carbamoyl]piperidin-1-yl}-3-oxa-9-azabicyclo[3.3.1]nonane-9-carboxylate;
Methyl 7-{4-[(cyclobutylmethyl)carbamoyl]piperidin-1-yl}-3-oxa-9-azabicyclo[3.3.1]nonane-9-carboxylate; and
Methyl 7-[4-(azepan-1-ylcarbonyl)piperidin-1-yl]-3-oxa-9-azabicyclo[3.3.1]nonane-9-carboxylate;
or a pharmaceutically acceptable salt thereof.

6. A pharmaceutical composition comprising a compound as defined in claim 1, or a pharmaceutically acceptable salt thereof, and a pharmaceutically acceptable excipient.

7. A method of treating a cognitive disorder or psychotic disorder or for the treatment or lessening the severity of acute, chronic, neuropathic, or inflammatory pain comprising administering an effective amount of the compound according to claim 1, or a pharmaceutically acceptable salt thereof, to a subject in need thereof.

8. The method according to claim 7, wherein the cognitive disorder is Alzheimer's disease.

9. The method according to claim 7, wherein the cognitive disorder is dementia with Lewy bodies.

10. The method according to claim 7, wherein the cognitive disorder is schizophrenia.

* * * * *